United States Patent
Wolffe et al.

(10) Patent No.: US 6,610,489 B2
(45) Date of Patent: Aug. 26, 2003

(54) PHARMACOGENOMICS AND IDENTIFICATION OF DRUG TARGETS BY RECONSTRUCTION OF SIGNAL TRANSDUCTION PATHWAYS BASED ON SEQUENCES OF ACCESSIBLE REGIONS

(75) Inventors: Alan Wolffe, Orinda, CA (US); Fyodor Urnov, Richmond, CA (US); Dmitry Guschin, Richmond, CA (US); Trevor Collingwood, San Pablo, CA (US); Xiao-Yong Li, Richmond, CA (US); Brian Johnstone, Benicia, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 09/844,265

(22) Filed: Apr. 27, 2001

(65) Prior Publication Data

US 2002/0127559 A1 Sep. 12, 2002

Related U.S. Application Data

(60) Provisional application No. 60/200,590, filed on Apr. 28, 2000, provisional application No. 60/214,674, filed on Jun. 27, 2000, and provisional application No. 60/228,608, filed on Aug. 28, 2000.

(51) Int. Cl.[7] ............................ C12Q 1/68; G01N 33/00
(52) U.S. Cl. ............................................ 435/6; 435/7.1
(58) Field of Search ....................................... 435/6, 7.1

(56) References Cited

U.S. PATENT DOCUMENTS

| | | |
|---|---|---|
| 5,176,996 A | 1/1993 | Hogan et al. |
| 5,422,251 A | 6/1995 | Fresco |
| 5,436,142 A | 7/1995 | Wigler et al. |
| 5,501,964 A | 3/1996 | Wigler et al. |
| 5,525,471 A | 6/1996 | Zeng |
| 5,585,245 A | 12/1996 | Johnsson et al. |
| 5,695,937 A | 12/1997 | Kinzler et al. |
| 5,789,538 A | 8/1998 | Rebar et al. |
| 5,866,330 A | 2/1999 | Kinzler et al. |
| 5,935,830 A | 8/1999 | Meyer, Jr. et al. |
| 5,958,738 A | 9/1999 | Lindemann et al. |
| 5,998,140 A | 12/1999 | Dervan et al. |
| 6,007,988 A | 12/1999 | Choo et al. |
| 6,013,453 A | 1/2000 | Choo et al. |
| 6,090,947 A | 7/2000 | Dervan et al. |
| 6,218,128 B1 * | 4/2001 | Klein et al. .................. 435/7.1 |
| 2002/0045158 A1 * | 4/2002 | Case ............................. 435/4 |

FOREIGN PATENT DOCUMENTS

| | | |
|---|---|---|
| WO | WO 93/06121 | 4/1993 |
| WO | WO 94/08051 | 4/1994 |
| WO | WO 95/12608 | 5/1995 |
| WO | WO 95/19431 | 7/1995 |
| WO | WO 95/30642 | 11/1995 |
| WO | WO 95/35503 | 12/1995 |
| WO | WO 98/44350 | 10/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 0041566 | 7/2000 |
| WO | WO 00/42219 | 7/2000 |

OTHER PUBLICATIONS

Carson and Hamilton, Developmentally Specific Effects of the DNA Cross.., Dec. 1997, pp325–337.*
Hershkovitz and Riggs, "Ligation–Mediated PCR for Chromatin–Structure Analysis of Interphase and Metaphase Chromatin," *Methods: A Companion in Methods in Enzynology* 11:253–263 (1997).
Gould Rothberg et al., "Integrating Expression–Based Drug Response and SNP–Based Pharmacogenetic Strategies Into a Single Comprehensive Pharmacogenomics Program," *"Drug Development Research* 49:54–64 (2000).
Rusterholz et al., "Interleukin–2 (IL–2) Regulates the Accessibility of the IL–2–Responsive Enhancer in the IL–2 Receptor α Gene to Transcription Factors," *Molecular and Cellular Biology* 19(4):2681–2689 1999).
Simpson, R.T., "Chromatin Structure and Analysis of Mechanisms of Activators and Repressor," *Methods: A Companion in Methods in Enzynology* 15:283–294 (1998).
Versaw et al., "Mitogen–Activated Protein Kinases Enhance Long–Range Activation by the β–Globin locus Control Region," *Proc. Natl. Acad. Sci. U.S.A.* 95:8756–8760 (1998).
Gross & Garrard, "Nuclease Hypersensitive Sites in Chromatin," *Annual Review of Biochemistry* 57:159–197 (1988).
Simpson, "In Vivo Methods to Analyze Chromatin Structure," *Current Opinions in Genetics & Development* 9:225–229 (1999).
Antequera et al., "Specific Protection of Methylated CpGs in Mammalian Nuclei," *Cell* 58:509–517 (1989).
Bird, "The Essential of DNA Methylation," *Cell* 70:5–8 (1992).
Bird et al., "Methylation–Induced Repression Belts, Braces, and Chromatin," *Cell* 99:451–454 (1999).

(List continued on next page.)

Primary Examiner—Kenneth R. Horlick
(74) Attorney, Agent, or Firm—Robins & Pasternak LLP; Sean M. Brennan

(57) ABSTRACT

Methods for the identification of a drug target, wherein the drug target is a component of a signal transduction pathway, are provided. The methods are based, in part, on selection of a gene of therapeutic interest and determination of regulatory DNA sequences which regulate expression of the gene in a cell of interest, followed by reconstruction of signal transduction pathways which act on molecules which bind to the regulatory sequence. Also provided are methods for assessing potential pharmacological effects and/or side effects of an agent, based on the effect of the agent on the distribution and properties of accessible regions in cellular chromatin.

14 Claims, 20 Drawing Sheets

OTHER PUBLICATIONS

Bitko & Barik, "Persistent Activation of Re1A by Respiratory Syncytial Virus Involves Protein Kinase C, Underphosphorylated IkBβ, and Sequestration of Protein Phosphatase 2A by the Viral Phosphoprotein," *Journal of Virology* 72(7):5610–5618 (1988).

Bringmann et al., "Antibodies Specific for $N^6$–Methyladenosine React with Intact snRNPs U2 and U4/U6," *FEBS* 213(2):309–315 (1987).

Cantley, "Translocating Tubby," *Science* 292:2019–2020 (2001).

Cartwright et al., "Cleavage of Chromatin with Methidiumpropyl–EDTA–iron(II)," *Proc. Natl. Acad. Sci. U.S.A.* 80:3213–3214 (1983).

Chern et al., "The Regulator of MAT2(ROM2) Proteins Binds to Early Maturation Promoters and Represses PvAL-F–Activated Transcription," *Plant Cell* 8:305–621 (1996).

Cheung et al., "Synergistic Coupling of Histone H3 Phosphorylation and Acetylation in Response to Epidermal Growth Factor Stimulation," *Molecular Cell* 5:905–915 (2000).

Cho et al., "Analysis of the C–Terminal Region of *Arabidopsis Thaliana* APETALA1 as a Transcription Activation Domain," *Plant Mol. Biol.* 40:419–429 (1999).

Collingwood et al., "Nuclear Receptors: Coactivators, Corepressors and Chromatin Remodeling in the Control of Transcription," *J. Mol. Endocrinol.* 23:255–275 (1999).

Darnell, "Jak–STAT Pathways and Transcriptional Activation in Response to IFNs and Other Extracellular Signaling Proteins," *Science* 264:1415–1421 (1994).

Darnell, "STATS and Gene Regulation," *Science* 277:1630–1635 (1997).

Doyle & Hunt, "Reduced Nuclear Factor kB (p65) Expression in Rat Primary Sensory Neurons After Peripheral Nerve Injury," *Neuroreport* 8(13):2937–2942 (1997).

Eichelbaum, M. et. al., "Influence of Pharmacogenetics on Drug Disposition and Response," *Clin. EP. Pharmacol. Physiol.* 23(10–11):983–985 (1996).

Fields et al., "A Novel Genetic System to Detect Protein–Protein Interactions," *Nature* 340:245–246 (1989).

Garrington et al., "Organization and Regulation of Mitogen–Activated Protein Kinase Signaling Pathways," *Current Opin. Cell Biol.* 11:211–218 (1999).

Gilmour et al., "Detecting Protein–DNA Interactions in vivo: Distribution of RNA Polymerase on Specific Bacterial Genes," *Proc. Natl. Acad. Sci. U.S.A.* 81:4275–4279 (1984).

Goff et al., "Identification of Functional Domains in the Maize Transcriptional Activator C1: Comparison of Wild-Type and Dominant Inhibitor Proteins," *Genes Dev.* 5:298–309 (1991).

Gong et al., "A Constitutively Expressed Myc–Like Gene Involved in Anthocyanin Biosynthesis form *Perilla Frutescens*: Molecular Characterization, Heterologous Expression in Transgenic Plants and Transactivation in Yeast Cells," *Plant Molecular Biology* 41:33–44 (1999).

Greene et al., "Sequence of the Bacteriophage SP01 Gene Coding for Transcription Factor 1, a Viral Homologue of the Bacterial Type II DNA–Binding Proteins," *Proc. Natl. Acad. Sci. U.S.A.* 81:7031–7035 (1984).

Greisman et al., "A General Strategy for Selecting High–Affinity Zinc Finger Proteins for Diverse DNA Target Sites," *Science* 275:657–661 (1997).

Gutkind, "The Pathways Connecting G Protein–coupled Receptors to the Nucleus Through Divergent Mitogen–activated Protein Kinase Cascades," *J. Biol. Chem.* 273:1839–1842 (1998).

Hagman et al., "The VP16 Paradox: Herpes Simplex Virus VP16 Contains a Long–Range Activation Domain but Within the Natural Multiprotein Complex Activates Only from Promoter–Proximal Positions," *Journal of Virology* 71(8):5952–5962 (1997).

Hendrich et al., "Identification and Characterization of a Family of Mammalian Methyl–CpG Binding Proteins," *Molecular and Cellular Biology* 18(11):6538–6548 (1998).

Hertzberg et al., "Cleavage of DNA with Methidiumpropy-l–EDTA–Iron (III): Reaction Conditions and Product Analyses," *Biochemistry* 23:3934–3945 (1984).

Hobo et al., "A bZIP Factor, TRAB1, Interacts with VP1 and Mediates Abscisic Acid–Induced Transcription," *Proc. Natl. Acad. Sci. U.S.A.* 96(15):15348–15353 (1999).

Ihle, "STATs: Signal Transducers and Activators of Transcription," *Cell* 84:331–334 (1996).

Ihle, "Signaling by the Cytokine Receptor Superfamily in Normal and Transformed Hematopoietic Cells," *Advances in Cancer Research* 68:23–65 (1996).

Iyer et al., "The Transcriptional Program in the Response of Human Fibroblasts to Serum," *Science* 283:83–87 (1999).

Jamieson et al., "In Vitro Selection of Zinc Fingers with Altered DNA–Binding Specificity," *Biochemistry* 33:(19):5689–5695 (1994).

Jamieson et al., "A Zinc Finger Directory for High–Affinity DNA Recognition," *Proc. Natl. Acad. Sci. U.S.A.* 93:12834–12839 (1996).

Jones et al., "Cancer Epigenetics Comes of Age," *Nature Genet.* 21:163–167 (1999).

Joung et al., "A Bacterial Two–Hybrid Selection System for Studying Protein–DNA and Protein–Protein Interactions," *Proc. Natl. Acad. Sci. U.S.A.* 97:7382–7387 (2000).

Kamei et al., "A CBP Integrator Complex Mediates Transcriptional Activation and AP–1 Inhibition by Nuclear Receptors," *Cell* 85:403–414 (1996).

Kimura et al., "On the DNA Binding Protein II from *Bacillus Stearothermophilus*," *The Journal of Biological Chemistry* 258(6):4007–4011 (1983).

Kitabayashi et al., "Interaction and Functional Cooperation of the Leukemia–Associated Factors AML1 and P300 in Myeloid Cell Differentiation," *EMBO J.* 17(11):2994–3004 (1998).

Kladde et al., "Direct Study of DNA–Protein Interactions in Repressed and Active Chromatin in Living Cells," *EMBO J.* 15(22):6290–6300 (1996).

Knoepfler et al., "Sin Meets NuRD and Other Tails of Repression," *Cell* 99:447–450 (1999).

Kuo et al., "In Vivo Cross–Linking and Immunoprecipitation for Studying Dynamic Protein: DNA Associations in a Chromatin Environment," *Method* 19:425–433 (1999).

Lemon et al., "Nuclear Receptors Cofactors as Chromatin Remodelers," *Curr. Opin. Genet. Dev.* 9:499–504 (1999).

Leo et al., "The SRC Family of Nuclear Receptor Coactivators," *Gene* 245:1–11 (2000).

Lovett, "Toxicologist Brace For Genomics Revolution," *Science* 289:536–537 (2000).

Malik et al., "Transcriptional Regulation Through Mediator–Like Coactivators in Yeast and Metazoan Cells," *Trends Biochem. Sci.* 25:277–283 (2000).

Manteuffel–Cymborowska, "Nuclear Receptors, Their Coactivators and Modulation of Transcription," *Acta Biochim. Pol.* 46(1):77–89 (1999).

Margolin et al., "Krüppel–Associated Boxes are Potent Transcriptional Repression Domains," *Proc. Natl. Acad. Sci. U.S.A.* 91:4509–4513 (1994).

Maxam et al., "Sequencing End–Labeled DNA With Base–Specific Chemical Cleavages," *Meth. Enzymology 65*, (L. Grossman & K. Moldave, eds.) Academic Press, New York, pp. 499–560 (1980).

McKenna et al., "Nuclear Receptor Coactivators: Multiple Enzymes, Multiple Complexes, Multiple Functions," *Journal of Steroid Biochemistry and Molecular Biology* 69:3–12 (1999).

Murga et al., "Novel Molecular Mediators in the Pathway Connecting G–protein–coupled Receptors to MAP Kinase Cascades," *Trends Endocrinol. Metab.* 10:122–127 (1999).

Ogawa et al., "*Rice Gibberellin–Insensitive Gene Homolog, OsGAI*, Encodes a Nuclear–Localized Protein Capable of Gene Activation at Transcriptional Level," *Gene* 245:21–29 (2000).

O'Neill et al., *Methods in Enzymology* 274:189–197 Academic Press, San Diego (1996).

Pelling et al., "A Human Genomic Library Enriched in Transcriptionally Active Sequences (aDNA Library)," *Genome Res.* 10:874–886 (2000).

Pengue et al., "Repression of Transcriptional Activity at a Distance by the Evolutionarily Conserved DRAB Domain Present in a Subfamily of Zinc Finger Proteins," *Nuc. Acids Res.* 22(15):2908–2914 (1994).

Quelle et al., "Erythropoietin Induces Activation of Stat5 Through Association with Specific Tyrosines on the Receptor that Are Not Required for a Mitogenic Response," *Mol. Cell Biol.* 16(4):1622–1631 (1996).

Rebar et al., "Zinc Finger Phage: Affinity Selection of Fingers with New DNA–Binding Specificities," *Science* 263:671–673 (1994).

Rice et al., "Recognition of Native DNA Methylation by the PvuII Restriction Endonuclease," *Nucleic Acids Research* 28(16):3143–3150 (2000).

Robertson et al., "DNA Methylation: Past, Present and Future Directions," *Carcinogenesis* 21(3):461–467 (2000).

Robertson et al., "DNMT1 Forms a Complex with Rb, E2F1 and HDAC1 and Represses Transcription From E2F–Responsive Promoters," *Nature Genetics* 25:338–342 (2000).

Robyr et al., "Nuclear Hormone Receptor Coregulators in Action: Diversity for Shared Tasks," *Molecular Endocrinology* 14:329–347 (2000).

Rouviere–Yaniv et al., "Localization of the HU Protein on the *Escherichia coli* Nucleoid," *Cold Spring Harbor Symp. Quant. Biol.* 42:439–447 (1977).

Solomon et al., "Formaldehyde–Mediated DNA–Protein Crosslinking: A Probe for in vivo Chromatin Structures," *Proc. Natl. Acad. Sci. U.S.A.* 82:6470–6474 (1985).

Solomon et al., "Mapping Protein–DNA Interactions In Vivo with Formaldehyde: Evidence that Histone H4 is Retained on a Highly Transcribed Gene," *Cell* 53:937–947 (1988).

Sprenger–Haussels et al., "Transactivation Properties of Parsley Proline–Rich bZIP Transcription Factors," *The Plant Journal* 22(1):1–8 (2000).

Tanaka et al., "3–Å Resolution Structure of a Protein with Histone–Like Properties in Prokaryotes," *Nature* 310:376–381 (1984).

Tazi and Bird, "Alternative Chromatin Structure at CpG Islands," *Cell* 60:909–920 (1990).

Thiesen, "Multiple Genes Encoding Zinc Finger Domains Are Expressed in Human T Cells," *New Biologist* 2:363–374 (1990).

Torchia et al., "Co–Activators and Co–Repressors in the Integration of Transcriptional Responses," *Curr. Opin. Cell Biol.* 10:373–383 (1998).

Tullius et al., "Hydroxyl Radical Footprinting: A High–Resolution Method for Mapping Protein–DNA Contacts," *Methods in Enzymology* 155:(J. Ableson & M. Simon, eds.) Academic Press, San Diego, pp. 537–558 (1987).

Tyler et al., "The "Dark Side" of Chromatin Remodeling: Repressive Effects on Transcription," *Cell* 99:443–446 (1999).

Ulmasov et al., "Activation and Repression of Transcription by Auxin–Response Factors,"*Proc. Natl. Acad. Sci. USA* 96:5844–5849 (1999).

van Steensel and Henikoff, "Identification of In Vivo DNA Targets of Chromatin Proteins Using Tethered Dam Methyltransferase," *Nature Biotechnology* 18:424–428 (2000).

Wellinger et al., "In Vivo Mapping of Nucleosomes Using Psoralen–DNA Crosslinking Primer Extension," *Methods in Molecular Biology* 119:161–173 (1999).

Wines et al., "Introduction of a DNA Methyltransferase into *Drosophila* to Probe Chromatin Structure in vivo," *Chromasoma* 104:332–340 (1996).

Wingender et al., "Transfac, TRRD and Compel: Towards a Federated Database System on Transcriptional Regulation," *Nucleic Acids Res.* 25(1):265–268 (1997).

Witzgall et al., "The Krüppel–Associated Box–A (DRAB–A) Domain of Zinc Finger Proteins Mediates Transcriptional Repression," *Proc. Natl. Acad. Sci. U.S.A.* 91:4514–4518 (1994).

Wu et al., "Functional Analysis of HD2 Histone Deacetylase Homologues in *Arabidopsis thaliana*," *The Plant Journal* 22(1):19–27 (2000).

Wu et al., "VRAP Is an Adaptor Protein That Binds KDR, a Receptor for Vascular Endothelial Cell Growth Factor," *The Journal of Biological Chemistry* 275(9):6059–6062 (2000).

* cited by examiner

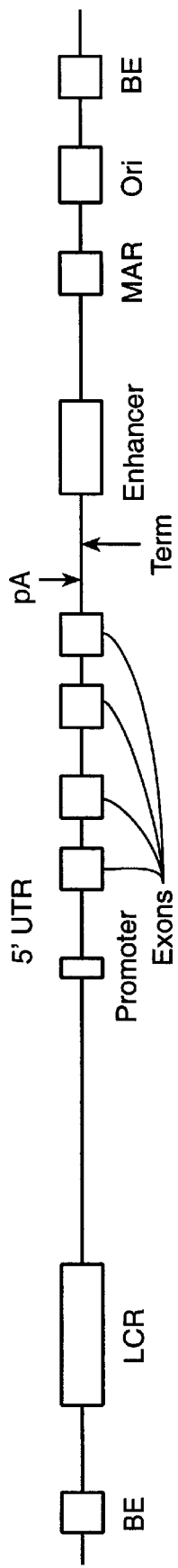
FIG._1
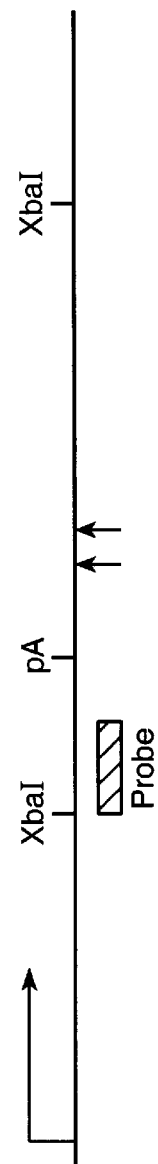
FIG._2A

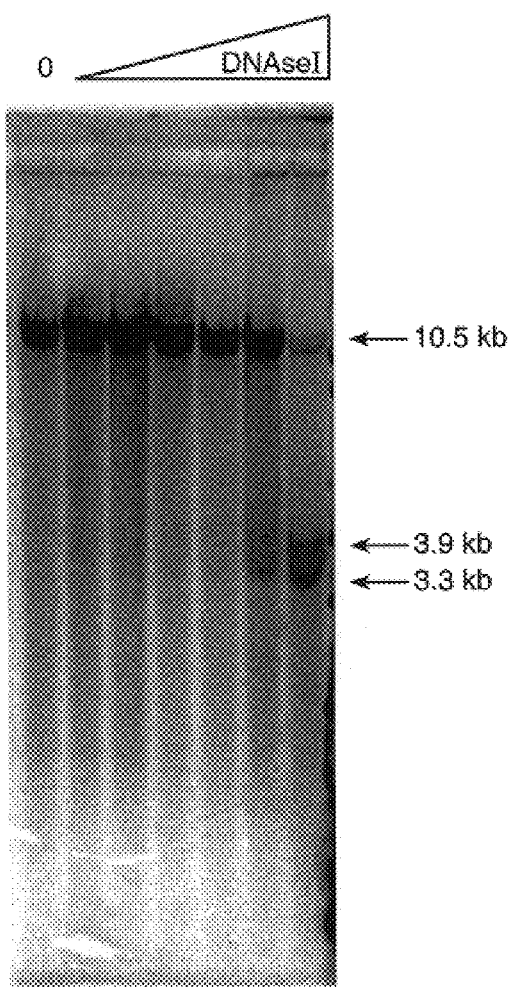
FIG._2B
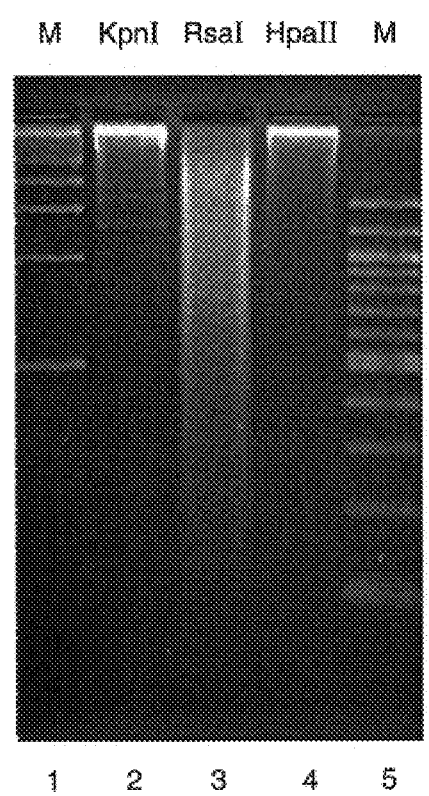
FIG._3

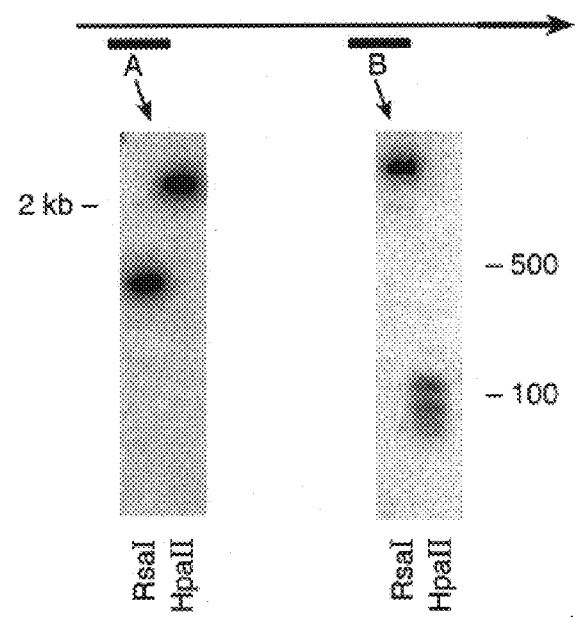
FIG._4
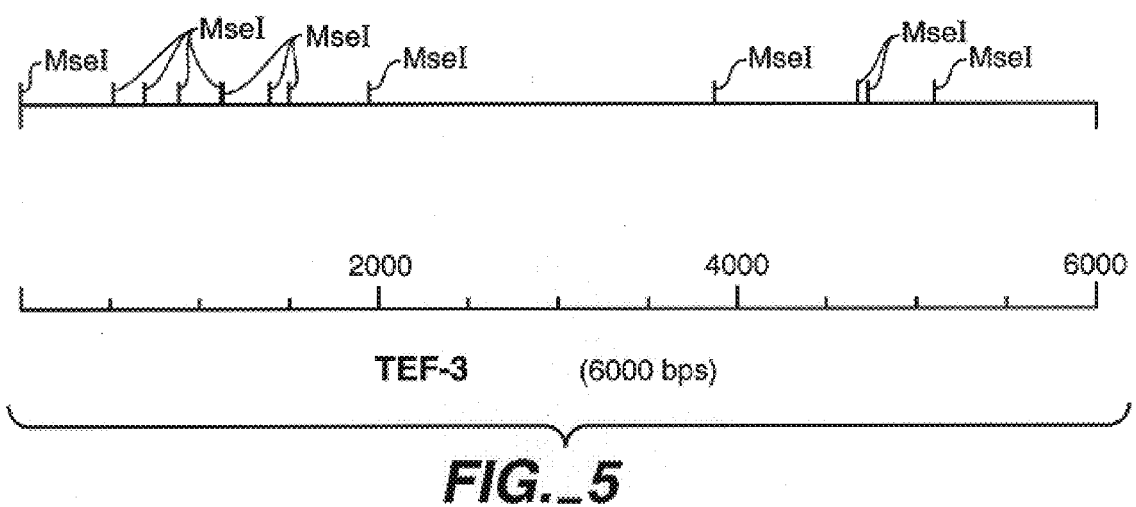
FIG._5

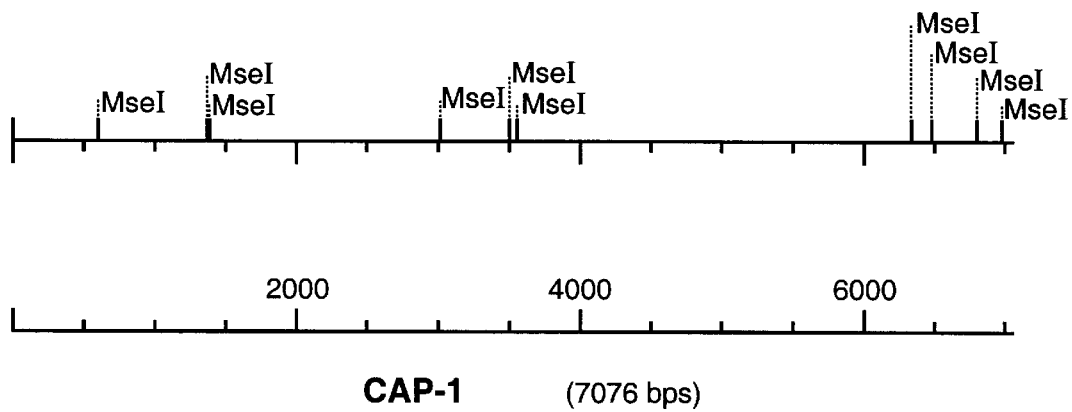
FIG._6
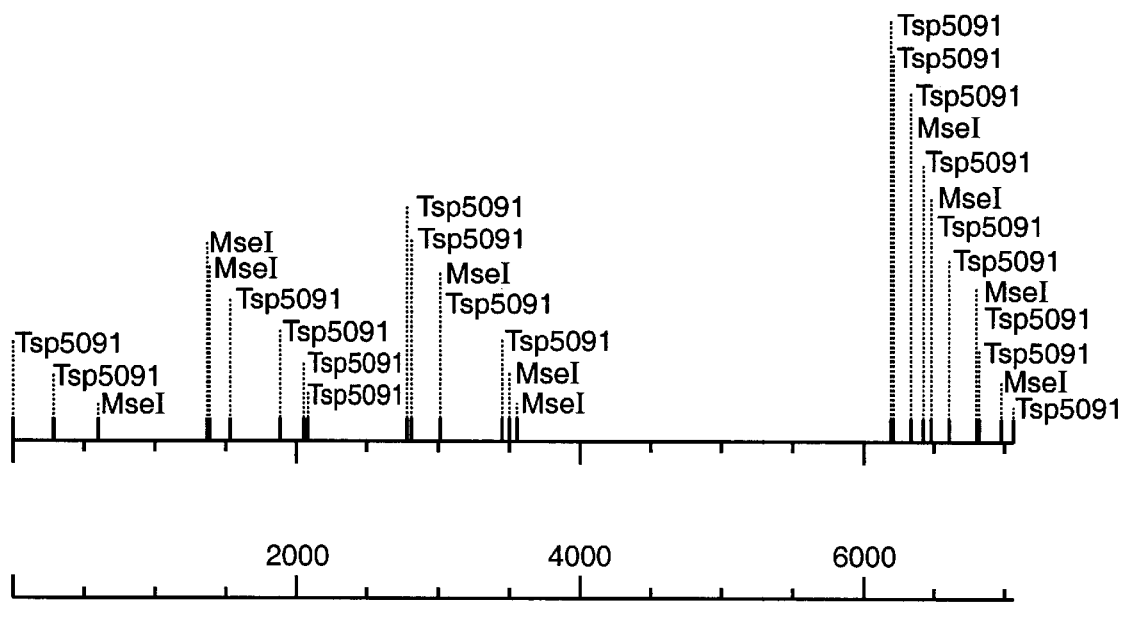
FIG._7

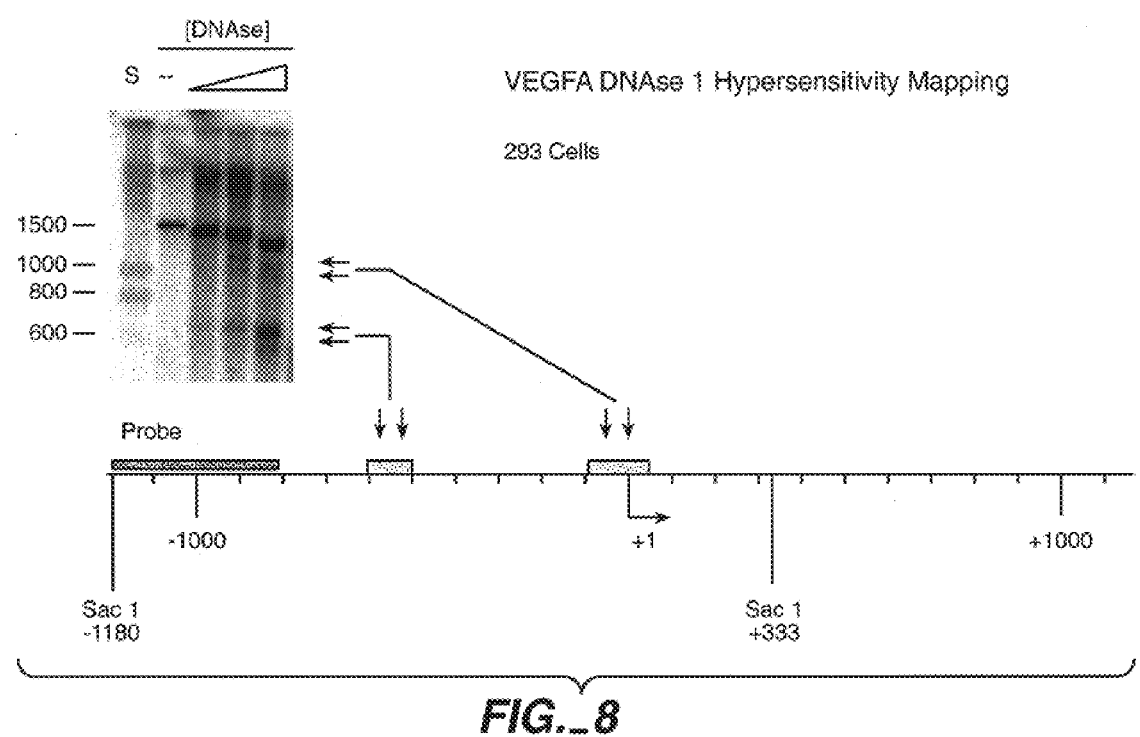
FIG._8

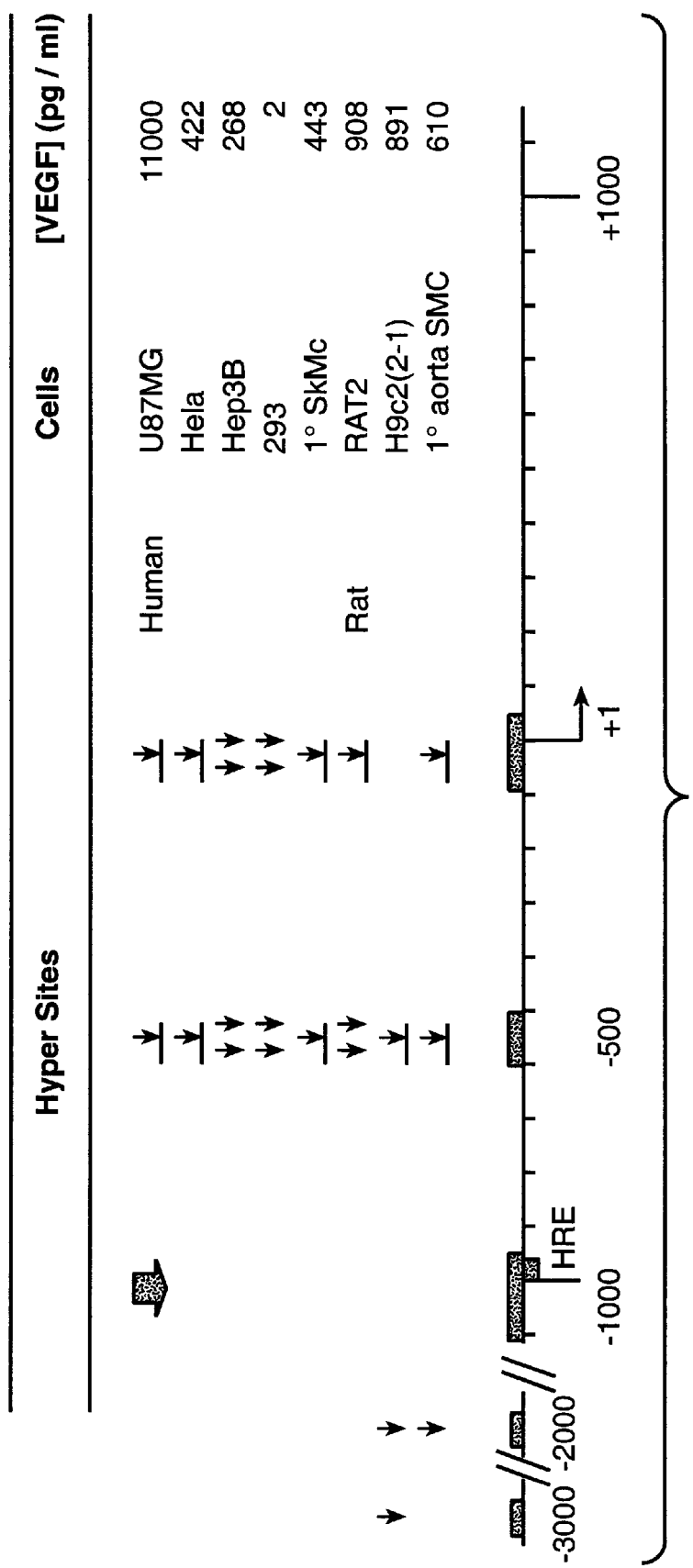
FIG._9

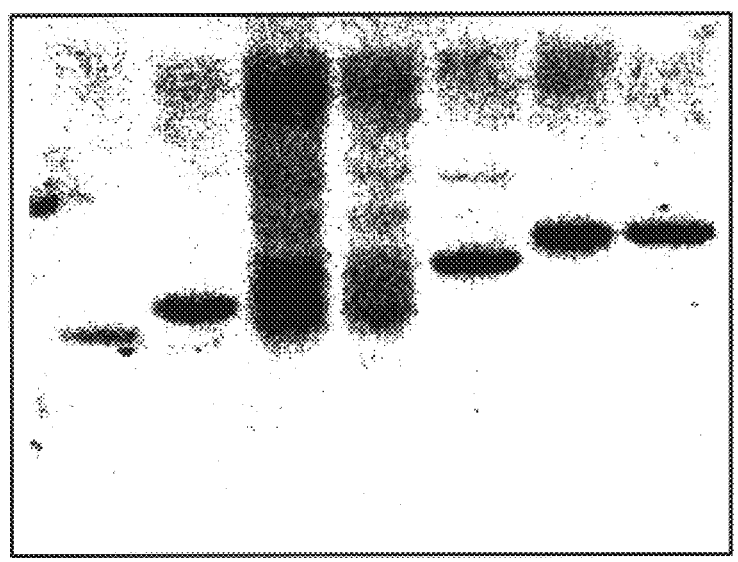
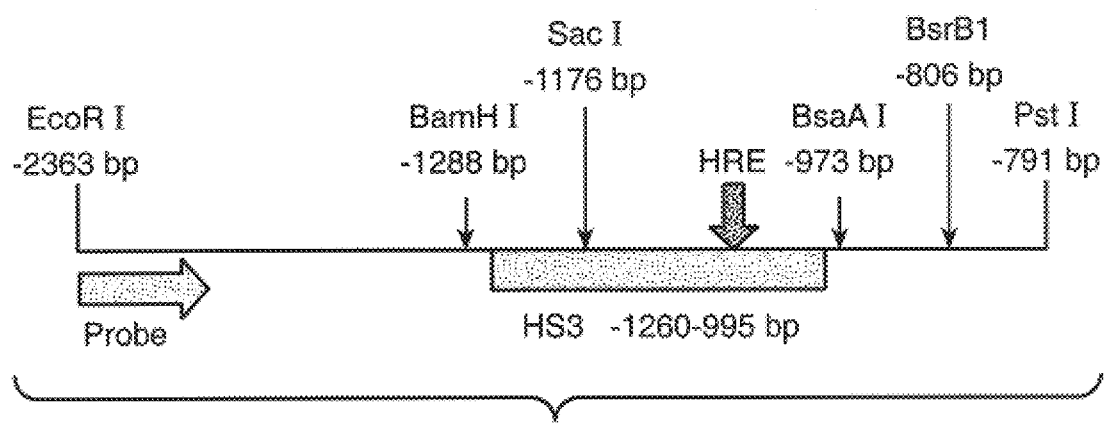
FIG._10

Conserved Regulatory Elements in the '-1000' Accessible Region:

Rat
-963  .ATC......... .AGAGACAGG....CTCTGTCTGC..CAGCTGTCTCTCCCTCAGGGCT

Human
-1062 CATCTGGGGTTGGGGGGCAGCAGGAACAAAGGGCCTCTGTCTGCCAGCTGCCTCCCTTTGGGTT

TH1-E4      AML1A      USF   HIF1a - EPAS1                AP-1
CTGCCAGACTCCACAGTGCATACGTGGGCTTCCACAGGTTCGTCTCTCCCT..CCGGCCACTGACTAACT  -853
TTGCCAGACTCCACAGTGCATACGTGGGCTCCAACAGGTTCCTCTCCCTTCCCCAGTCACTGACTAACC  -928

HRE   -1000   -500   +1   +1000

FIG._11

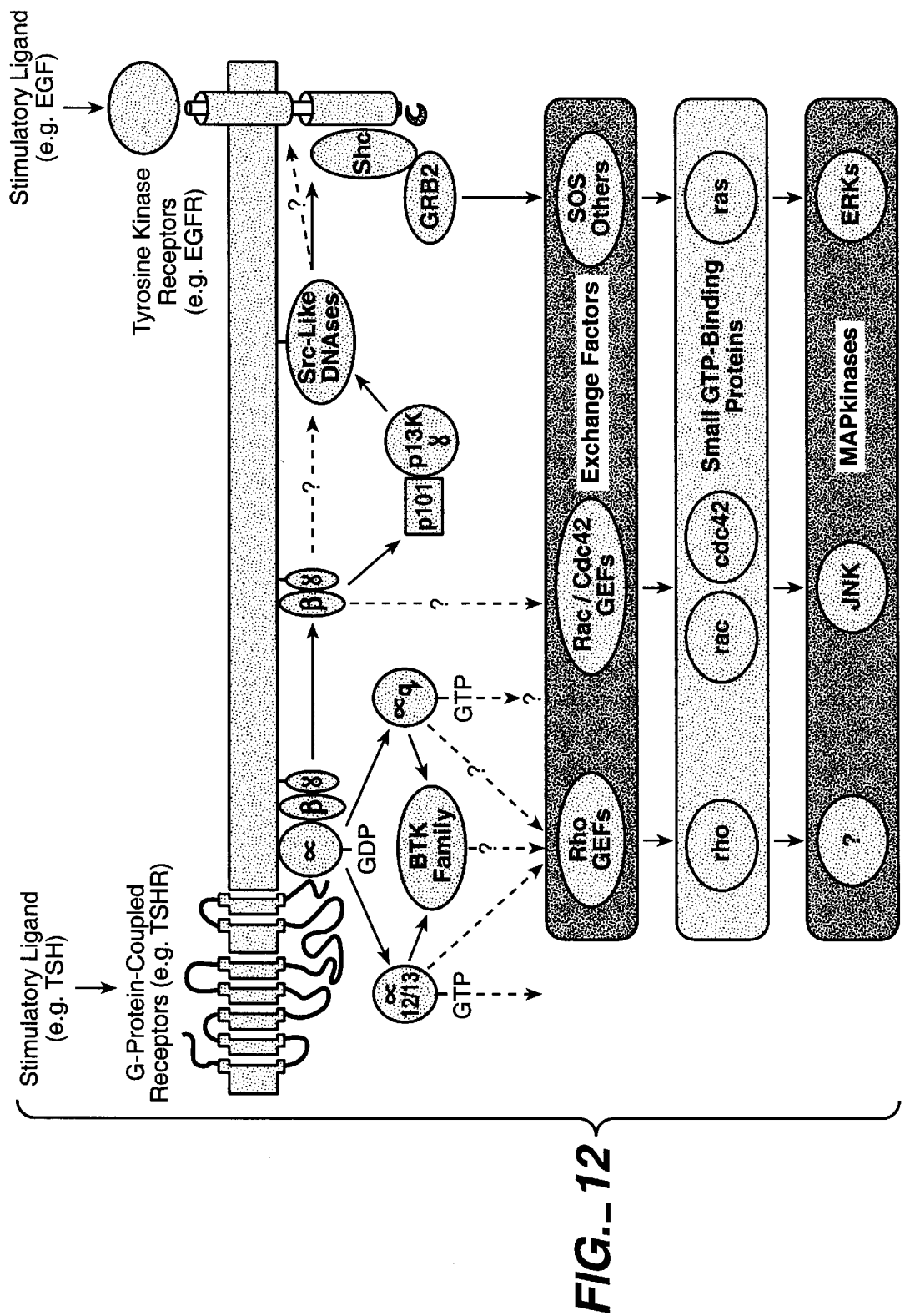
FIG._12

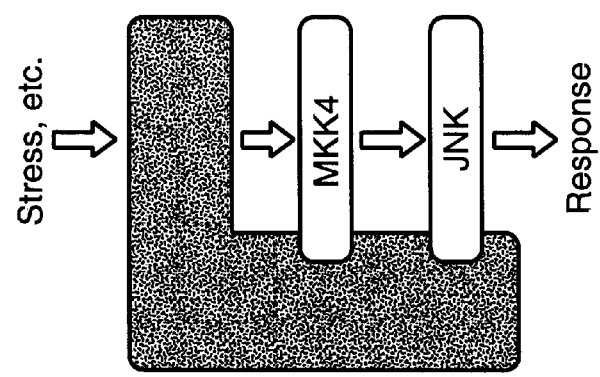
FIG._13C
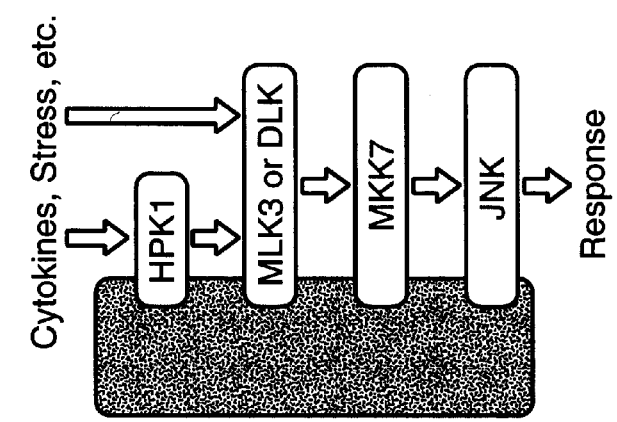
FIG._13B
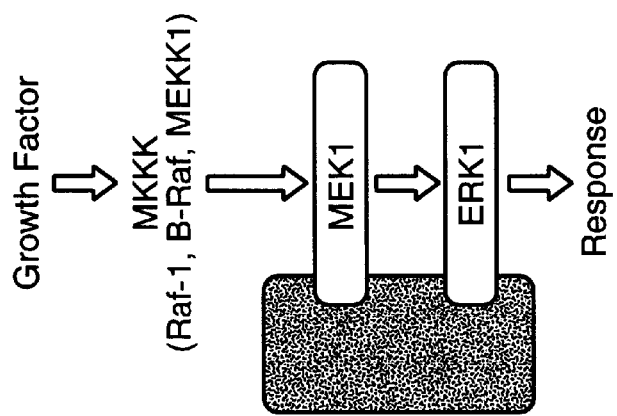
FIG._13A

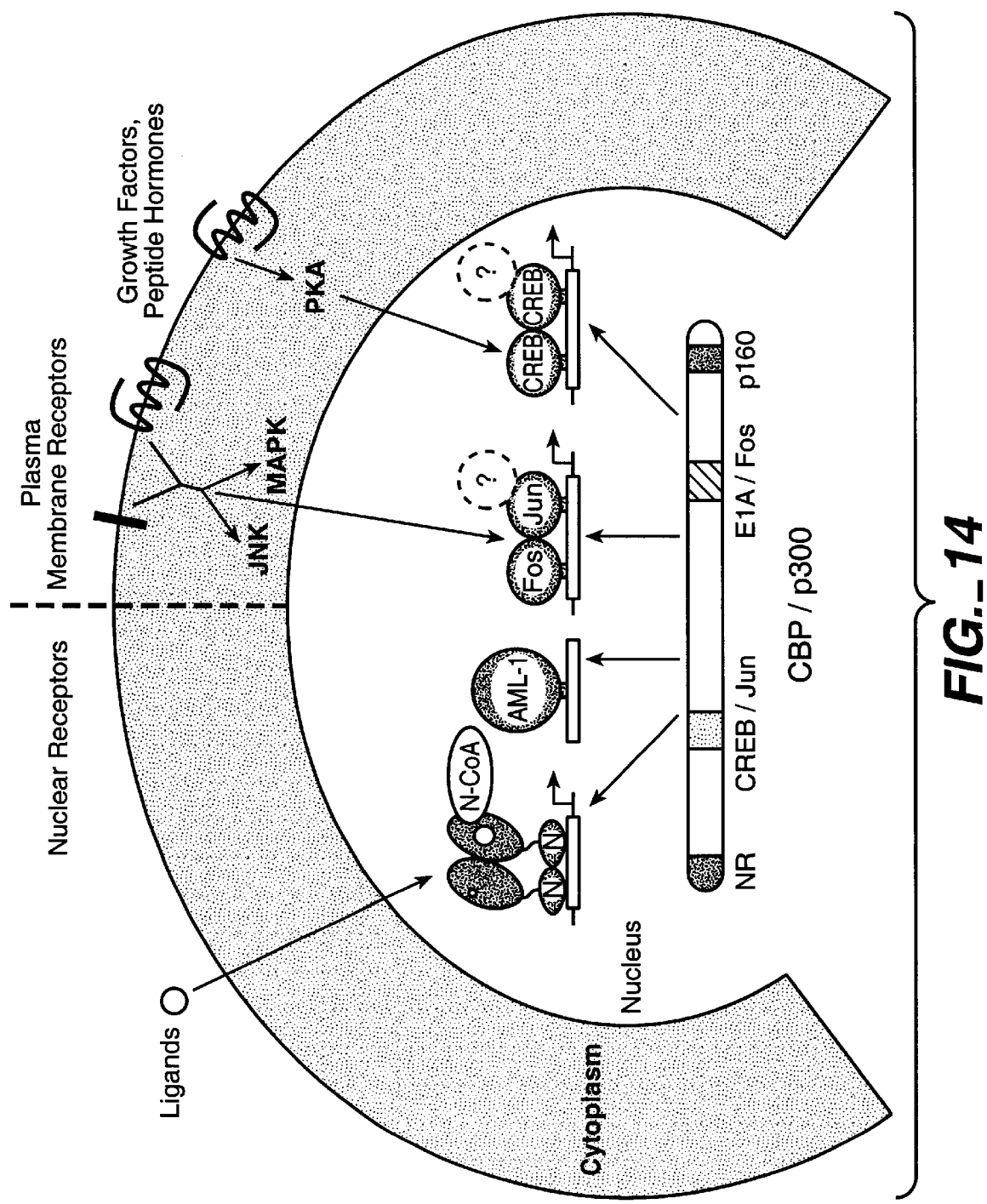
FIG._14

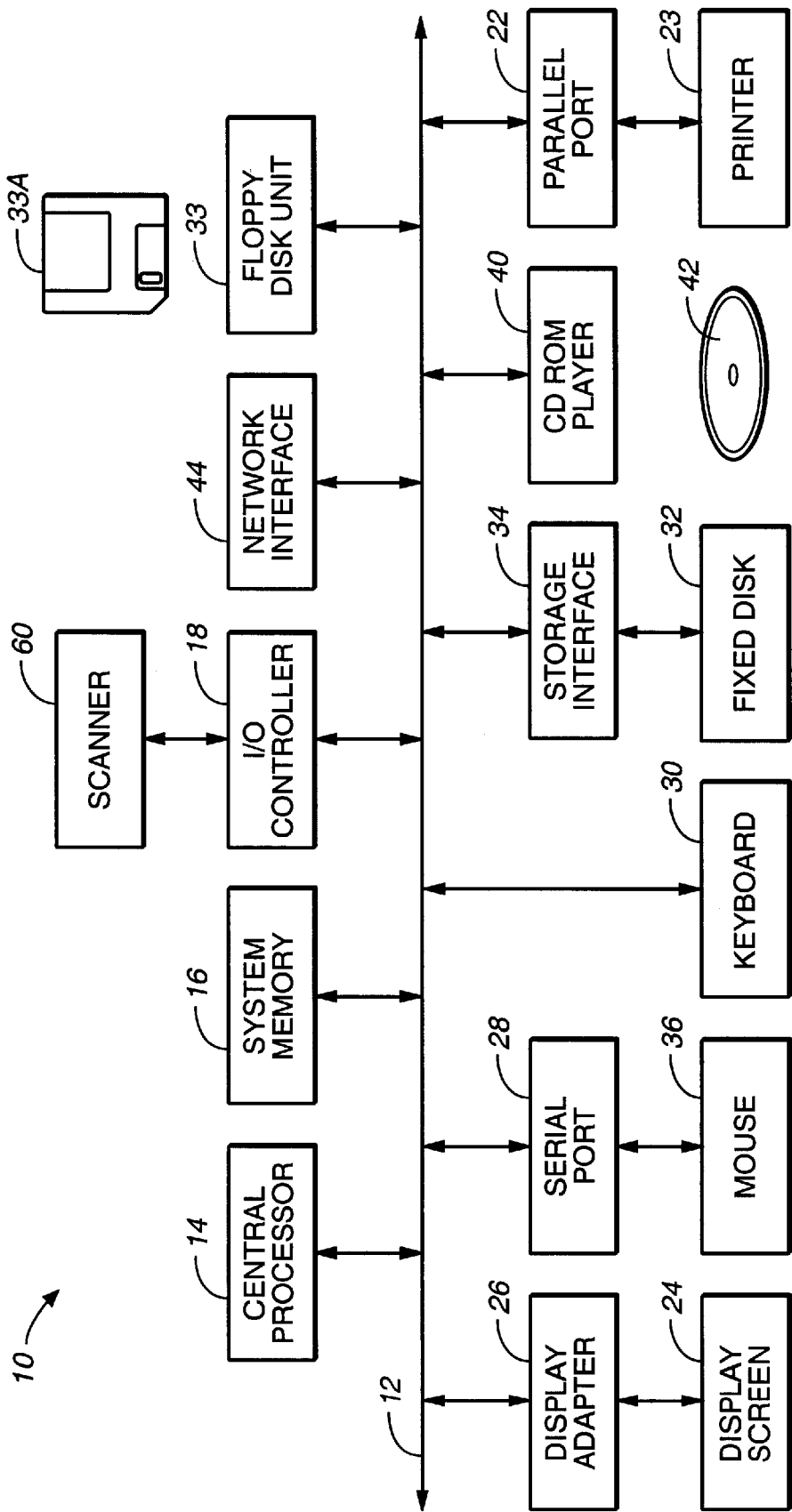
FIG._15

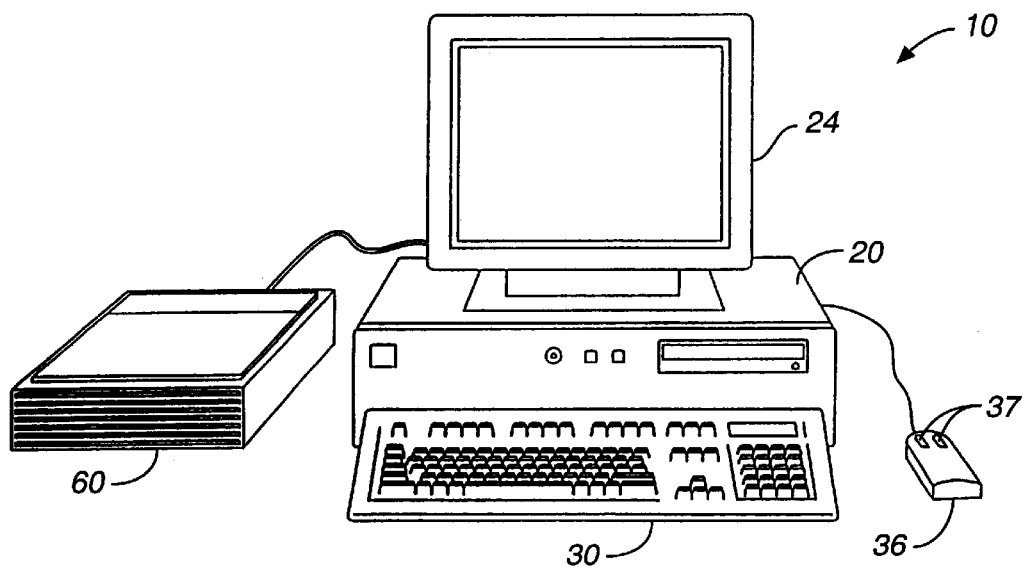
FIG._16
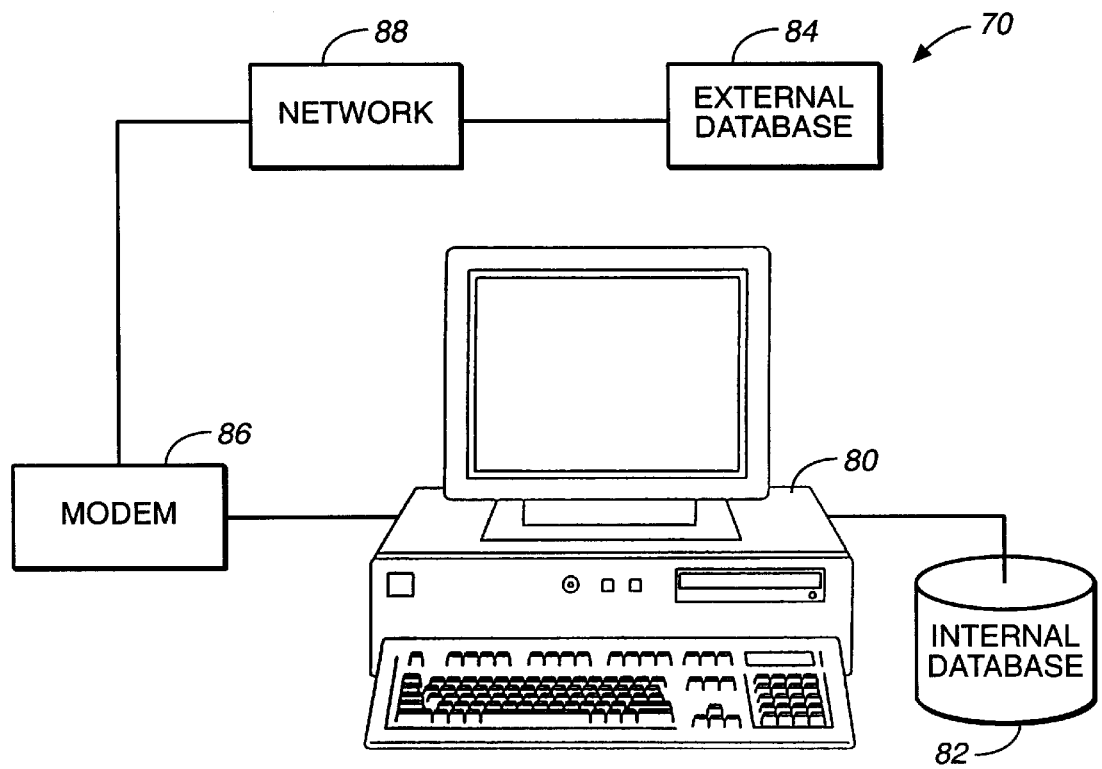
FIG._17

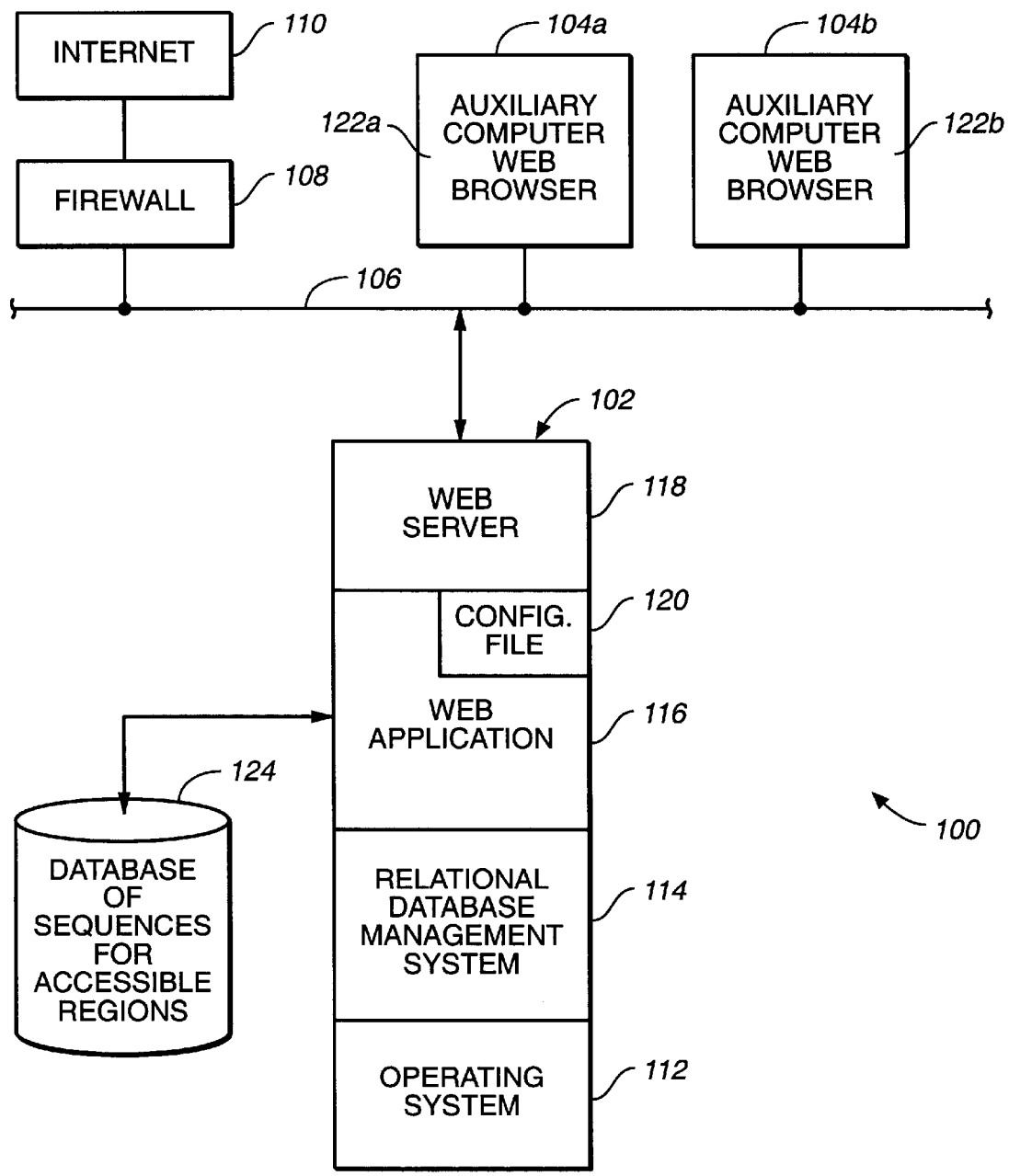
FIG._18

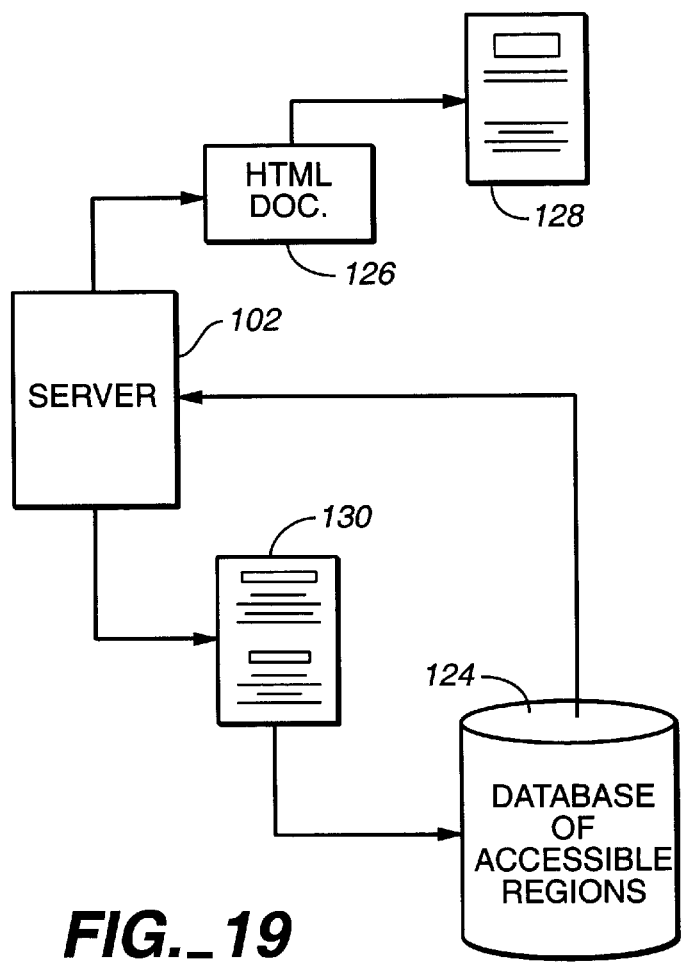
FIG._19
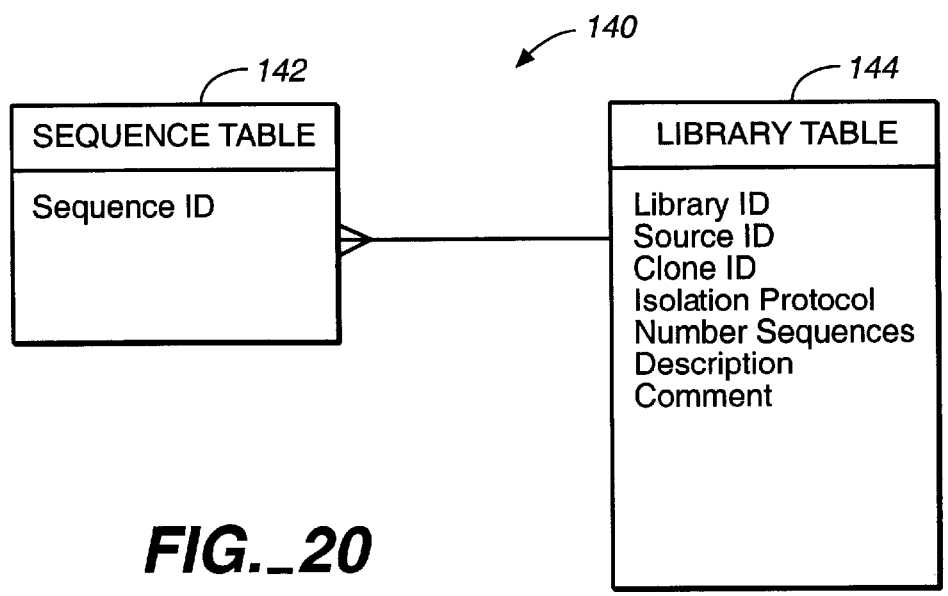
FIG._20

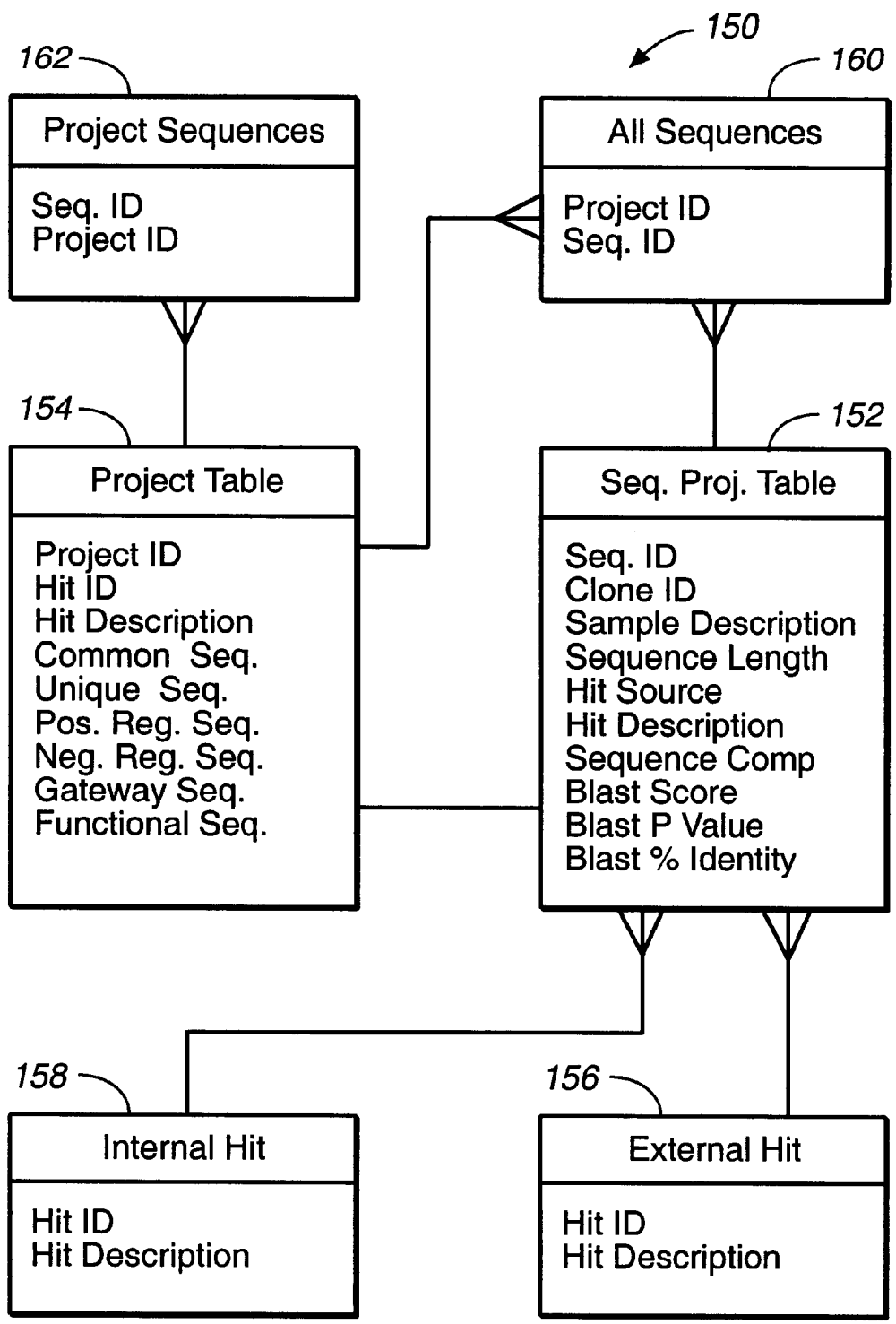
FIG._21

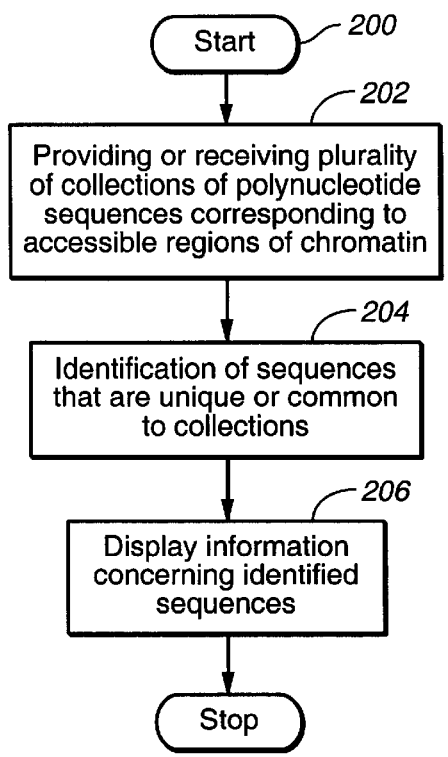
FIG._22
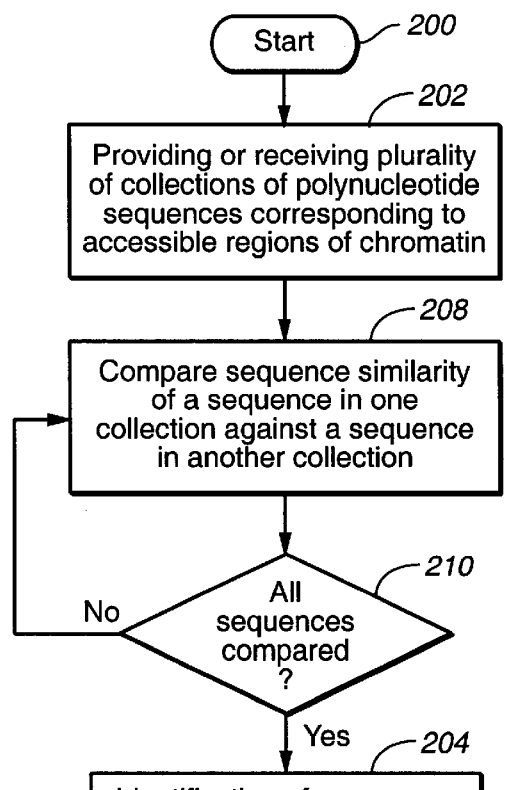
FIG._23
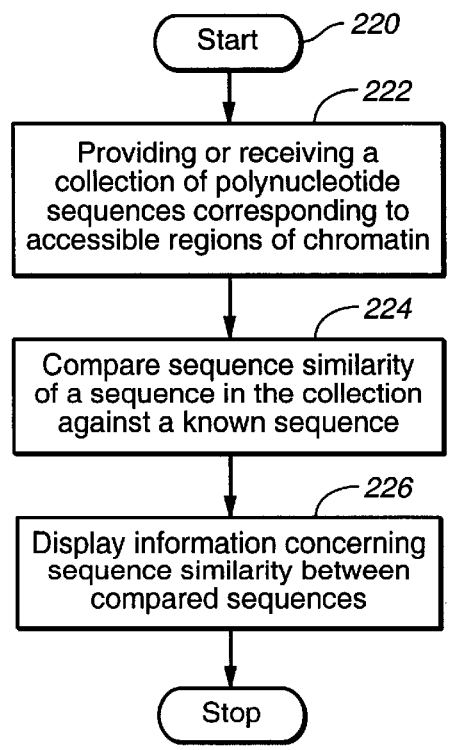
FIG._24

5'-HO-TAGAAGGCACAGTCGAGGACTTATCCTAGCCTCTGAATACTTTCAACAAGTTACACCCTT-P-3'-E (SEQ ID NO: 7)

3'-HO-AAAAAAAATCTTCCGTGTCAGCTCCTGAATAGGATCGGAGACTTATGAAAGTTGTTCAATGTGGGA-OH-5' (SEQ ID NO: 8)

FIG._25

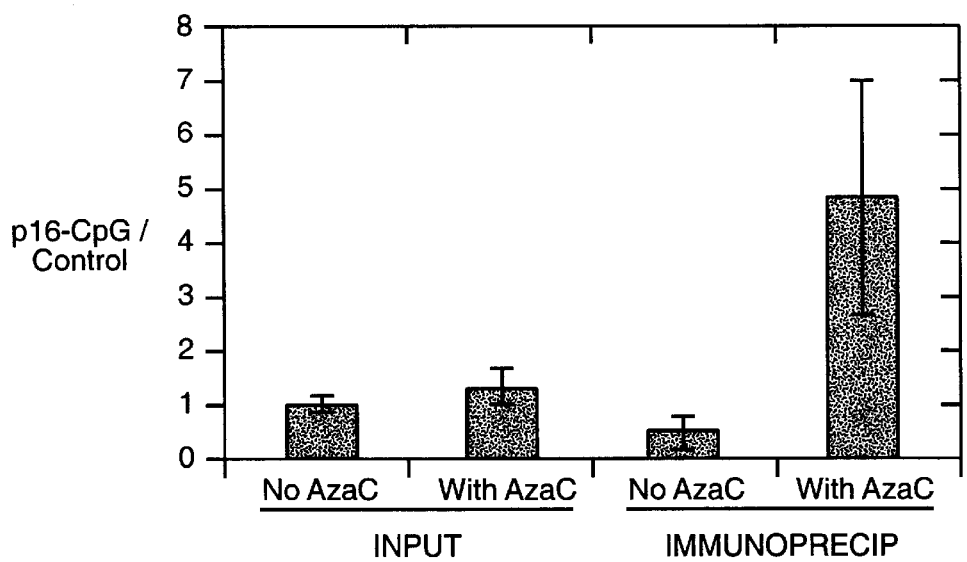
FIG._26
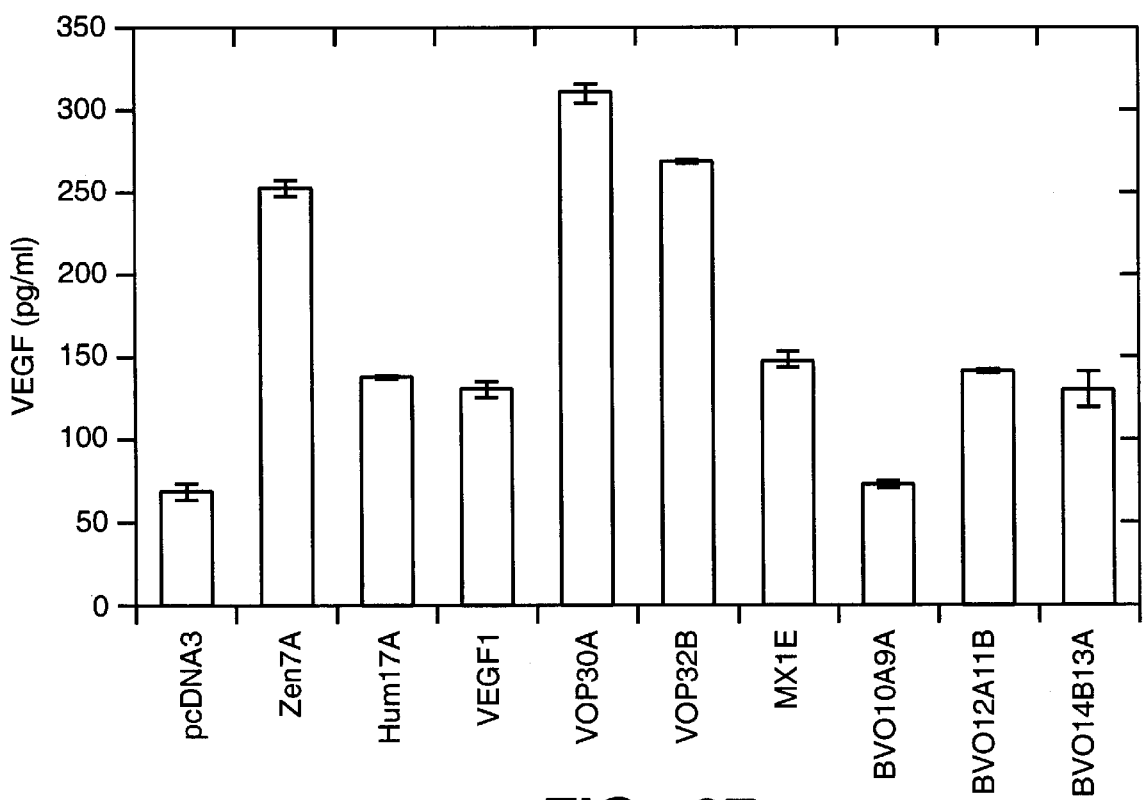
FIG._27

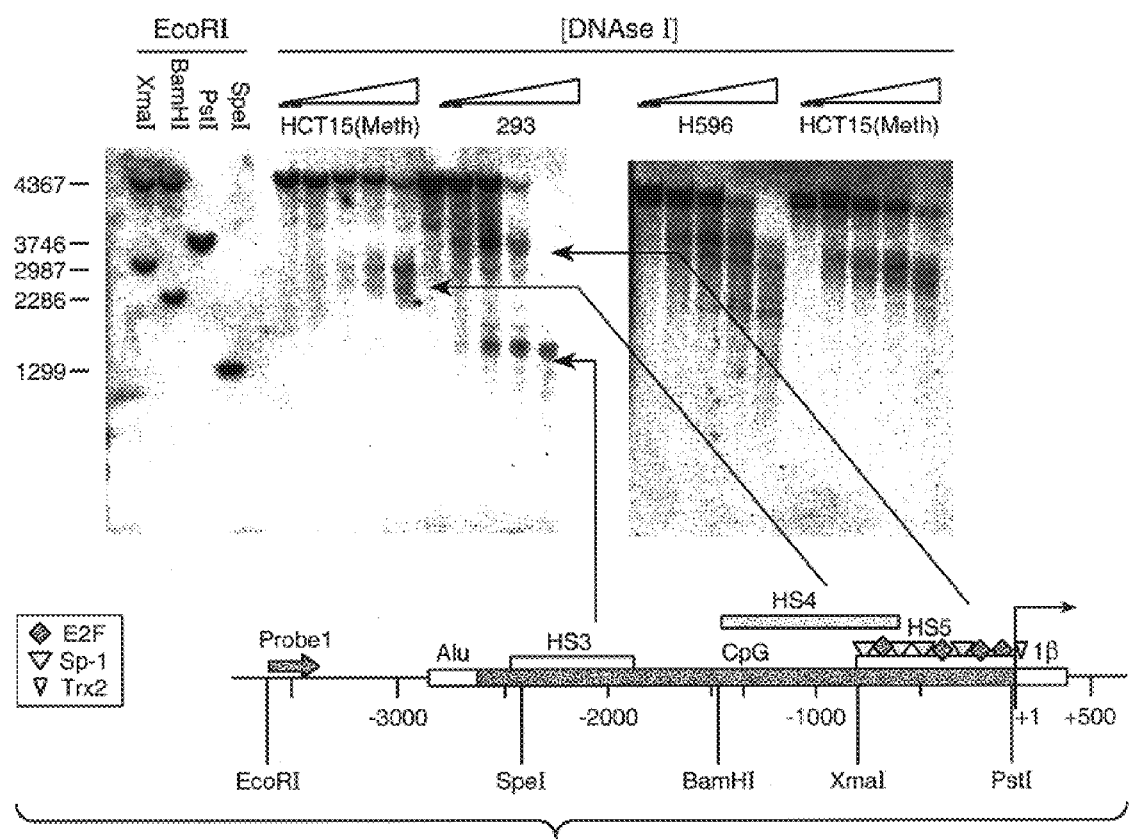
FIG._28

SEQUENCE LISTING

<160> NUMBER OF SEQ ID NOS: 24

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Kpn 1 target site

<400> SEQUENCE: 1 ggtacc                                                             6

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: adapter oligonucleotide

<400> SEQUENCE: 2
gcggtgaccc gggagatctg aattc                                        25

<210> SEQ ID NO 3
<211> LENGTH: 11
<212> TYPE: DNA

```
<213> ORGANISM: Artificial Sequence
<220> FEATURE:
<223> OTHER INFORMATION: Description of Artificial Sequence:  adapter
      oligonucleotide

<400> SEQUENCE: 3
ctagacttaa g                                                           11

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:  Bax
      gene-specific primer

<400> SEQUENCE: 4
gcccatcact gagaaatccc ttcc                                             24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:  adapter
      oligonucleotide

<400> SEQUENCE: 5
gcggtgaccc gggagatctg aattctt                                          27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:  adapter
      oligonucleotide

<400> SEQUENCE: 6
cgccactggg ccctctagac ttaag                                            25

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence:  adapter
      oligonucleotide

<400> SEQUENCE: 7
tagaaggcac agtcgaggac ttatcctagc ctctgaatac tttcaacaag ttacacccctt      60

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence:  adapter
      oligonucleotide

<400> SEQUENCE: 8
aaaaaaaatc ttccgtgtca gctcctgaat aggatcggag acttatgaaa gttgttcaat      60
gtggga                                                                 66

<210> SEQ ID NO 9
<211> LENGTH: 24
```

```
<212> TYPE: DNA
<213> ORGANISM: Artificial Sequence
<220> FEATURE:
<223> OTHER INFORMATION: Description of Artificial Sequence:
      adapter-specific primer

<400> SEQUENCE: 9
aggcacagtc gaggacttat ccta                                          24

<210> SEQ ID NO 10
<211> LENGTH: 122
<212> TYPE: DNA
<213> ORGANISM: Artificial Sequence
<220> FEATURE:
<223> OTHER INFORMATION: Description of Artificial Sequence:  insert
      sequence

<400> SEQUENCE: 10
ccggcctcgg tgttttcggc tttttcctgg cccccggccc gccaggccgg gccctctgct   60
gcccgctgaa tgggaggggg ggcggggtca cgtggcgggg ggaggggagg gccgtcgcga  120
tc                                                                 122

<210> SEQ ID NO 11
<211> LENGTH: 249
<212> TYPE: DNA
<213> ORGANISM: Artificial Sequence
<220> FEATURE:
<223> OTHER INFORMATION: Description of Artificial Sequence:  insert
      sequence

<400> SEQUENCE: 11
ccgggcgcca agggaagccg ggcgctgccc cctgctggcc aggttcgggc gcggcgccgc   60 ggagggcct cccctctctg gagagaattg aaggggtcc ggtgtggagc cccggctggc    120
tccgggctgg ggctgaccgg ctctgtgacc ttgggcaggt cactgcatct ctccaagcct  180
cagtttgcac gtctgtcaaa tagaggggca ttctctcact ttgcagggtc cctggaaata  240
agtgagatc                                                          249

<210> SEQ ID NO 12
<211> LENGTH: 1042
<212> TYPE: DNA
<213> ORGANISM: Artificial Sequence
<220> FEATURE:
<223> OTHER INFORMATION: Description of Artificial Sequence:  accessible
      region sequence

<400> SEQUENCE: 12
gatcggagtt cgagaccagc ccggccaact ggtgaaaccc tgtctctact aaaaaaatac   60
aaaaggagtt cgagaccagc ccggccaact ggtgaaaccc tgtctctact aaaaaaatac  120
aaaaattagc tgggtgtggt ggtgcacgcc tgtcatccca gctacttggg aggctgagat  180
aggaattagc tgggtgtggt ggtgcacgcc tgtcatccca gctacttggg aggctgagat  240
aggagaatcg cttgaaccca ggaggggagg cagaggttgc agtgagccga gatggcgcca  300
ctgtgaatcg cttgaaccca ggaggggagg cagaggttgc agtgagccga gatggcgcca  360
ctgtactccg gcctgggcaa gagcaagact ccaaccaaaa aaaaaaaaaa aaagaactag  420
cagtactccg gcctgggcaa gagcaagact ccaaccaaaa aaaaaaaaaa aaagaactag  480
cagtgcccag ggctgtacac caggtgccag tactggcagc aattcttcca gttattgtga  540
tagagcccag ggctgtacac caggtgccag tactggcagc aattcttcca gttattgtga  600
```

```
tagattctca tgacgctaaa atacccactt tgttatttaa cccttgctaa tccacaatga    660
gttgttctca tgacgctaaa atacccactt tgttatttaa cccttgctaa tccacaatga    720
gttgccaggt accagaatcc tttgttacta accagaccag gctgttcatt cttgaacagc    780
attgccaggt accagaatcc tttgttacta accagaccag gctgttcatt cttgaacagc    840
attgggcatc actttgtttt aataattctt gtatgagaag agcactcttt tccttctgat    900
agcaggcatc actttgtttt aataattctt gtatgagaag agcactcttt tccttctgat    960
agcaatgtgg ctccaactac tggctgatgt gagacggtac cggatgtggc tccaactact   1020
ggctgatgtg agacggtacc gg                                            1042
```

```
<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: adapter
      oligonucleotide containing a Sau 3AI-compatible
      end

<400> SEQUENCE: 13
gatcgaattc ag                                                         12

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence: adapter
      oligonucleotide containing a Sau 3AI-compatible
      end

<400> SEQUENCE: 14 cttaagtc                                                               8

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: p16 forward
      primer

<400> SEQUENCE: 15
aatagcacct cctccgagca                                                 20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: p16 reverse
      primer

<400> SEQUENCE: 16
ccctgtccct caaatcctct g                                               21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: p16 probe

<400> SEQUENCE: 17
```
acagcgtccc cttgcctgga aag                                                    23

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Control
      forward primer

<400> SEQUENCE: 18
gccccagagg gaaacacaa                                                         19

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Control
      reverse primer

<400> SEQUENCE: 19
cccccacccc cataagc                                                           17

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Control probe

<400> SEQUENCE: 20
cctccatggt ggtacccagc aagg                                                   24

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: EPAS
      amplifier primer

<400> SEQUENCE: 21
ggatccggcc accgcggccg cacgcccaat agccctgaag actattac                         48

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: EPAS
      amplifier primer

<400> SEQUENCE: 22
atgaattcgc ggccgcccca ctgggtattg gatctgcccc ccat                             44

<210> SEQ ID NO 23
<211> LENGTH: 109
<212> TYPE: DNA
<213> ORGANISM: Artificial Sequence
<220> FEATURE:
<223> OTHER INFORMATION: Description of Artificial Sequence: human VEGF
      accessible region

<400> SEQUENCE: 23
atcagagaca ggctctgtct gccagctgtc tctccctcag ggctctgcca gactccacag            60

```
tgcatacgtg ggcttccaca ggtcgtctcc ctccggccac tgactaact          109
```

<210> SEQ ID NO 24
<211> LENGTH: 134
<212> TYPE: DNA
<213> ORGANISM: Artificial Sequence
<220> FEATURE:
<223> OTHER INFORMATION: Description of Artificial Sequence:  human VEGF
      accessible region

<400> SEQUENCE: 24

```
catctggggt tgggggggca gcaggaacaa gggcctctgt ctgcccagct gcctccccct    60
ttgggttttg ccagactcca cagtgcatac gtgggctcca acaggtcctc ttccctccca   120
gtcactgact aacc                                                    134
```

PHARMACOGENOMICS AND IDENTIFICATION OF DRUG TARGETS BY RECONSTRUCTION OF SIGNAL TRANSDUCTION PATHWAYS BASED ON SEQUENCES OF ACCESSIBLE REGIONS

CROSS-REFERENCE TO RELATED APPLICATIONS

This application claims priority under the provisions of 35 U.S.C. §119 to U.S. Provisional Patent Application Ser. No. 60/200,590, filed Apr. 28, 2000; U.S. Provisional Patent Application Ser. No. 60/214,674, filed Jun. 27, 2000; and U.S. Provisional Patent Application Ser. No. 60/228,608, filed Aug. 28, 2000; the disclosures of which are hereby incorporated by reference in their entireties.

TECHNICAL FIELD

The present disclosure relates to the fields of pharmacogenomics, signal transduction, bioinformatics, gene regulation, gene regulatory sequences, gene regulatory proteins and methods of determining gene regulatory pathways.

BACKGROUND

Worldwide genome sequencing efforts are providing a wealth of information on the sequence and structure of various genomes, and on the locations of thousands of genes. In addition, genome research is yielding a considerable amount of information on gene products and their functions. The next challenges will be in the understanding and interpretation of genomic information. A major limitation in the analysis of genome sequence information to date is the lack of information that has been extracted from genome sequences on the location, extent, nature and function of sequences that regulate gene expression, i.e., gene regulatory sequences.

The cis-acting sequence elements that participate in the regulation of a single metazoan gene can be distributed over 100 kilobase pairs or more. Combinatorial utilization of regulatory elements allows considerable flexibility in the timing, extent and location of gene expression. The separation of regulatory elements by large linear distances of DNA sequence facilitates separation of functions, allowing each element to act individually or in combination with other regulatory elements. Non-contiguous regulatory elements can act in concert by, for example, looping out of intervening chromatin, to bring them into proximity, or by recruitment of enzymatic complexes that translocate along chromatin from one element to another. Determining the sequence content of these cis-acting regulatory elements offers tremendous insight into the nature and actions of the trans-acting factors which control gene expression, but is made difficult by the large distances by which they are separated from each other and from the genes which they regulate.

In order to address the problems associated with collecting, processing and analyzing the vast amounts of sequence data being generated by, e.g., genome sequencing projects, various bioinformatic techniques have been developed. In general, bioinformatics refers to the systematic development and application of information technologies and data processing techniques for collecting, searching, analyzing and displaying data obtained by experiments to make observations concerning biological processes.

One example of such an analysis involves the determination of sequences corresponding to expressed genes (expressed sequence tags, or ESTs) and computerized analysis of a genome sequences by comparison to databases of expressed sequence tags. However, this type of analysis provides information on coding regions only and thus does not assist in the identification of regulatory sequences. Mapping of a particular EST onto a genome sequence and searching the region upstream of the EST for potential regulatory sequences is also ineffective, for several reasons. First, large introns and/or 5' untranslated regions can separate an EST sequence from its upstream regulatory regions; therefore the genomic region to be searched for regulatory sequences is not clearly defined. Second, searches of a given region of a genome for sequences homologous to transcription factor binding sites will yield numerous "hits" (representing potential regulatory sequences), some of which are functional in a given cell and some of which are not. Thus, such searches will fail to provide unambiguous information as to which of several potential regulatory sequences are active in the regulation of expression of a given gene in a particular cell. Furthermore, it is likely that, with respect to a particular gene, different regulatory regions are functional in different cell types. Therefore, the problem of identifying regulatory sequences for a gene is specific to each cell type in which the gene is (or is not) expressed. Indeed, different regulatory sequences will often be responsible for regulating the expression of a particular gene in different cells.

Thus, the informational content of a gene does not depend solely on its coding sequence (a portion of which is represented in an EST), but also on cis-acting regulatory elements, present both within and flanking the coding sequences. These include promoters, enhancers, silencers, locus control regions, boundary elements and matrix attachment regions, all of which contribute to the quantitative level of expression, as well as the tissue- and developmental-specificity of expression of a gene. Furthermore, the aforementioned regulatory elements can also influence selection of transcription start sites, splice sites and termination sites.

Identification of cis-acting regulatory elements has traditionally been carried out by identifying a gene of interest, then conducting an analysis of the gene and its flanking sequences. Typically, one obtains a clone of the gene and its flanking regions, and performs assays for production of a gene product (either the natural product or the product of a reporter gene whose expression is presumably under the control of the regulatory sequences of the gene of interest). Here again, one encounters the problem that the extent of sequences to be analyzed for regulatory content is not concretely defined, since sequences involved in the regulation of metazoan genes can occupy up to 100 kb of DNA. Furthermore, assays for gene products are often tedious and reporter gene assays are often unable to distinguish transcriptional from translations regulation and can therefore be misleading.

Pelling et al. (2000) Genome Res. 10:874–886 disclose a library of transcriptionally active sequences, derived by cloning chromosomal sequences that are immunoprecipitated by antibodies to hyperacetylated histone H4. This library comprises primarily coding sequences and sequences proximal to the transcription startsite. It does not disclose methods for identifying regulatory sequences, databases of regulatory sequences or uses for databases of regulatory sequences.

It can thus be seen that a major limitation of current comparative genomics and bioinformatic analyses is that they are unable to identify cell-specific regulatory sequences. In light of these limitations, methods for identifying regulatory DNA sequences (particularly in a high-throughput fashion), libraries of regulatory sequences, and databases of regulatory sequences would considerably advance the fields of genomics and bioinformatics.

SUMMARY

Disclosed herein are compositions and methods useful in a wide variety of applications, including, but not limited to, (1) identifying a drug that affects accessible regions of cellular chromatin; (2) elucidating signal transduction pathways; (3) facilitating modulation of signal transduction pathways and/or facilitating modulation of the gene(s) associated with the signal transduction pathway; and (4) pharmacogenomically selecting an appropriate drug therapy. Thus, these compositions and methods are useful for facilitating drug discovery and testing.

Accordingly, in one aspect, provided herein are methods for identifying a drug that affects accessible regions of cellular chromatin relative to a gene of interest, the method comprising: (a) providing cellular chromatin having known accessible regions; (b) exposing the cellular chromatin of step (a) to the drug under conditions that allow the drug to affect cellular chromatin; and (c) comparing the nature of accessible regions of the cellular chromatin of step (b) with the accessible regions of the cellular chromatin of step (a) to determine the effect, if any, of the drug on the accessible regions of the cellular chromatin. In certain embodiments, step (c) comprises reacting the cellular chromatin with an antibody against acetylated or phosphorylated histones. In other embodiments, step (c) comprises mapping accessible regions of cellular chromatin, for example by (a) reacting cellular chromatin with a chemical or an enzymatic probe to generate chromatin-associated DNA fragments, wherein the DNA fragments comprise, at their termini, sites of probe reaction and identify accessible regions of cellular chromatin; (b) optionally treating the DNA fragments to obtain blunt ends; (c) ligating an adapter polynucleotide to at least one end of the DNA fragments to generate adapter-ligated fragments; (d) amplifying the adapter-ligated fragments in the presence of a first primer that is complementary to the adapter and a second primer that is complementary to a segment of the gene of interest to form an amplified product, wherein the size of the amplified product is a measure of the distance from the segment of the gene to which the second primer binds and the site of probe reaction. The probe can be, for example, an enzymatic probe (e.g., nuclease such as DNAseI or micrococcal nuclease) or a chemical probe. The drug can be, for example, a protein or a small molecule. In certain embodiments, the accessible regions are provided as a collection of polynucleotides (e.g., a library).

In other aspects, methods for identifying a drug target are provided. The methods comprise (a) identifying an accessible region in cellular chromatin related to a gene of interest; (b) examining the sequence of the accessible region to identify one or more binding sites for a transcriptional regulatory molecule; and (c) identifying one or more members of a signal transduction pathway that regulate the activity of the transcriptional regulatory molecule; wherein the member of the signal transduction pathway identified in step (c) comprises the drug target. The accessible region can be identified by any method, for example, by DNAse hypersensitivity. The signal transduction pathway can include, for example, a G-protein-coupled receptor. The cellular chromatin may be derived from any suitable cell, for example, a human cell, an animal cell, a plant cell or a microorganism (e.g., a human, animal or plant pathogen) and may be provided, for example, as a collection of polynucleotides representing accessible regions. The drug target can comprise a nucleotide sequence or a protein or amino acid sequence.

In still further embodiments, the methods comprise adding a molecule (e.g., a protein or small molecule) that affects the expression of the gene via affecting the member of the signal transduction pathway identified by the methods described herein. The gene may be involved in a disease state or condition, for example cancer, osteoporosis or cardiovascular disease. In some embodiments, the molecule can augment expression of the gene, for example to increase production of a protein product; increasing expression of genes involved in cell growth; or increasing expression of a gene involved in resistance or clearing pathogens in a host (e.g., animal, human or plant host). In yet other embodiments, the molecule inhibits expression of the gene, for example inhibiting a gene involved in cell growth; inhibiting genes expressed by diseased (e.g., cancerous) cells; or inhibiting a gene in a pathogenic organism involved in toxicity, infectivity or pathogenicity.

Also provided herein are methods for modulating a signal transduction pathway involved in regulation of a gene of interest. The methods comprise (a) identifying a member of the signal transduction pathway involved in regulation of a gene by the methods described herein; and (b) adding a molecule which modulates the activity of the member of the signal transduction pathway identified in step (a). In certain embodiments, the modulation of the selected member of the signal transduction pathway facilities processes selected from the group consisting of tissue engineering, transplantation, response to a pathogen, inhibition of cell growth, activation of cell growth and apoptosis. In some embodiments, the signal transduction pathway is present in human or animal cells, and is involved, for example, in growth, production of chemicals or biochemicals, response to pathogens, disease states or conditions such as cancer, cardiovascular disease, neurodegenerative diseases or osteoporosis. In other embodiments the signal transduction pathway is present in plant cells and is involved, for example, in herbicide response, pathogen response, growth, yield, biochemical properties or composition (e.g., oil composition); and/or production of chemicals or biochemicals. In still further embodiments the signal transduction pathway is present in microorganisms, and is involved, for example, in production of a chemical, biochemical, protein or pharmaceutical or in pathogenicity (e.g., replication or toxicity).

In still further aspects, methods for pharmacogenomically selecting an appropriate drug therapy to administer to a first individual having a disease or condition are provided. The methods comprise (a) determining the location and nature of the regulatory accessible regions associated with drug response in the first individual; and (b) correlating the location and nature of the regulatory accessible regions associated with drug response in the first individual to known locations and natures of regulatory accessible regions associated with drug response, thereby selecting an appropriate drug therapy to be administered to the first individual. In certain embodiments, the regulatory accessible regions examined are associated with genes involved in drug metabolism, for example cytochrome P450, N-acetyltransferase, NAD(p)H quinone oxidoreductase, thiopurine methyltransferase, beta$_2$-adrenergic receptor, dopamine D3 receptor, MDR-1 (Multiple drug resistance-1 gene), and MRPs (Multiple drug resistance proteins). Disease states or conditions that will benefit from these methods include, but are not limited to, chronic illness in which individuals will need medication for an extended period (e.g., cardiovascular disease, cystic fibrosis, etc.); conditions such as osteoporosis, neurodegenerative diseases, and cancer in which inappropriate therapy can cause irreversible changes; conditions for which known drug treatments are sometimes associated with allergy or sensitivity.

These and other embodiments will readily occur to those of ordinary skill in the art in view of the disclosure herein.

BRIEF DESCRIPTION OF THE DRAWINGS

FIG. 1 shows a schematic drawing of a typical eukaryotic gene and indicates exemplary regulatory elements that are commonly found in association with eukaryotic genes. Not every regulatory region shown here will necessarily be associated with all genes, and not every potential type of regulatory region is shown. The drawing is not to scale and the relative locations of individual regulatory elements may differ from those shown in the figure. BE=boundary element (also known as an "insulator"); LCR=locus control region; 5' UTR=5' untranslated region; pA=polyadenylation signal; Term=transcription termination site; MAR=(nuclear) matrix attachment region; Ori=replication origin.

FIGS. 2A–B show an analysis of DNase hypersensitive sites in the human erythropoietin gene in 293 cells. FIG. 2A shows a schematic diagram of the structure of the gene, indicating the transcriptional start site (rightward-pointing arrow), the transcription termination site (pA), and the locations of Xba I sites which define the DNA fragment used for mapping. Shown below the line are the location of the probe (a $^{32}$P-labeled Xba I-Kpn I fragment, hatched box) and the locations of two DNase hypersensitive sites (upward-pointing arrows). FIG. 2B shows a phosphorimager® image of a 1% agarose gel. Locations of the positions of migration of the XbaI fragment (10.5 kb) and the two fragments defined by the DNase hypersensitive sites (3.9 kb and 3.3 kb) are shown to the right of the gel image.

FIG. 3 shows a comparison of the relative sensitivity of bulk human genomic DNA to various restriction endonucleases. Total human genomic DNA (5 µg per lane) was digested to completion with the indicated restriction enzyme and resolved on a 2% agarose gel alongside 1 kb (lane 1) or 100 bp (lane 5) size markers. The gel was stained with ethidium bromide and photographed under ultraviolet transillumination. The doublet in lane 5 corresponds to 500 bp.

FIG. 4 shows analysis of a mammalian genomic DNA insert by digestion with Rsa I and Hpa II, blotting of fractionated digestion products and hybridization with probes corresponding to either known regulatory regions or non-regulatory DNA. Lane 1: Rsa I digest, non-regulatory region probe; Lane 2: Hpa II digest, non-regulatory region probe; Lane 3: Rsa I digest, regulatory region probe; Lane 4: Hpa II digest, regulatory region probe.

FIG. 5 is a schematic diagram of a portion of the human TEF-3 gene, showing the locations of recognition sites for the restriction enzyme Mse I.

FIG. 6 is a schematic diagram of a portion of the human CAP-1 gene, showing the locations of recognition sites for the restriction enzyme Mse I.

FIG. 7 is a schematic diagram of a portion of the human CAP-1 gene, showing the locations of recognition sites for the restriction enzymes Mse I and Tsp509 I.

FIG. 8 shows an analysis of DNase hypersensitive regions upstream of the vascular endothelial growth factor (VEGF) gene analyzed in human 293 cells.

FIG. 9 summarizes DNase hypersensitive site analyses of the VEGF gene in a number of different cells and provides information on the level of VEGF expression in each of the cell types. Locations of DNase hypersensitive sites are indicated by downward-pointing arrows.

FIG. 10 shows a detailed mapping of the DNase I hypersensitive region located around −1,000 in the VEGF gene in U87MG cells. Nuclei from U87MG were treated with DNase I, and nuclear DNA was purified, digested with Eco RI, fractionated by gel electrophoresis and blotted. Analysis with two different DNase I concentrations is shown. Additional lanes contain DNA from nuclei that were not treated with DNase, but were subjected to double restriction digestions with Eco RI and Bam HI, Sac I, Bsa I, Bsr BI or Pst I, as indicated above. The lower part of the figure shows a schematic diagram of a portion of the VEGF gene, indicating the location of restriction enzyme recognition sites, and the extent of the hypersensitive region. See examples 1, 2 and 5 for details.

FIG. 11 (SEQ ID NOS:23 and 24) shows the nucleotide sequence of the accessible region located around 1,000 base pairs upstream of the transcriptional startsite of the human VEGF gene. Target sites for various transcription factors are indicated. Sequences of the murine and human VEGFA genes in this region are shown.

FIG. 12 is a schematic diagram depicting signal transduction pathways which target, for example, kinases such as c-Jun N-terminal kinase (JNK) and extracellular-regulated kinases (ERKs).

FIGS. 13A–C are schematic diagrams depicting various scaffold proteins and molecules which may bind to these proteins.

FIG. 14 is a schematic diagram depicting cellular localization of proteins and nucleotides involved in various signal transduction pathways.

FIGS. 15 and 16 depict certain aspects of computer systems for implementing certain of the methods disclosed herein.

FIG. 17 is a schematic representation of a networked computer system that can be utilized to implement certain of the methods disclosed herein.

FIG. 18 is a schematic representation of a server-based intranet or Internet system for providing database services in accordance with certain aspects of the present disclosure or for conducting certain of the methods disclosed herein.

FIG. 19 is a schematic representation of certain elements including software entities that can be utilized with a server-based computer system to provide information in response to user queries regarding polynucleotide sequences that correspond to accessible regions.

FIGS. 20 and 21 are data models for specific relational databases that store polynucleotide sequences in accordance with certain embodiments of the methods disclosed herein.

FIGS. 22, 23 and 24 are flowcharts that depict certain major steps encoded by certain software products disclosed herein.

FIG. 25 shows the nucleotide sequence for an exemplary adapter that can be used in the construction of certain libraries as disclosed herein.

FIG. 26 shows results of a chromatin immunoprecipitation (ChIP) experiment demonstrating the association of acetylated histone H3 with sequences which regulate transcription of the p16 gene. See Example 17.

FIG. 27 shows VEGF protein levels, measured by ELISA, in cells transfected with plasmids encoding fusions of the EPAS activation domain to ZFP binding domains targeted to different sites in the human VEGF-A gene. The ZFP binding domain characteristic of each fusion is identified on the abscissa, and the locations of their target sites are given in Table 2. See Example 18.

FIG. 28 shows an analysis of DNase I hypersensitive regions in the vicinity of the first exon of the human p14ARF gene. The leftmost panel at the top of the figure shows size markers generated by hybridization of the probe to genomic DNA that had been double digested with Eco RI and the enzyme indicated at the top of each lane. Subsequent panels show analyses of DNase I hypersensitivity in HCT15 cells, 293 cells, H596 cells and HCT15 cells, respectively. At the bottom of the figure, a schematic diagram shows the locations of the hypersensitive sites in the p14 gene with respect to an Alu repeat (Alu), a CpG island (CpG) and the transcription startsite (rightward-pointing arrow). See Example 20.

DETAILED DESCRIPTION

I. Definitions

The practice of conventional techniques in molecular biology, biochemistry, chromatin structure and analysis, computational chemistry, cell culture, recombinant DNA, bioinformatics, genomics and related fields are well-known to those of skill in the art and are discussed, for example, in the following literature references: Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999, all of which are incorporated by reference in their entireties.

The terms "nucleic acid," "polynucleotide," and "oligonucleotide" are used interchangeably and refer to a deoxyribonucleotide or ribonucleotide polymer in either single- or double-stranded form. When not used to refer to a nucleic acid obtained from an organism, the term can encompass known analogues of natural nucleotides that hybridize to nucleic acids in a manner similar to naturally-occurring nucleotides.

Chromatin is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and components of chromatin remodeling complexes.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability In general, gene activation comprises any detectable increase in the production of a gene product, preferably an increase in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more. Most preferably, gene repression results in complete inhibition of gene expression, such that no gene product is detectable.

"Eucaryotic cells" include, but are not limited to, fungal cells (such as yeast), plant cells, animal cells, mammalian cells and human cells.

The terms "operative linkage" and "operatively linked" are used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al; supra. The ability of a protein to interact with another protein can be determined, for example, by co-immunoprecipitation, two-hybrid assays or complementation, both genetic and biochemical. See, for example, Fields et al. (1989) Nature 340:245–246; U.S. Pat. No. 5,585,245 and PCT WO 98/44350.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "naturally occurring," as applied to an object, means that the object can be found in nature.

The terms "polypeptide," "peptide" and "protein" are used interchangeably to refer to a polymer of amino acid residues. The term also applies to amino acid polymers in which one or more amino acids are chemical analogues of a corresponding naturally-occurring amino acids.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The term "antibody" as used herein includes antibodies obtained from both polyclonal and monoclonal preparations, as well as, the following: (i) hybrid (chimeric) antibody molecules (see, for example, Winter et al. (1991) Nature 349:293–299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659–2662; and Ehrlich et al. (1980) Biochem 19:4091–4096); (iv) single-chain Fv molecules (sFv) (see, for example, Huston et al. (1988) Proc. Natl. Acad. Sci. USA 85:5879–5883); (v) dimeric and trimeric antibody fragment constructs; (vi) humanized antibody molecules (see, for example, Riechmann et al. (1988) Nature 332:323–327; Verhoeyan et al. (1988) Science 239:1534–1536; and U.K. Patent Publication No. GB 2,276, 169, published Sep. 21, 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579–1584; Cumber et al. (1992) J. Immunology 149B:120–126); and, (vii) any functional fragments obtained from such molecules, wherein such fragments retain specific-binding properties of the parent antibody molecule.

"Specific binding" between an antibody or other binding agent and an antigen, or between two binding partners, means that the dissociation constant for the interaction less than $10^{-6}$ M. Preferred antibody/antigen or binding partner complexes have a dissociation constant of less than about $10^{-7}$ M, and preferably $10^{-8}$ M to $10^{-9}$ M or $10^{-10}$ M.

The term "common," when used in reference to two or more polynucleotide sequences being compared, refers to polynucleotides that (i) exhibit a selected percentage of sequence identity (as defined below, typically between 80–100% sequence identity) and/or (ii) are located in similar positions, relative to a gene of interest. Likewise, the term "unique," when used in reference to two or more polynucleotide sequences being compared, refers to polynucleotides that (i) do not exhibit a selected percentage of sequence identity as defined below, typically less than 80% sequence identity) and/or (ii) are located in one or more different positions relative to a gene of interest.

"Sequence similarity" refers to the percent similarity in base pair sequence (as determined by any suitable method) between two or more polynucleotide sequences. Two or more sequences can be anywhere from 0–100% similar, or any integer value therebetween. Furthermore, sequences are considered to exhibit "sequence identity" when they are at least about 80–85%, preferably at least about 85–90%, more preferably at least about 90–92%, more preferably at least about 93–95%, more preferably 96–98%, and most preferably at least about 98–100% sequence identity (including all integer values falling within these described ranges). These percent identities are, for example, relative to the claimed sequences, or other sequences, when the sequences obtained by the methods disclosed herein are used as the query sequence. Additionally, one of skill in the art can readily determine the proper search parameters to use for any given sequence in the programs described herein. For example, the search parameters may vary based on the size of the sequence in question. Thus, for example, in certain embodiments, the search is conducted based on the size of the isolated polynucleotide(s) corresponding to an accessible region. The isolated polynucleotide comprises X contiguous nucleotides and is compared to the sequences of approximately same length, preferably the same length. Exemplary fragment lengths include, but are not limited to, at least about 6–1000 contiguous nucleotides (or any integer therebetween), at least about 50–750 contiguous nucleotides (or any integer therebetween), about 100–300 contiguous nucleotides (or any integer therebetween), wherein such contiguous nucleotides can be derived from a larger sequence of contiguous nucleotides.

Techniques for determining nucleic acid and amino acid sequence similarity are known in the art. Typically, such techniques include determining the nucleotide sequence of, e.g., an accessible region of cellular chromatin, and comparing these sequences to a second nucleotide sequence. Genomic sequences can also be determined and compared in this fashion. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). An additional method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect= 10; Matrix=BLOSUM62; Descriptions=50 sequences; sort by=HIGH SCORE; Databases=non-redundant, GenBank+ EMBL+DDBJ+PDB+GenBank CDS translations+Swiss protein+Spupdate+PIR. Details of these programs can be found at the following internet address: http://www.ncbi.nlm.gov/cgi-bin/BLAST. When claiming sequences relative to sequences described herein, the range of desired degrees of sequence identity is approximately 80% to 100% and any integer value therebetween. Typically the percent identities between the disclosed sequences and the claimed sequences are at least 70–75%, preferably 80–82%, more preferably 85–90%, even more preferably 92%, still more preferably 95%, and most preferably 98% sequence identity to the reference sequence.

II. Overview

The present disclosure provides methods for the identification, isolation and characterization of regulatory DNA sequences in a cell of interest, without requiring a knowledge of the functional properties of the regulatory sequences. Also provided are methods for determining the effect of a drug on regulatory accessible regions; methods of elucidating signal transduction pathways; methods of modulating signal transduction pathways and methods of pharmacologically determining a drug therapy to administer to a subject. These methods are based in part upon the recognition that regulatory sequences can be identified based upon differences of accessibility for these regions as compared to other regions of cellular chromatin. Also provided are regulatory sequences obtained according to the methods disclosed herein, collections of accessible or regulatory sequences obtained according to the methods disclosed herein (e.g., libraries), and databases comprising collections of accessible or regulatory sequences for one or more cells of interest. Also disclosed are various uses for the regulatory sequences so obtained, and uses for the databases of accessible or regulatory sequences.

As noted above, in general, regulatory sequences are identified based upon their differential accessibility in cellular chromatin as compared to other sequences. Accessible regions can be identified by a number of different approaches. For instance, accessible sequences can be identified based on their reactivity with chemical and/or enzymatic probes. Accessible regions, in general, have an altered reactivity to a probe, compared to bulk chromatin. An accessible region can be sensitive to the probe, compared to bulk chromatin, or it can have a pattern of sensitivity that is different from the pattern of sensitivity exhibited by bulk chromatin. Any method for probing chromatin structure, known to one of skill in the art, can be used to identify one or more accessible regions in cellular chromatin.

For instance, accessible regions can be identified by selective or limited cleavage of cellular chromatin to obtain polynucleotide fragments that are enriched in regulatory sequences. One general approach is to utilize nucleases (e.g., DNase I) under appropriate conditions to generate fragments from accessible regions that can be separated from the remaining bulk chromatin. The reaction conditions are controlled to prevent the nuclease from cleaving the accessible regions into individual nucleotides or very small oligonucleotides.

Other identification and isolation approaches involve the use of chemical and/or enzymatic probes to mark sequences present in accessible regions (e.g., by reaction with a functional group of a nucleotide) followed by fragmentation; marked fragments can subsequently be isolated from unmarked sequences. A marked polynucleotide sequence is one which includes a site of probe interaction. A specific example is a polynucleotide sequence that is methylated through the action of a methylase. Chemical probes can be used in like manner to generate polynucleotide sequences in which one or more nucleotides are modified and can be distinguished and separated from unmarked polynucleotides.

Another general approach based on selective digestion is to use specific restriction enzymes to cleave non-regulatory sequences, thereby leaving fragments that are enriched in regulatory sequences. Certain of these methods involve using appropriate restriction enzymes to obtain fragments enriched in CpG islands, as such regions often comprise regulatory sequences. Fragments enriched in CpG islands can be obtained, for example, by digesting cellular DNA or chromatin with restriction enzymes that selectively cleave AT rich segments.

It is also possible to utilize methylation-sensitive restriction enzymes that do not cut methylated DNA. Since CpG islands of active genes are often unmethylated, digestion of cellular DNA or chromatin with such enzymes, which in addition contain the sequence CG in their recognition sequence, generate small fragments from unmethylated CpG island DNA.

Various immunological precipitation methods can also be utilized. Certain methods take advantage of the fact that regulatory regions are enriched in acetylated histones, such as acetylated H3. Hence, these methods involve fragmenting chromatin and then contacting the fragments with antibodies specific for acetylated histones to obtain nucleic acid sequences enriched in regulatory sequences. The histones can optionally be crosslinked to the DNA prior to fragmentation. Antibodies to various transcriptional regulatory molecules can also be used in similar methods.

Other methods for identifying accessible regions take a different approach and involve the use of probes to degrade accessible regions to identify the boundaries or termini of regulatory regions. Such methods can utilize any of a number of nucleases, for example. The boundaries can then be mapped on the overall genomic sequence to identify potential regulatory regions.

Once accessible regions have been identified, the sequences of the regions can be determined in a number of different ways such as direct sequencing of isolated accessible polynucleotide sequences or mapping the sequences against the genomic sequence. Isolated polynucleotide fragments corresponding to accessible regions can be cloned and used to prepare collections or libraries of accessible regions. Sequence information for accessible regions can also be accumulated for computerized access in databases or other data structures. Hence, libraries of isolated polynucleotides that correspond to accessible regions, as well as databases of sequences corresponding to accessible regions, are provided.

The data structures (e.g., databases) disclosed herein can be utilized in performing a variety of different comparisons using computer systems and computer program products also disclosed herein. The databases, systems and programs can be used, for example, to identify particular types of regulatory sequences, to identify active or quiescent regulatory regions in different cell types and to investigate variations in regions that are accessible in different cell types, such as differences between diseased and healthy cells, cells at different stages of development and cells from different tissues. Such systems and programs can also be used to study different pathways of gene control, signal transduction processes involved in gene regulation, as well as in the design of exogenous regulatory molecules and vectors including transgenes.

III. Methods for Identifying Regulatory Regions
A. General

Regulatory sequences are estimated to occupy between 1 and 10% of the human genome. Such sequences include, but are not limited to, promoters, enhancers, silencers, locus control regions, boundary elements (e.g., insulators), splice sites, transcription termination sites, polyA addition sites, matrix attachment regions, sites involved in control of replication (e.g., replication origins), centromeres, telomeres, and sites regulating chromosome structure (see FIG. 1). See, for example, Wingender et al. (1997) *Nucleic Acids Res.* 25:265–268. As noted supra, the methods disclosed herein allow identification, purification and characterization of regulatory sequences in a cell of interest, without requiring knowledge of the functional properties of the sequences. Once identified, the regulatory regions can be isolated, cloned, amplified and/or their nucleotide sequences determined.

Chromatin is a complex comprising cellular DNA and chromosomal proteins. In addition, most cellular RNAs also exist in the form of nucleoprotein complexes. In general, chromosomal DNA is packaged into nucleosomes. A nucleosome comprises a core and a linker. The nucleosome core comprises an octamer of core histones (two each of H2A, H2B, H3 and H4) around which is wrapped approximately 150 base pairs of chromosomal DNA. In addition, a linker DNA segment of approximately 50 base pairs is associated with linker histone H1 (or a related linker histone in certain specialized cells). Nucleosomes are organized into a higher-order chromatin fiber and chromatin fibers are organized into chromosomes. See, for example, Wolffe "Chromatin: Structure and Function" 3rd Ed., Academic Press, San Diego, 1998.

Regulatory sequences can be identified on the basis of their accessibility in cellular chromatin. Accessibility is any property that distinguishes a particular region of DNA, in cellular chromatin, from bulk cellular DNA. For example, an accessible sequence (or accessible region) can be one that is not packaged into nucleosomes, or can comprise DNA present in nucleosomal structures that are different from that of bulk nucleosomal DNA (e.g., nucleosomes comprising modified histones). An accessible region includes, but is not limited to, a site in chromatin at which an enzymatic or chemical probe reacts, under conditions in which the probe does not react with similar sites in bulk chromatin. Such regions of chromatin can include, for example, a functional group of a nucleotide, in which case probe reaction can generate a modified nucleotide, or a phosphodiester bond between two nucleotides, in which case probe reaction can generate polynucleotide fragments or chromatin fragments.

B. Isolating Marked or Modified Fragments
1. Generally

Certain methods for identifying accessible regions involve the use of an enzymatic probe that modifies DNA in chromatin. Modified regions, which comprise accessible sequences, are then identified and can be isolated. Such methods generally comprise the treatment of cellular chromatin with a chemical and/or enzymatic probe wherein the probe reacts with (but does not cleave) accessible sequences. The treated chromatin is optionally deproteinized and then fragmented to produce a mixture of polynucleotide fragments, wherein the mixture comprises fragments containing at least one site that has reacted with the probe (marked polynucleotide fragments) and fragments that have not reacted with the probe (unmarked polynucleotide fragments). Marked fragments are selected and correspond to accessible regions of cellular chromatin.

Fragmentation is achieved by any method of polynucleotide fragmentation known to those of skill in the art including, but not limited to, nuclease digestion (e.g., restriction enzymes, non-sequence-specific nucleases such as DNase I, micrococcal nuclease, S1 nuclease and mung bean nuclease), and physical methods such as shearing and sonication. Isolation is accomplished by any technique that allows for the selective purification of marked fragments from unmarked fragments (e.g., size or affinity separation techniques and/or purification on the basis of a physical property).

2. Methods with Enzymatic Probes

A variety of enzymatic probes can be used to identify accessible regions of chromatin. Suitable enzymatic probes in general include any enzyme that can react with one or more sites in an accessible region to, for example, modify a nucleotide within the region, thereby generating a modified product. The modification provides the basis for selection of marked polynucleotides and their separation from unmarked polynucleotides.

DNA methyltransferase enzymes (or simply methylases) are examples of one group of suitable enzymes. Of the naturally-occurring nucleosides only thymidine contains a methyl group (at the 5-position of the pyrimidine ring).

Bacterial and eukaryotic methylases generally add methyl groups to nucleosides other than thymidine, to form, for example, $N^6$-methyladenosine and 5-methylcytidine.

Methods employing methylases generally involve contacting cellular chromatin with a DNA methylase such that accessible DNA sequences are methylated. The chromatin is optionally deproteinized and, in one embodiment, the resulting methylated DNA is subsequently treated with a methylation-sensitive enzyme to generate large fragments corresponding to accessible regions. Alternatively, or in addition, methylated chromatin or DNA is treated with a methylation-dependent enzyme (e.g., a restriction enzyme that does not cleave at its recognition sequence unless the recognition sequence is methylated) to generate small fragments comprising accessible regions and larger fragments whose boundaries comprise accessible regions. In yet another alternative, cellular chromatin is contacted with a methylase, optionally deproteinized, fragmented, and methylated DNA fragments selected using antibodies to methylated nucleotides or methylated DNA.

For example, in certain methods, the dam methylase (*E. coli* DNA adenine methylase), which methylates the $N^6$ position of adenine residues in the sequence 5'-GATC-3', is used. This enzyme is useful in the analysis of regulatory regions in eukaryotic cells because adenine methylation does not normally occur in eukaryotic cells. Other exemplary methylases include, but are not limited to, AluI methylase, BamHI methylase, ClaI methylase, EcoRI methylase, FnuDII methylase, HaeIII methylase, HhaI methylase, HpaII methylase, Msp I methylase, PstI methylase, SssI methylase, TaqI methylase, dcm (Mec) methylase, EcoK methylase and Dnmtl methylase. These and related enzymes are commercially available, for example, from New England BioLabs, Inc. Beverly, Mass.

Following methylase treatment, accessible regions are identified by distinguishing methylated from non-methylated DNA. Some methods involve generating fragments of DNA and then separating those fragments that include methylated nucleotides (i.e., marked fragments) from those fragments that are unmethylated (i.e., unmarked fragments). For example, in embodiments in which cellular chromatin is treated with dam methylase, methylated fragments can be isolated by affinity purification using antibodies to $N^6$-methyl adenine. Bringmann et al. (1987) *FEBS Lett.* 213:309–315. Any affinity purification technique known in the art such as, for example, affinity chromatography using immobilized antibody, can be used.

Methylated accessible regions can also be selected and isolated based on their possession of methylated restriction sites which are resistant to cleavage by methylation-sensitive restriction enzymes. For example, subsequent to its methylation, cellular chromatin is deproteinized and subjected to the activity of a methylation-sensitive restriction enzyme. A methylation-sensitive enzyme refers to a restriction enzymes that does not cleave DNA (or cleaves DNA poorly) if one or more nucleotides in its recognition site are methylated. Exemplary enzymes of this type include MboI and DpnII, both of which digest DNA at the sequence 5'-GATC-3' only if the A residue is unmethylated. (Note that this is the same sequence that is methylated by dam methylase.) Since both of these enzymes have four-nucleotide recognition sequences, they generate, on average, small fragments of non-methylated DNA. Methylated regions, corresponding to areas of chromatin originally accessible to the methylase, are resistant to digestion and can be isolated, for example, based on their larger size, or through affinity methods that recognize methylated DNA (e.g., antibodies to $N^6$-methyl adenine, supra). Other methylation sensitive enzymes include, but are not limited to, HpaII, and ClaI. See, in addition, the New England BioLabs 2000–01 Catalogue & Technical Reference, esp. pages 220–221 and references cited therein.

In other embodiments, preferential cleavage of methylated DNA (obtained from cellular chromatin that has been methylated as described supra) by certain enzymes such as, for example, methylation-dependent restriction enzymes, generates small fragments, which can be separated from larger, unmethylated DNA fragments. For example, treatment of cellular chromatin with dam methylase, followed by deproteinization and digestion of methylated DNA with DpnI (which cleaves at the 4-nucleotide recognition sequence 5'-GATC-3' only if the A residue is methylated) will generate relatively small fragments from methylated accessible regions. These can be isolated based on size or affinity procedures, as disclosed supra. In addition, the larger fragments generated by this procedure comprise the distal portions and boundaries of accessible regions at their termini and can be isolated based on size. Another methylation-dependent enzyme, which cleaves at sequence different from that recognized by Dpn I, is Mcr BC. This enzyme, as well as additional methylation-dependent restriction enzymes, are disclosed in the New England BioLabs 2000–01 Catalog and Technical Reference.

Additional enzymatic probes of chromatin structure, which can be used to identify accessible regions, include micrococcal nuclease, S1 nuclease, mung bean nuclease, and restriction endonucleases. In addition, the method described by van Steensel et al. (2000) *Nature Biotechnol.* 18:424–428 can be used to identify accessible regions.

3. Methods with Chemical Probes

Another option for marking accessible regions in chromatin is to use various chemical probes. In general, these chemical probes react with a functional group of one or more nucleotides within an accessible region to generate a modified or derivatized nucleotide. Following cleavage of chromatin according to the established methods described supra, fragments including one or more derivatized nucleotides can be separated from those fragments that do not include modified nucleotides.

A variety of different chemical probes can be utilized to modify DNA in accessible regions. In general, the size and reactivity of such probes should enable the probes to react with nucleotides located within accessible regions. Chemical modification of cellular chromatin in accessible regions can be accomplished by treatment of cellular chromatin with reagents such as dimethyl sulfate, hydrazine, potassium permanganate, and osmium tetroxide. Maxam et al. (1980) *Meth. Enzymology*, Vol. 65, (L. Grossman & K. Moldave, eds.) Academic Press, New York, pp. 499–560. Additional exemplary chemical modification reagents are the psoralens, which are capable of intercalation and crosslink formation in double-stranded DNA.

As noted supra, once cellular chromatin has been contacted with a chemical probe and the reactants allowed a sufficient period in which to react, the resulting modified chromatin is fragmented using various cleavage methods. Exemplary techniques include reaction with restriction enzymes, sonication and shearing methods. Following fragmentation, marked polynucleotides corresponding to accessible regions can be purified from unmarked polynucleotides. Purification can be based on affinity methods such as, for example, binding to antibodies specific for the product of modification.

In certain embodiments, chemical and enzymatic probes can be combined to generate marked fragments that can be purified from unmarked fragments.

4. Methods with Binding Molecules

In certain embodiments, a molecule which is capable of binding to an accessible region, but does not necessarily cleave or covalently modify DNA in the accessible region, can be used to identify and isolate accessible regions. Suitable molecules include, for example, minor groove binders (e.g., U.S. Pat. Nos. 5,998,140 and 6,090,947), and triplex-forming oligonucleotides (TFOs, U.S. Pat. Nos. 5,176,996 and 5,422,251). The molecule is contacted with cellular chromatin, the chromatin is optionally deproteinized, then fragmented, and fragments comprising the bound molecule are isolated, for example, by affinity techniques. Use of a TFO comprising poly-inosine (poly-I) will lead to minimal sequence specificity of triplex formation, thereby maximizing the probability of interaction with the greatest possible number of accessible sequences.

In a variation of one of the aforementioned methods, TFOs with covalently-attached modifying groups are used. See, for example, U.S. Pat. No. 5,935,830. In this case, covalent modification of DNA occurs in the vicinity of the triplex-forming sequence. After optional deproteinization and fragmentation of treated chromatin, marked fragments are purified by, for example, affinity selection.

In another embodiment, cellular chromatin is contacted with a non-sequence-specific DNA-binding protein. The protein is optionally crosslinked to the chromatin. The chromatin is then fragmented, and the mixture of fragments is subjected to immunoprecipitation using an antibody directed against the non-sequence-specific DNA-binding protein. Fragments in the immunoprecipitate are enriched for accessible regions of cellular chromatin. Suitable non-sequence-specific DNA-binding proteins for use in this method include, but are not limited to, procaryotic histone-like proteins such as the bacteriophage SP01 protein TF1 and procaryotic HU/DBPII proteins. Greene et al. (1984) *Proc. Natl. Acad. Sci. USA* 81:7031–7035; Rouviere-Yaniv et al. (1977) *Cold Spring Harbor Symp. Quant. Biol.* 42:439–447; Kimura et al (1983) *J. Biol. Chem.* 258:4007–4011; Tanaka et al. (1984) *Nature* 310:376–381. Additional non-sequence-specific DNA-binding proteins include, but are not limited to, proteins containing poly-arginine motifs and sequence-specific DNA-binding proteins that have been mutated so as to retain DNA-binding ability but lose their sequence specificity. An example of such a protein (in this case, a mutated restriction enzyme) is provided by Rice et al. (2000) *Nucleic Acids Res.* 28:3143–3150.

In yet another embodiment, a plurality of sequence-specific DNA binding proteins is used to identify accessible regions of cellular chromatin. For example, a mixture of sequence-specific DNA binding proteins of differing binding specificities is contacted with cellular chromatin, chromatin is fragmented and the mixture of fragments is immunoprecipitated using an antibody that recognizes a common epitope on the DNA binding proteins. The resulting immunoprecipitate is enriched in accessible sites corresponding to the collection of DNA binding sites recognized by the mixture of proteins. Depending on the completeness of sequences recognized by the mixture of proteins, the accessible immunoprecipitated sequences will be a subset or a complete representation of accessible sites.

In addition, synthetic DNA-binding proteins can be designed in which non-sequence-specific DNA-binding interactions (such as, for example, phosphate contacts) are maximized, while sequence-specific interactions (such as, for example, base contacts) are minimized. Certain zinc finger DNA-binding domains obtained by bacterial two-hybrid selection have a low degree of sequence specificity and can be useful in the aforementioned methods. Joung et al. (2000) *Proc. Natl. Acad. Sci. USA* 97:7382–7387; see esp. the "Group III" fingers described therein.

C. Selective/Limited Digestion Methods

1. Limited Nuclease Digestion

This approach generally involves treating nuclei or chromatin under controlled reaction conditions with a chemical and/or enzymatic probe such that small fragments of DNA are generated from accessible regions. The selective and limited digestion required can be achieved by controlling certain digestion parameters. Specifically, one typically limits the concentration of the probe to very low levels. The duration of the reaction and/or the temperature at which the reaction is conducted can also be regulated to control the extent of digestion to desired levels. More specifically, relatively short reaction times, low temperatures and low concentrations of probe can be utilized. (See Example 2, infra).

Any of a variety of nucleases can be used to conduct the limited digestion. Both non-sequence-specific endonucleases such as, for example, DNase I, S1 nuclease, and mung bean nuclease, and sequence-specific nucleases such as, for example, restriction enzymes, can be used.

A variety of different chemical probes can be utilized to cleave DNA in accessible regions. Specific examples of suitable chemical probes include, but are not limited to, hydroxyl radicals and methidiumpropyl-EDTA.Fe(II) (MPE). Chemical cleavage in accessible regions can also be accomplished by treatment of cellular chromatin with reagents such as dimethyl sulfate, hydrazine, potassium permanganate, and osmium tetroxide, followed by exposure to alkaline conditions (e.g., 1 M piperidine). See, for example, Tullius et al. (1987) *Meth. Enzymology*, Vol. 155, (J. Ableson & M. Simon, eds.) Academic Press, San Diego, pp. 537–558; Cartwright et al. (1983) Proc. Natl. Acad. Sci. USA 80:3213–3217; Hertzberg et al. (1984) *Biochemistry* 23:3934–3945; Wellinger et al. in Methods in Molecular Biology, Vol. 119 (P. Becker, ed.) Humana Press, Totowa, N.J., pp. 161–173; and Maxam et al. (1980) *Meth. Enzymology*, Vol. 65, (L. Grossman & K. Moldave, eds.) Academic Press, New York, pp. 499–560.

When using chemical probes, reaction conditions are adjusted so as to favor the generation of, on average, two sites of reaction per accessible region, thereby releasing relatively short DNA fragments from the accessible regions.

As with the previously-described methods, the resulting small fragments generated by the digestion process can be purified by size (e.g., gel electrophoresis, sedimentation, gel filtration), preferential solubility, or by procedures which result in the separation of naked nucleic acid (i.e., nucleic acids lacking histones) from bulk chromatin, thereby allowing the small fragments to be isolated and/or cloned, and/or subsequently analyzed by, for example, nucleotide sequencing.

In one embodiment of this method, nuclei are treated with low concentrations of DNase; DNA is then purified from the nuclei and subjected to gel electrophoresis. The gel is blotted and the blot is probed with a short, labeled fragment corresponding to a known mapped DNase hypersensitive site located, for example, in the promoter of a housekeeping gene. Examples of such genes (and associated hypersensitive sites) include, but are not limited to, those in the genes encoding rDNA, glyceraldehyde-3-phosphate dehydrogenase (GAPDH) and core histones (e.g., H2A, H2B, H3, H4). Alternatively, a DNA fragment size fraction is isolated from the gel, slot-blotted and probed with a hypersensitive site probe and a probe located several kilobases (kb) away from the hypersensitive site. Preferential hybridization of the hypersensitive site probe to the size fraction is indicative that the fraction is enriched in accessible region sequences. A size fraction enriched in accessible region sequences can be cloned, using standard procedures, to generate a library of accessible region sequences (see infra). See Example 9.

2. Release of Sequences Enriched in CpG Islands

The dinucleotide CpG is severely underrepresented in mammalian genomes relative to its expected statistical occurrence frequency of 6.25%. In addition, the bulk of CpG residues-in the genome are methylated (with the modification occurring at the 5-position of the cytosine base). As a consequence of these two phenomena, total human genomic DNA is remarkably resistant to, for example, the restriction endonuclease Hpa II, whose recognition sequence is CCGG, and whose activity is blocked by methylation of the second cytosine in the target site.

An important exception to the overall paucity of demethylated Hpa II sites in the genome are exceptionally CpG-rich sequences (so-called "CpG islands") that invariably occur in the vicinity of transcriptional startsites, and which are demethylated in the promoters of active genes. Jones et al. (1999) *Nature Genet.* 21:163–167. Aberrant hypermethylation of such promoter-associated CpG islands is a well-established characteristic of the genome of malignant cells. Robertson et al. (2000) *Carcinogenesis* 21:61–467.

Accordingly, another option for generating accessible regions relies on the observation that, whereas most CpG dinucleotides in the eukaryotic genome are methylated at the C5 position of the C residue, CpG dinucleotides within the CpG islands of active genes are unmethylated. See, for example, Bird (1992) *Cell* 70:5–8; and Robertson et al. (2000) *Carcinogenesis* 21:461–467. Indeed, methylation of CpG is one mechanism by which eukaryotic gene expression is repressed. Accordingly, digestion of cellular DNA with a methylation-sensitive restriction enzyme (i.e., one that does not cleave methylated DNA), especially one with the dinucleotide CpG in its recognition sequence, such as, for example, Hpa II, generates small fragments from unmethylated CpG island DNA. For example, upon the complete digestion of genomic DNA with Hpa II, the overwhelming majority of DNA will remain >3 kb in size, whereas the only DNA fragments of approximately 100–200 bp will be derived from demethylated, CpG-rich sequences, i.e., the CpG islands of active genes. See Example 6. Such small fragments are enriched in regulatory regions that are active in the cell from which the DNA was derived. They can be purified by differential solubility or size selection, for example, cloned to generate a library, and their nucleotide sequences determined and placed in one or more databases. Specific examples of these approaches are set forth infra in Examples 6 and 10.

Digestion with methylation-sensitive enzymes can be conducted in whole cells, in isolated nuclei, with bulk chromatin or with naked DNA obtained after stripping proteins from chromatin. In all instances, relatively small fragments are excised and these can be separated from the bulk chromatin or the longer DNA fragments corresponding to regions containing methylated CpG dinucleotides. The small fragments including unmethylated CpG islands can be isolated from the larger fragments using various size-based purification techniques (e.g., gel electrophoresis, sedimentation and size-exclusion columns) or differential solubility, for example.

As indicated supra, a variety of methylation-sensitive restriction enzymes are commercially available, including, but not limited to, DpnII, MboI, HpaII and ClaI. Each of the foregoing is available from commercial suppliers such as, for example, New England BioLabs, Inc., Beverly, Mass.

In another embodiment, enrichment of regulatory sequences is accomplished by digestion of deproteinized genomic DNA with agents that selectively cleave AT-rich DNA. Examples of such agents include, but are not limited to, restriction enzymes having recognition sequences consisting solely of A and T residues, and single strand-specific nucleases, such as S1 and mung bean nuclease, used at elevated temperatures. Examples of suitable restriction enzymes include, but are not limited to, Mse I, Tsp509 I, Ase I, Dra I, Pac I, Psi I, Ssp I and Swa I. Such enzymes are available commercially, for example, from New England Biolabs, Beverly, Mass. Because of the concentration of GC-rich sequences within CpG islands (see supra), large fragments resulting from such digestion generally comprise CpG island regulatory sequences, especially when a restriction enzyme with a four-nucleotide recognition sequence consisting entirely of A and T residues (e.g., Mse I, Tsp509 I), is used as a digestion agent. See Example 7. Such large fragments can be separated, based on their size, from the smaller fragments generated from cleavage at regions rich in AT sequences. In certain cases, digestion with multiple enzymes recognizing AT-rich sequences provides greater enrichment for regulatory sequences. See Example 8.

Alternatively, or in addition to a size selection, large, CpG island-containing fragments generated by these methods can be subjected to an affinity selection to separate methylated from unmethylated large fragments. Separation can be achieved, for example, by selective binding to a protein containing a methylated DNA binding domain (Hendrich et al. (1998) *Mol. Cell. Biol.* 18:6538–6547; Bird et al. (1999) *Cell* 99:451–454) and/or to antibodies to methylated cytosine. Unmethylated large fragments are likely to comprise regulatory sequences involved in gene activation in the cell from which the DNA was derived. As with other embodiments, polynucleotides obtained by the aforementioned methods can be cloned to generate a library of regulatory sequences.

Regardless of the particular strategy employed to purify the unmethylated CpG islands from other fragments, the isolated fragments can be cloned to generate a library of regulatory sequences. The nucleotide sequences of the members of the library can be determined, optionally placed in one or more databases, and compared to a genome database to map these regulatory regions on the genome.

D. Immunoprecipitation

In other methods for identification and isolation of regulatory regions, enrichment of regulatory DNA sequences takes advantage of the fact that the chromatin of actively-transcribed genes generally comprises acetylated histones. See, for example, Wolffe et al. (1996) *Cell* 84:817–819. In particular, acetylated H3 and H4 are enriched in the chromatin of transcribed genes, and chromatin comprising regulatory sequences is selectively enriched in acetylated H3. Accordingly, chromatin immunoprecipitation using antibodies to acetylated histones, particularly acetylated H3, can be used to obtain collections of sequences enriched in regulatory DNA.

Such methods generally involve fragmenting chromatin and then contacting the fragments with an antibody that specifically recognizes and binds to acetylated histones, particularly H3. The polynucleotides from the immunoprecipitate can subsequently be collected from the immunoprecipitate. Prior to fragmenting the chromatin, one can optionally crosslink the acetylated histones to adjacent DNA.

Crosslinking of histones to the DNA within the chromatin can be accomplished according to various methods. One approach is to expose the chromatin to ultraviolet irradiation. Gilmour et al. (1984) *Proc. Natl. Acad. Sci. USA* 81:4275–4279. Other approaches utilize chemical crosslinking agents. Suitable chemical crosslinking agents include, but are not limited to, formaldehyde and psoralen. Solomon et al. (1985) *Proc. Natl. Acad. Sci. USA* 82:6470–6474; Solomon et al (1988) *Cell* 53:937–947.

Fragmentation can be accomplished using established methods for fragmenting chromatin, including, for example, sonication, shearing and/or the use of restriction enzymes. The resulting fragments can vary in size, but using certain sonification techniques, fragments of approximately 200–400 nucleotide pairs are obtained.

Antibodies that can be used in the methods are commercially available from various sources. Examples of such antibodies include, but are not limited to, Anti Acetylated Histone H3, available from Upstate Biotechnology, Lake Placid, N.Y.

Identification of a binding site for a particular defined transcription factor in cellular chromatin is indicative of the presence of regulatory sequences. This can be accomplished, for example, using the technique of chromatin immunoprecipitation. Briefly, this technique involves the use of a specific antibody to immunoprecipitate chromatin complexes comprising the corresponding antigen (in this case, the transcription factor of interest), and examination of the nucleotide sequences present in the immunoprecipitate. Immunoprecipitation of a particular sequence by the antibody is indicative of interaction of the antigen with that sequence. See, for example, O'Neill et al. in Methods in Enzymology, Vol. 274, Academic Press, San Diego, 1999, pp. 189–197; Kuo et al. (1999) Method 19:425–433; and Current Protocols in Molecular Biology, F. M. Ausubel et al., eds., Current Protocols, Chapter 21, a joint venture between Greene Publishing Associates, Inc. and John Wiley & Sons, Inc., (1998 Supplement).

As with the other methods, polynucleotides isolated from an immunoprecipitate, as described herein, can be cloned to generate a library and/or sequenced, and the resulting sequences used to populate a database as described in greater detail infra. Sequences adjacent to those detected by this method are also likely to be regulatory sequences. These can be identified by mapping the isolated sequences on the genome sequence for the organism from which the chromatin sample was obtained, and optionally entered into one or more databases.

E. Digestion of Accessible Regions

1. Nuclease Treatment

Additional embodiments for the identification and isolation of accessible region regulatory sequences involve selective degradation of accessible regions. Such approaches are useful for establishing the boundaries of accessible regions. Once these boundaries are located on the genome sequence, it is possible to deduce which sequences correspond to regulatory sequences.

Accordingly, certain methods for identification and isolation of accessible regions in cellular chromatin utilize various nucleases or chemical agents to cleave accessible regions. Such methods are typically initiated by contacting cellular chromatin with the cleavage agent to digest the accessible regions and allowing reaction to proceed until most or all accessible DNA is degraded. These methods are thus distinguished from certain of the methods described supra in that the extent of reaction with the cleavage agent is more extensive in the present embodiment. The resulting fragments are then optionally deproteinized to generate naked DNA fragments that can be subsequently analyzed to establish the boundaries of the regulatory regions by, for example, restriction mapping, hybridization and/or nucleotide sequence determination.

DNase I (pancreatic deoxyribonuclease) is one example of an enzymatic cleavage reagent that can be used in this embodiment. Regions of cellular chromatin that exhibit enhanced sensitivity to digestion by DNase I, compared to bulk chromatin (i.e., DNase-hypersensitive sites) comprise accessible sequences likely to be involved in the regulation of gene expression. Other enzymatic probes that can be utilized in the digestion of accessible regions include, but are not limited to, micrococcal nuclease, S1 nuclease and mung bean nuclease. See Examples 1, 2 and 5.

A variety of different chemical probes can be utilized to degrade DNA in accessible regions. These include, but are not limited to, hydroxyl radicals and methidiumpropyl-EDTA.Fe(II) (MPE). Chemical cleavage in accessible regions can also be accomplished by treatment of cellular chromatin with reagents such as dimethyl sulfate, hydrazine, potassium permanganate, and osmium tetroxide, followed by exposure to alkaline conditions (e.g., 1 M piperidine). See, for example, Tullius et al. (1987) Meth. Enzymology, Vol. 155, (J. Ableson & M. Simon, eds.) Academic Press, San Diego, pp. 537–558; Cartwright et al. (1983) Proc. Natl. Acad. Sci. USA 80:3213–3217; Hertzberg et al. (1984) Biochemistry 23:3934–3945; Wellinger et al. in Methods in Molecular Biology, Vol. 119 (P. Becker, ed.) Humana Press, Totowa, N.J., pp. 161–173; and Maxam et al. (1980) Meth. Enzymology, Vol. 65, (L. Grossman & K. Moldave, eds.) Academic Press, New York, pp. 499–560.

Micrococcal nuclease (MNase) is used as a probe of chromatin structure in other methods to identify accessible regions. MNase preferentially digests the linker DNA present between nucleosomes, compared to bulk chromatin. Regulatory sequences are often located in linker DNA, to facilitate their ability to be bound by transcriptional regulators. Consequently, digestion of chromatin with MNase preferentially digests regions of chromatin that often include regulatory sites. Because MNase digests DNA between nucleosomes, differences in nucleosome positioning on specific sequences, between different cells, can be revealed by analysis of MNase digests of cellular chromatin using techniques such as, for example, indirect end-labeling, as described infra. Since alterations in nucleosome positioning are often associated with changes in gene regulation, sequences associated with changes in nucleosome positioning are likely to be regulatory sequences.

2. Establishing Boundaries of Digestion

Various methods, as are known to those of skill in the art, can be utilized to identify and map regions of cellular chromatin having altered reactivity to enzymatic and chemical probes, compared to bulk chromatin. For example, in methods in which accessible DNA is degraded by enzymatic and/or chemical cleavage agents, cleaved and deproteinized DNA can be used as a template for DNA sequence analysis with primers having known locations on a completely sequenced genome. Discontinuities in the sequence obtained with such a primer set indicate the boundaries of regulatory regions. For example, primers located at points 500–1,000 nucleotides apart (on both strands of a genome sequence) can be used for this type of analysis.

In another embodiment, the borders of accessible regions are localized utilizing the technique of indirect end-labeling. In this method, a collection of DNA fragments obtained as described above (i.e., reaction of nuclei or cellular chromatin with a probe or cleavage agent followed by deproteinization) are digested with a restriction enzyme to generate restriction fragments that include the regions of interest. Such fragments are then separated by gel electrophoresis and blotted onto a membrane. The membrane is then hybridized with a labeled hybridization probe complementary to a short region at one end of the restriction fragment containing the region of interest. In the absence of an accessible region, the hybridization probe identifies the full-length restriction fragment. However, if an accessible region is present within the sequences defined by the restriction fragment, the hybridization probe identifies one or more DNA species that are shorter than the restriction fragment. The size of each additional DNA species corresponds to the distance between an accessible region and the end of the restriction fragment to which the hybridization probe is complementary. An example of this type of analysis, performed on the human EPO gene, is described further infra in Example 5, and representative results are shown in FIG. 2.

3. Mapping DNase Hypersensitive Sites Relative to a Gene of Interest

A rapid method for mapping DNase hypersensitive sites (which can correspond to boundaries of accessible regions) with respect to a particular gene involves ligation of an adapter oligonucleotide to the DNA ends generated by DNase action, followed by amplification using an adapter-specific primer and a gene-specific primer. For this procedure, nuclei or isolated cellular chromatin are treated with a nuclease such as, for example, DNase I or micrococcal nuclease, and the chromatin-associated DNA is then purified. Purified, nuclease-treated DNA is optionally treated so as to generate blunt ends at the sites of nuclease action by, for example, incubation with T4 DNA Polymerase and the four deoxyribonulceoside triphosphates. After this treatment, a partially double-stranded adapter oligonucleotide is ligated to the DNA ends. The adapter contains a 5'-hydroxyl group at its blunt end and a 5'-extension, terminated with a 5'-phosphate, at the other end. The 5'-extension is an integral number of nucleotides greater that one nucleotide, preferably greater than 5 nucleotides, preferably greater than 10 nucleotides, more preferably 14 nucleotides or greater. Alternatively, a 5'-extension need not be present, as long as one of the 5' ends of the adapter is unphosphorylated. This procedure generates a population of DNA molecules whose termini are defined by sites of nuclease action, with the aforementioned adapter ligated to those termini.

The DNA is then purified and subjected to amplification (e.g., PCR). One of the primers corresponds to the longer, 5'-phosphorylated strand of the adapter, and the other is complementary to a known site in the gene of interest or its vicinity. Amplification products are analyzed by, for example, gel electrophoresis. The size of the amplification product(s) indicates the distance between the site that is complementary to the gene-specific primer and the proximal border of an accessible region (in this case, a nuclease hypersensitive site). In additional embodiments, a plurality of second primers, each complementary to a segment of a different gene of interest, are used, to generate a plurality of amplification products. Additional details regarding certain aspects of this approach are set forth in Example 11 infra.

In additional embodiments, nucleotide sequence determination can be conducted during the amplification. Such sequence analyses can be conducted individually or in multiplex fashion.

While the foregoing discussion on mapping has referred primarily to certain nucleases, it will be clear to those skilled in the art that any enzymatic or chemical agent, or combination thereof, capable of cleavage in an accessible region, can be used in the mapping methods just described.

F. Footprinting

Yet another method for identifying regulatory regions in cellular chromatin is by in vivo footprinting, a technique in which the accessibility of particular nucleotides (in a region of interest) to enzymatic or chemical probes is determined. Differences in accessibility of particular nucleotides to a probe, in different cell types, can indicate binding of a transcription factor to a site encompassing those nucleotides in one of the cell types being compared. The site can be isolated, if desired, by standard recombinant methods. See Wassarman and Wolffe (eds.) Methods in Enzymology, Volume 304, Academic Press, San Diego, 1999.

G. Variations

1. Isolation of Non-Accessible Regions

As those skilled in the art will readily recognize, certain of the methods described supra also generate collections of fragments comprising non-accessible regions of cellular chromatin. For example, in those instances in which an enzymatic or chemical probe is used to mark the accessible regions, the non-accessible regions correspond to those fragments that are unmarked. In the case of limited digestion with a nuclease such as DNase, the bulk chromatin or large fragments of DNA remaining after a small fragment from an accessible region is excised can correspond to non-accessible regions. In like manner, when a nonmethylated CpG island-containing fragment is cleaved from chromatin or naked DNA, the remaining DNA corresponds to non-accessible regions. As with the accessible regions, the non-accessible regions can be isolated and/or cloned to generate one or more libraries and/or analyzed (e.g., nucleotide sequence determined). In those instances in which the genome sequence is known, mapping non-accessible regions onto the genome sequence allows one to identify accessible regions.

2. In Vitro v. In Vivo Methods

Certain methods can optionally be performed in vitro or in vivo. For instance, treatment of cellular chromatin with chemical or enzymatic probes can be accomplished using isolated chromatin derived from a cell, and contacting the isolated chromatin with the probe in vitro. Methods which depend on methylation status can, if desired, be performed in vitro using naked genomic DNA. Alternatively, isolated nuclei can be contacted with a probe in vivo. In certain other in vivo methods, a probe can be introduced into living cells. Cells are permeable to some probes. For other probes, such as proteins, various methods, known to those of skill in the art, exist for introduction of macromolecules into cells. Alternatively, a nucleic acid encoding an enzymatic probe, optionally in a vector, can be introduced into cells by established methods, such that the nucleic acid encodes an enzymatic probe that is active in the cell in vivo. Methods for the introduction of proteins and nucleic acids into cells are known to those of skill in the art and are disclosed, for example, in co-owned PCT publication WO 00/41566. Methods for methylating chromatin in vivo using recombinant constructs are described, for example, by Wines, et al. (1996) Chromasoma 104:332–340; Kladde, et al. (1996) EMBO J. 15: 6290–6300, and van Steensel, B. and Henikoff, S. (2000) Nature Biotechnology 18:424–428, each of which is incorporated by reference in its entirety. It is also possible to introduce constructs into a cell to express a protein that cleaves the DNA such as, for example, a nuclease or a restriction enzyme.

3. Deproteinization

As described in the various isolation schemes supra, with certain methods it is desirable or necessary to deproteinize the chromatin or chromatin fragments. This can be accomplished utilizing established methods that are known to those of skill in the art such as, for example, phenol extraction. Various kits and reagents for isolation of genomic DNA can also be used and are available commercially, for example, those provided by Qiagen (Valencia, Calif.).

4. DNase Hypersensitive Mapping to Confirm Identification of Accessible Regions

As disclosed supra, accessible regions can be identified by an number of methods. Collections of accessible region sequences from a particular cell can be cloned to generate a library, and the nucleotide sequences of the members of the library can be determined to generate a database specific to the cell from which the accessible regions were obtained. Confirmation of the identification of a cloned insert in a library as comprising an accessible region is accomplished, if desired, by conducting DNase hypersensitive site mapping in the vicinity of any accessible region sequence obtained by the methods disclosed herein. Co-localization of a particular insert sequence with a DNase hypersensitive site validates the identity of the insert as an accessible regulatory region. Once a suitable number of distinct inserts are confirmed to reside within DNase hypersensitive sites in vivo, larger-scale sequencing and annotation projects can be initiated. For example, a large number of library inserts can be sequenced and their map locations determined by comparison with genome sequence databases. For a given accessible region sequence, the closest ORF in the genome is provisionally assigned as the target locus regulated by sequences within the accessible region. In this way, a large number of ORFs (open reading frames) in the genome acquire one or more potential regulatory domains, the function of which can be confirmed by standard procedures (see infra).

It will be apparent that certain of the methods described herein can be used in combination to provide confirmation and additional information. For example, treatment of nuclei or cellular chromatin with DNase can be followed by both isolation of solubilized DNA fragments (which comprise accessible region sequences) and mapping of the sites of DNase action by any of the methods described herein.

IV. Libraries of Accessible or Non-Accessible Polynucleotides and Sequence Determination A. Library Formation The isolated accessible regions can be used to form libraries of accessible regions; generally the libraries correspond to regions that are accessible for a particular cell. As used herein, the term "library" refers to a pool of DNA fragments that have been propagated in some type of a cloning vector.

Accessible regions isolated by methods disclosed herein can be cloned into any known vector according to established methods. In general, isolated DNA fragments are optionally cleaved, tailored (e.g., made blunt-ended or subjected to addition of oligonucleotide adapters) and then inserted into a desired vector by, for example, ligase- or topoisomerase-mediated enzymatic ligation or by chemical ligation. To confirm that the correct sequence has been inserted, the vectors can be analyzed by standard techniques such as restriction endonuclease digestion and nucleotide sequence determination.

Additional cloning and in vitro amplification methods suitable for the construction of recombinant nucleic acids are well-known to persons of skill in the art. Examples of these techniques and instructions sufficient to direct persons of skill through many cloning techniques are found in Berger and Kimmel, Guide to Molecular Cloning Techniques, Methods in Enzymology, Volume 152, Academic Press, Inc., San Diego, Calif. (Berger); Current Protocols in Molecular Biology, F. M. Ausubel et al., eds., Current Protocols in Molecular Biology, a joint venture between Greene Publishing Associates, Inc. and John Wiley & Sons, Inc., (1987 and periodic updates) (Ausubel); and Sambrook, et al. (1989) Molecular Cloning: A Laboratory Manual, 2nd ed., each of which is incorporated by reference in its entirety.

A variety of common vector backbones are well-known in the art. For cloning in bacteria, common vectors include pBR322 and vectors derived therefrom, such as pBLUESCRIPT™, the pUC series of plasmids, as well as λ-phage derived vectors. In yeast, vectors which can be used include Yeast Integrating plasmids (e.g., YIp5) and Yeast Replicating plasmids (the YRp series plasmids), the pYES series and pGPD-2 for example. Expression in mammalian cells can be achieved, for example, using a variety of commonly available plasmids, including pSV2, pBC12BI, and p91023, the pCDNA series, pCMV1, pMAMneo, as well as lytic virus vectors (e.g., vaccinia virus, adenovirus), episomal virus vectors (e.g., bovine papillomavirus), and retroviral vectors (e.g., murine retroviruses). Expression in insect cells can be achieved using a variety of baculovirus vectors, including pFastBac1, pFastBacHT series, pBluesBac4.5, pBluesBacHis series, pMe1Bac series, and pVL1392/1393, for example. Additional vectors and host cells are well-known to those of skill in the art.

The libraries formed can represent accessible regions for a particular cell type or cellular condition. Thus, different libraries can represent, for example, accessible regions for: cells that express a gene of interest at a high level, cells that express a gene of interest at a low level, cells that do not express a gene of interest, healthy cells, diseased cells, infected cells, uninfected cells, and/or cells at various stages of development. Alternatively or in addition, such individual libraries can be combined to form a collection of libraries. Essentially any number of libraries can be combined. Typically, a collection of libraries contains at least 2, 5 or 10 libraries, each library corresponding to a different type of cell or a different cellular state. For example, a collection of libraries can comprise a library from cells infected with one or more pathogenic agents and a library from counterpart uninfected cells. Determination of the nucleotide sequences of the members of a library can be used to generate a database of accessible sequences specific to a particular cell type.

In a separate embodiment, subtractive hybridization techniques can be used in the analysis of two or more collections of accessible sequences, obtained by any of the methods disclosed herein, to isolate sequences that are unique to one or more of the collections. For example accessible sequences from normal cells can be subtracted from accessible sequences present in virus-infected cells to obtain a collection of accessible sequences unique to the virus-infected cells. Conversely, accessible sequences from virus-infected cells can be subtracted from accessible sequences present in uninfected cells to obtain a collection of sequences that become inaccessible in virus-infected cells. Such unique sequences obtained by subtraction can be used to generate libraries and/or databases. Methods for subtractive hybridization and difference analysis are known to those of skill in the art and are disclosed, for example, in U.S. Pat. Nos. 5,436,142; 5,501,964; 5,525,471 and 5,958,738.

Analysis (e.g., nucleotide sequence determination) of libraries of accessible region sequences can be facilitated by concatenating a series of such sequences with interposed marker sequences, using methods similar to those described in U.S. Pat. Nos. 5,695,937 and 5,866,330.

B. High-Throughput Library Construction

Rapid, high-throughput construction of libraries of accessible regions can be achieved using a combination of nuclease digestion and ligation-mediated PCR. Pfeifer et al. (1993) Meth. In Mol. Biol. 15:153–168; Mueller et al. (1994) In: Current Protocols in Molecular Biology, ed. F. M. Ausubel et al., John Wiley & Sons, Inc., vol. 2, pp. 15.5.1–15.5.26. Nuclei or isolated cellular chromatin are subjected to the action of a nuclease such as, for example, DNase I or micrococcal nuclease, and the chromatin-associated DNA is purified and end-repaired using, for example, T4 DNA polymerase and the four deoxyribonulceoside triphosphates. A ligation reaction is conducted using, as substrates, the nuclease-digested, end-repaired chromosomal DNA and a double-stranded adapter oligonucleotide. The adapter has one blunt end, containing a 5'-phosphate group, which is ligated to the ends generated by nuclease action. The other end of the adapter oligonucleotide has a 3' extension and is not phosphorylated (and therefore is not capable of being ligated to another DNA molecule). In one embodiment, this extension is two bases long and has the sequence TT, although any size extension of any sequence can be used.

Adapter-ligated DNA is digested with a restriction enzyme which generates a blunt end. Preferably, the restriction enzyme has a four-nucleotide recognition sequence. Examples include, but are not limited to, Rsa I, Hae III, Alu I, Bst UI, and Cac81. Alternatively, DNA can be digested with a restriction enzyme that does not generate blunt ends, and the digested DNA can optionally be treated so as to produce blunt ends by, for example, exposure to T4 DNA Polymerase and the four deoxynucleoside triphosphates.

Next, a primer extension reaction is conducted, using Taq DNA polymerase and a primer complementary to the adapter. The product of the extension reaction is a double-stranded DNA molecule having the following structure: adapter sequence/nuclease-generated end/internal sequence/restriction enzyme-generated end/3 ' terminal A extension. The 3'-terminal A extension results from the terminal transferase activity of the Taq DNA Polymerase used in the primer extension reaction.

The end containing the 3'-terminal A extension (i.e., the end originally generated by restriction enzyme digestion) is joined, by DNA topoisomerase, to a second double-stranded adapter oligonucleotide containing a 3'-terminal T extension. In one embodiment, prior to joining, the adapter oligonucleotide is covalently linked, through the 3'-phosphate of the overhanging T residue, to a molecule of DNA topoisomerase. See, for example, U. S. Pat. No. 5,766,891. This results in the production of a molecule containing a first adapter joined to the nuclease-generated end and a second adapter joined to the restriction enzyme-generated end. This molecule is then amplified using primers complementary to the first and second adapter sequences. Amplification products are cloned to generate a library of accessible regions and the sequences of the inserts are determined to generate a database. Certain aspects of certain of the methods just described are described more fully in Example 12 below.

In the practice of the aforementioned method, it is possible to obtain DNA fragments in which both ends of the fragment have resulted from nuclease cleavage (N-N fragments). These fragments will contain both the first and second adapters on each end, with the first adapter internal to the second. Any given fragment of this type will theoretically yield four amplification products which, in sum, will be amplified twice as efficiently as a fragment having one nuclease-generated end and one restriction enzyme-generated end (N-R fragments). Thus, the final population of amplified material will comprise both N-N fragments and N-R fragments. Amplification using only one of the two primers will yield a population of amplified molecules that is enriched for N-N fragments (which will, under these conditions, be amplified exponentially, while N-R fragments will be amplified in a linear fashion). A population of amplification products enriched in N-R fragments can be obtained by subtracting the N-N population from the total population of amplification products. Methods for subtraction and subtractive hybridization are known to those of skill in the art. See, for example, U.S. Pat. Nos. 5,436,142; 5,501,964; 5,525,471 and 5,958,738.

In another embodiment, cellular chromatin is subjected to limited nuclease action, and fragments having one end defined by nuclease cleavage are preferentially cloned. For example, isolated chromatin or permeabilized nuclei are exposed to low concentrations of DNase I, optionally for short periods of time (e.g., one minute) and/or at reduced temperature (e.g., lower than 37° C.). DNase-treated chromatin is then deproteinized and the resulting DNA is digested to completion with a restriction enzyme, preferably one having a four-nucleotide recognition sequence. Deproteinization and restriction enzyme digestion are optionally conducted on DNA that has been embedded in agarose, to prevent shearing which would generate artifactual ends.

Preferential cloning of nuclease-generated fragments is accomplished by a number of methods. For example, prior to restriction enzyme digestion, nuclease-generated ends can be rendered blunt-ended by appropriate nuclease and/or polymerase treatment (e.g., T4 DNA polymerase plus the 4 dNTPs). Following restriction digestion, fragments are cloned into a vector that has been cleaved to generate a blunt end and an end that is compatible with that produced by the restriction enzyme used to digest the nuclease-treated chromatin. For example, if Sau 3AI is used for digestion of nuclease-treated chromatin, the vector can be digested with Bam HI (which generates a cohesive end compatible with that generated by Sau 3AI) and Eco RV or Sma I (either of which generates a blunt end).

Ligation of adapter oligonucleotides, to nuclease-generated ends and/or restriction enzyme-generated ends, can also be used to assist in the preferential cloning of fragments containing a nuclease-generated end. For example, a library of accessible sequences is obtained by selective cloning of fragments having one blunt end (corresponding to a site of nuclease action in an accessible region) and one cohesive end, as follows. Nuclease-treated chromatin is digested with a first restriction enzyme that produces a single-stranded extension to generate a population of fragments, some of which have one nuclease-generated end and one restriction enzyme-generated end and others of which have two restriction enzyme-generated ends. If this collection of fragments is ligated to a vector that has been digested with the first restriction enzyme (or with an enzyme that generates cohesive termini that are compatible with those generated by the first restriction enzyme), fragments having two restriction enzyme-generated ends will generate circular molecules, while fragments having a restriction enzyme-generated end and a nuclease-generated end will only ligate at the restriction enzyme-generated end, to generate linear molecules slightly longer than the vector. Isolation of these linear molecules (from the circular molecules) provides a population of sequences having one end generated by nuclease action, which thereby correspond to accessible sequences. Separation of linear DNA molecules from circular DNA molecules can be achieved by methods well-known in the art, including, for example, gel electrophoresis, equilibrium density gradient sedimentation, velocity sedimentation, phase partitioning and selective precipitation. The isolated linear molecules are then rendered blunt ended by, for example, treatment with a DNA polymerase (e.g., T4 DNA polymerase, *E. coli* DNA polymerase I Klenow fragment) optionally in the presence of nucleoside triphosphates, and recircularized by ligation to generate a library of accessible sequences.

An alternative embodiment for selective cloning of fragments having one nuclease-generated end and one restriction enzyme-generated end is as follows. After restriction enzyme digestion of nuclease-treated chromatin, protruding restriction enzyme-generated ends are "capped" by ligating, to the fragment population, an adapter oligonucleotide containing a blunt end and a cohesive end that is compatible with the end generated by the restriction enzyme, which reconstitutes the recognition sequence. The fragment population is then subjected to conditions that convert protruding ends to blunt ends such as, for example treatment with a DNA polymerase in the presence of nucleoside triphosphates. This step converts nuclease-generated ends to blunt ends. The fragments are then re-cleaved with the restriction enzyme to regenerate protruding ends on those ends that were originally generated by the restriction enzyme. This results in the production of two populations of fragments. The first (desired) population comprises fragments having one nuclease-generated blunt end and one restriction enzyme-generated protruding end; these fragments are derived from accessible regions of cellular chromatin. The second population comprises fragments having two restriction enzyme-generated protruding ends. Ligation into a vector containing one blunt end and one end compatible with the restriction enzyme-generated protruding end results in cloning of the desired fragment population to generate a library of accessible sequences. See Example 16.

An additional exemplary method for selecting against cloning of fragments having two restriction enzyme-generated ends involves ligation of nuclease-treated, restriction enzyme digested DNA to a linearized vector whose ends are compatible only with the ends generated by the restriction enzyme. For example, if Sau 3AI is used for restriction digestion, a Bam HI-digested vector can be used. In this case, fragments having two Sau 3AI ends will be inserted into the vector, causing recircularization of the linear vector. For fragments having a nuclease-generated end and a restriction enzyme-generated end, only the restriction enzyme-generated end will be ligated to the vector; thus the ligation product will remain a linear molecule. In certain embodiments, *E. coli* DNA ligase is used, since this enzyme ligates cohesive-ended molecules at a much higher efficiency than blunt-ended molecules. Separation of linear from circular molecules, and recovery of the linear molecules, generates a population of molecules enriched in the desired fragments. Such separation can be achieved, for example, by gel electrophoresis, dextran/PEG partitioning and/or spermine precipitation. Alberts (1967) *Meth. Enzymology* 12:566–581; Hoopes et al. (1981) *Nucleic Acids Res.* 9:5493–5504. End repair of the selected linear molecules, followed by recircularization, results in cloning of sequences adjacent to a site of nuclease action.

Size fractionation can also be used, separately or in connection with the other methods described above. For example, after restriction digestion, DNA is fractionated by gel electrophoresis, and small fragments (e.g., having a length between 50 and 1,000 nucleotide pairs) are selected for cloning.

In another embodiment, regulatory regions comprising unmethylated CpG island sequences are preferentially cloned by virtue of their susceptibility to digestion by Hpa II (see supra and Example 15, infra). Nuclei or cellular chromatin are exposed to brief Hpa II digestion, and the chromatin is deproteinized and digested to completion with a secondary restriction enzyme, preferably one that has a four-nucleotide recognition sequence. Deproteinization and restriction enzyme digestion are optionally conducted on DNA that has been embedded in agarose, to prevent shearing which would generate artifactual ends. Fragments containing one Hpa II end and one end generated by the secondary restriction enzyme are preferentially cloned into an appropriately digested vector. For example, if the secondary restriction enzyme is Sau 3AI, the vector can be digested with Cla I (whose end is compatible with a Hpa II end) and Bam HI (whose end is compatible with that generated by Sau 3AI), thus leading to selective cloning of Hpa II/Sau 3AI fragments, which contain unmethylated CpG island sequences.

Ligation of adapter oligonucleotides, as described supra, to Hpa II-generated ends and/or to the ends generated by the secondary restriction enzyme, can also be used to assist in the preferential cloning of fragments containing unmethylated CpG island sequences.

Size fractionation can also be used, separately or in connection with the other methods described above. For example, after digestion with the secondary restriction enzyme, DNA is fractionated by gel electrophoresis, and small fragments (e.g., having a length between 50 and 1,000 nucleotide pairs) are selected for cloning.

C. Sequencing

Purified and/or amplified DNA fragments comprising accessible regions can be sequenced according to known methods. In some instances, the isolated polynucleotides are cloned into a vector which is introduced into a host to amplify the sequence and the polynucleotide then purified from the cells and sequenced. Depending upon sequence length, cloned sequences can be rapidly sequenced using commercial sequencers such as the Prism 377 DNA Sequencers available from Applied Biosystems, Inc., Foster City, Calif.

V. Accessible Regions as Regulatory Regions

A. Identification of Regulatory Accessible Regions

A variety of techniques can be utilized to establish correspondence between a particular accessible region and the regulation of a gene of interest. Exemplary approaches are set forth below.

One method for determining whether an accessible region is involved in the regulation of a gene of interest in a particular cell type is to identify the spectrum of accessible regions in a cell in which the gene of interest is expressed at a high level, and compare it to the spectrum of accessible regions in a cell in which the gene of interest is expressed at a low level. Sequences that are unique to either the high-expressing cell or the low expressing cell are candidate regulatory sequences for the gene of interest.

The comparison can be done in several ways. For instance, comparison of nucleotide sequences in databases of accessible region sequences from two cell types, one of which expresses the gene and the other of which does not (or one of which expresses the gene at a higher level than the other) can lead to the identification of one or more sequences that are unique to one cell or the other. A sequence which is unique to the cell type that expresses the gene at a high level is a candidate positive regulatory sequence. On the other hand, a sequence that is unique to the cell type that expresses the gene at a low level (or which does not express the gene) is a candidate negative regulatory sequence.

Another method of comparison involves mapping of accessible regions, using methods described supra. In this method, accessible regions are mapped in the vicinity of a gene of interest in different cell types that express different levels of the gene product. Accessible regions that are, for example, present in high-level expressers and absent in low-level expressers are candidate positive regulatory regions for the gene of interest. Regulatory function of sequences within the accessible region can be confirmed by reporter assays, mutagenesis, and other methods known to those of skill in the art.

As an example, analysis of DNase I hypersensitive regions in the VEGF-A gene was conducted (FIGS. 8, 9 and 10). FIG. 9 provides a summary of DNase hypersensitivity data for the VEGF gene in different cell types. The data indicate that an accessible region centered around −1,000 base pairs (with respect to the transcriptional startsite) is unique to the U87MG cell line, which is also the highest expresser of VEGF, indicating that activation of VEGF gene transcription involves sequences within the accessible region at −1,000 (See Example 13 and FIG. 10).

FIG. 9 also shows that regions centered around −450 and +1 are accessible in cells regardless of their level of VEGF expression. These regions may represent entry or "gateway" sites that are loci of initial interaction of both positive and negative regulators of VEGF expression. For example, binding of one or more factors at the −450 and/or +1 site(s) may facilitate modification of chromatin structure in the −1,000 region, allowing binding of a factor which activates VEGF transcription.

Thus, sequences of accessible regions that are unique to a cell that expresses high levels of a gene of interest ("functional accessible sequences") are important for the regulation of that gene. Similarly, sequences of accessible regions that are unique to a cell expressing little or none of a particular gene product are also functional accessible sequences and can be involved in the repression of that gene.

In addition, the presence of tissue-specific regulatory elements in a gene provide an indication of the particular cell and tissue type in which the gene is expressed. Genes sharing a particular accessible site in a particular cell, and/or sharing common regulatory sequences, are likely to undergo coordinate regulation in that cell.

Furthermore, association of regulatory sequences with EST expression profiles provides a network of gene expression data, linking expression of particular ESTs to particular cell types.

An additional advantage of the present methods is that they assist in focusing effort on relevant regions of a genome. For example, most DNase I hypersensitive sites span approximately 200 nucleotide pairs and there are generally 5 to 10 hypersensitive sites within the 100 kilobase pairs potentially involved in the regulation of a gene. Thus, using the present methods, attention is focused on the sequences contained in the hypersensitive regions (1 to 2 kilobase pairs) as opposed to 100 kilobase pairs, which might have to be searched in the absence of information on functional regulatory sites (i.e., accessible sites).

B. Identification of Agents Affecting Regulatory Accessible Regions

Currently, the effect of a small molecule on gene expression is assayed by determining mRNA levels of the gene of interest, most often using microarray technology. However, these methods are expensive, require specialized technology and do not provide information about expression of non-coding structural RNAs. Moreover, they cannot be used to monitor the potential for gene activity in response to any given small molecule. The expression of non-coding RNAs and other modifications may have significant consequences for the regulation of expression of the associated gene in response to different signal transduction pathways independent of the actual transcription process.

Thus, described herein are methods of monitoring how one or more conditions, disease states or candidate effector molecules (e.g., drugs) affect the nature of accessible regions, particularly regulatory accessible regions. The term "nature of accessible regions" is used to refer to any characteristic of an accessible region including, but not limited to, the location and/or extent of the accessible regions and the degree of modification, for example acetylation or phosphorylation, of surrounding histones. To determine the effect of one or more drugs on these regions, accessible regions are compared between control (e.g., normal or untreated) cells and test cell (e.g., a diseased cell or a cell exposed to a candidate regulatory molecule such as a drug, a protein, etc.), using any of the methods described herein. Such comparisons can be accomplished with individual cells or, as described in Section VIII, using libraries of accessible regions. The unique and/or modified accessible regions can also be sequenced to determine if they contain any potential known regulatory sequences. In addition, the gene related to the regulatory accessible region(s) in test cells can be readily identified using methods described herein.

Thus, candidate regulatory molecules can also be evaluated for their direct effects on chromatin, accessible regions and/or gene expression, as described herein. Such analyses will allow the development of diagnostic, prophylactic and therapeutic molecules and systems.

When evaluating the effect of a disease or condition, normal cells are compared to cells known to have the particular condition or disease. Disease states or conditions of interest include, but are not limited to, cardiovascular disease, cancers, inflammatory conditions, graft rejection and/or neurodegenerative conditions. Similarly, when evaluating the effect of a candidate regulatory molecule on accessible regions, the locations of and/or modifications to accessible regions in any given cell can be evaluated before and after administration of a small molecule. As will be readily apparent from the teachings herein, concentration of the candidate small molecule and time of incubation can, of course, be varied. In these ways, the effect of the disease, condition, and/or small molecule on changes in chromatin structure (e.g., accessibility) and/or composition (e.g., acetylation, phosphorylation, methylation etc); or on transcription (e.g., through binding of RNA polymerase II) is monitored.

The methods are applicable to various cells, for example, human cells, animal cells, plant cells, fungal cells, bacterial cells, viruses and yeast cells. One example of use of these methods is in the case of human genes such as VEGF. As described herein regarding the VEGF gene, an accessible region centered around −1000 base pairs (FIG. 9) is unique to the U87MG cell line, the highest expresser of VEGF. All cell lines expressing VEGF were found to have accessible regions centered around −450 and +1 (Example 13 and FIGS. 8 and 9). Accordingly, candidate drugs can be tested for their effects on one or more of these accessible regions (common or unique), for instance, by determining if the candidate drug alters the chromatin structure at any of these accessible regions. If the candidate molecule is found to have effects on accessible regions, its effects on gene expression can also be determined.

Another example of the application of these methods is in diagnosis and treatment of human and animal pathogens (e.g., bacteria, viral or fungal pathogens). First, the location and nature of accessible regions is analyzed to determine genes involved in infection, maintenance and/or clearance of the pathogen. The analysis may be conducted in the host(s), the pathogen or both. For example, during infection of a host cell, pathogens such as chlamydia express genes encoding various surface antigens in order to attach themselves to the host. Analyzing the accessible regions in the genome of chlamydia will identify genes expressed during infection and will allow for evaluation of candidate molecules on these accessible regions and/or corresponding genes. Malaria provides yet another example where identification of unique or altered accessible regions in the pathogen or host allows for identification of drug targets and validation of drug effects. Malaria exists in at least two hosts (mosquito and human) and appears take different forms in different hosts. Thus, comparison of accessible regions in the malarial (Plasmodium) genome at various stages and in various hosts will help elucidate an understanding of these pathogens and develop regimes for diagnosis and/or treatment (e.g., prophylactically or (after infection).

These methods also allow for evaluation and manipulation of microorganisms used in bioreactor applications. For example, molecules can be tested for their effects on accessible regions and corresponding gene expression in microbial cells to help increase yield of certain gene products or, alternatively, to limit production of undesirable gene products (e.g., certain byproducts of yeast fermentation).

In yet other embodiments, the accessible regions are analyzed in plant cells. In a broad definition a plant is a multicellular photosynthetic eucaryote. A few plants are not photosynthetic and are typically parasitic species, such as Indian pipe. Such non-photosynthetic plants have typical plant organs (e.g., leaves, roots, flowers, etc.) but have adapted to have different nutrition sources (that is, other than photosynthesis). Plant cells typically have cell walls that contain cellulose as the major strengthening polysaccharide. Plant cells typically comprise chloroplasts which contain chlorophyll. Two broad classifications of plants include non-vascular plants (comprising three phyla, including, for example, mosses, liverworts, and hornworts) and vascular (comprising nine phyla). Vascular plants are a large and diverse group including seed producing (e.g., the angiosperms) and seedless plants. Typical organs of angiosperms include, but are not limited to, leaves, stems, root systems, flower petals, stamen (anthers, filaments), pistil (stigma, style, ovary). Flowering plants are divided into monocots and dicots that differ in plant body characteristics.

Standard manipulations of plants and plant cells are known in the art and can be used in the compositions and methods described herein in view of the teachings of the present specification. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Current Protocols In Molecular Biology*, (F. M. Ausubel et al. eds.).

Analysis of accessible regions in plant cells includes, but is not limited to, identifying accessible regions related to endogenous or exogenous genes, as well as genes which mediate tissue or organ specific expression, i.e., by comparison of accessible regions in cells derived from one plant tissue or organ compared to accessible regions in cells derived from a different plant tissue or organ. Further, accessible regions associated with response of plant cells to environmental challenges may also be evaluated by the methods described herein. Such environmental challenges include, but are not limited to, drought or dry environments, hyper- or hypo-salinity, oxygen rich versus oxygen poor, nutrient rich versus nutrient poor (e.g., for identifying essential plant nutrients), insect attack/resistance, fungal attack/resistance, bacterial attack/resistance, viral attack/resistance, parasite attack/resistance, and/or other disease pathology or resistance. Following the teachings disclosed herein, accessible regions related to genes which mediate increased herbicide resistance/sensitivity can be identified, as well as accessible regions associated with, for example, increased growth or yield, altered amounts or ratios of cell constituents (e.g., oils, carbohydrates, protein), altered levels of production of a chemical(s) substance(s) of interest, and altered levels of biochemicals being produced by a selected plant cell (e.g., vaccines encoded by transgenic plants).

In addition accessible regions associated with the regulation of plant development may also be evaluated. For example, accessible regions of a control group of untreated plant cells may be compared to accessible regions of an experimental group of plant cells that have been treated with plant hormones including but not limited to gibberellins, auxins, cytokinins, ethylene, brassinosteroids, jasmonic acid, salicylic acid, systemin and/or abscisic acid. Further accessible regions associated with the induction of meiosis may be identified.

As described above these targets are identified by evaluating accessible regions involved in these processes, and, optionally, testing the gene or genes related to the identified accessible region(s) for their role in the selected process.

VI. Methods for Design of Exogenous Regulatory Molecules

A. General

As used herein an "exogenous molecule," with respect to a particular cell, is any molecule that is not normally present in the cell. "Normal presence in the cell" is determined with respect to the particular developmental stage and environmental conditions of the cell. By contrast, an endogenous molecule is one that is normally present in a particular cell at a particular developmental stage under particular environmental conditions.

The ability to regulate an endogenous gene using an exogenous molecule has value in a variety of applications including therapeutics, diagnostics, target validation and W research. For instance, many pathophysiological processes are the result of aberrant gene expression. Examples include the inappropriate activation of proinflammatory cytokines in rheumatoid arthritis, under-expression of the hepatic LDL receptor in hypercholesteremia, over-expression of proangiogenic factors, and under-expression of antiangiogenic factors in solid tumor growth. If therapeutic methods for control of gene expression existed, many of these pathologies could be more optimally treated.

Other therapeutic utilities resulting from the ability to regulate gene expression include activating otherwise inactive genes to treat a particular disease state. Examples of possible therapeutic applications of gene reactivation include activation of developmentally silent fetal globin genes to treat sickle cell disease and the activation of the dystrophin and/or eutrophin genes to treat muscular dystrophy. In addition, pathogenic organisms such as viruses, bacteria, fungi, and protozoa can be controlled by altering gene expression. Accordingly, there is a need for improved therapeutic approaches that act through sequence-specific regulation of disease-related genes.

B. Design Aspects

One way in which regulation of an endogenous gene can be achieved is through the development of various exogenous molecules capable of binding to DNA and controlling expression of a particular gene of interest. In certain embodiments, a chimeric exogenous regulatory molecule comprises a fusion between a DNA-binding domain and a functional domain, either an activation domain or a repression domain. In a preferred embodiment, a DNA-binding domain comprises a zinc finger DNA-binding domain. Certain of the methods disclosed herein prove valuable in designing such exogenous molecules since the nucleotide sequence of an accessible region of cellular chromatin involved in the regulation of a gene of interest provides information about the normal cellular pathways active in the regulation of that gene. Based upon sequence information regarding regulatory sequences identified as described herein, exogenous regulatory molecules can be designed to include a binding component/domain that binds to identified accessible regulatory sequences and a functional component/domain that directly or indirectly affects expression of a gene. Such approaches can be used, for instance, to regulate a gene in a way that is different from the way in which the gene is normally regulated, or to correct pathologic mis-regulation of a gene by restoring its normal regulation.

For example, the sequence of an accessible region that is in the vicinity of a gene of interest can be scanned for the presence of binding sites for known transcription factors. If the accessible region is a functional accessible region, as defined above, the functional domains of the transcription factors that bind within the functional accessible region are good candidates for functional domains to be used for regulation of the gene by an exogenous molecule.

On the other hand, transcription factor binding sites within gateway accessible regions allow one to determine preferred DNA-binding domains to be included in a chimeric exogenous regulatory molecule, since they represent sites in the vicinity of a gene that are accessible regardless of the level of expression of the gene. Thus, gateway sequences are also useful as targets for the design of exogenous gene regulatory molecules.

Thus, an exemplary exogenous molecule for activation of the VEGF gene in HeLa cells is a fusion molecule comprising a DNA-binding domain targeted to a sequence in either the −450 or the +1 accessible regions (i.e. the gateway regions) fused to a transcriptional activation domain. More preferred is an exogenous molecule comprising a DNA-binding domain targeted to the −450 or the +1 gateway region fused to an AML-1 activation domain (FIG. 11). Such molecules can be introduced into the cells by methods known to those of skill in the art (see supra). Alternatively, synthetic DNA-binding domains can be designed to recognize sequences in a gateway accessible region.

Thus, an exemplary exogenous molecule for regulation of a gene of interest comprises a DNA-binding domain which recognizes a target site in a gateway accessible region of the gene and a functional domain that corresponds to that of a transcription factor that binds to a functional accessible region of the gene.

C. General Components

The exogenous molecules which can be designed based upon the sequence information provided according to the methods disclosed herein include, but are not limited to, macromolecules such as proteins, nucleic acids, lipids and polysaccharides, as well as small molecules such as those that might be generated combinatorial chemistry. See, for example, WO 93/06121; WO 94/08051; WO 95/12608; WO 95/30642; and WO 95/35503. Nucleic acids include RNA and DNA; can be single- or double-stranded; can be linear, branched or circular; and can be of any length. Nucleic acids include those capable of forming duplexes and those capable of forming triplex structures with double-stranded DNA. See, for example, U. S. Pat. Nos. 5,422,251 and 5,176,996.

The aforementioned categories of exogenous molecules include analogues and modified variants. For example, nucleic acids can include modified bases, sugars and/or internucleotide linkages. Nucleic acid analogues include polyamide (peptide) nucleic acids and chimeric molecules comprising PNA and/or DNA and/or RNA. See, for example, Nielsen et al. (1991) Science 254:1497–1500; Uhlmann (1998) Biol. Chem 379:1045–1052. DNA/RNA hybrids and DNA/RNA chimeras are also included. Protein analogues include those comprising modifications such as, for example, acetylation, phosphorylation and myristylation, as well as those containing non-naturally-occurring amino acids, amino acid variants and/or non-peptide inter-amino acid linkages.

Exogenous nucleic acids can be either integrated or episomal, and can be either stably or transiently present in the cell.

Although the type of exogenous molecule that can be designed can vary widely, in general, the exogenous molecules that are designed to interact with the regulatory sequences identified by the methods disclosed herein typically contain certain elements. Such elements or components include, but are not limited to, a DNA-binding domain and a functional domain.

1. DNA Binding Component

The DNA binding component can be selected using established criteria based upon the identified regulatory sequence. See, for example, Wingender et al, supra. In certain embodiments, a DNA-binding component of an exogenous regulatory molecule comprises one or more zinc finger DNA-binding domains. Methods for designing zinc finger protein (ZFP) DNA-binding domains to recognize a polynucleotide sequence of interest have been disclosed in various patents and in the scientific literature. See, e.g., U.S. Pat. Nos. 5,789,538; 6,007,988; 6,013,453; WO 95/19431; WO 98/53057; WO 98/53058; WO 98/53059; WO 98/53060; WO 98/54311; WO99/45132; WO99/47656; WO99/48909; WO00/23464; WO00/42219; co-owned U.S. patent application Ser. No. 09/444,241 filed Nov. 19, 1999; co-owned U.S. patent application Ser. No. 09/535,088, filed Mar. 23, 2000; Rebar et al. (1994) Science 263:671–673; Jamieson et al. (1994) Biochemistry 33:5689–5695; Choo et al. (1994) Proc. Natl. Acad. Sci USA 91:11163–11167; Jamieson et al. (1996) Proc. Natl. Acad. Sci USA 93:12, 834–12,839; and Greisman et al. (1997) Science 275:657–661, each of which is incorporated by reference in its entirety.

2. Functional Domain

The functional component/domain can be selected from any of a variety of different components capable of influencing transcription of a gene once the exogenous molecule binds to an identified regulatory sequence via the DNA binding domain of the exogenous molecule. Hence, the functional component can include, but is not limited to, various transcription factor domains, such as activators, repressors, co-activators, co-repressors, and silencers.

An exemplary domain for fusing with a ZFP when the ZFP is to be used for repressing expression of a target gene is a KRAB repression domain from the human KOX-1 protein (see, e.g., Thiesen et al., New Biologist 2, 363–374 (1990); Margolin et al., Proc. Natl. Acad. Sci. USA 91, 4509–4513 (1994); Pengue et al., Nucl. Acids Res. 22:2908–2914 (1994); Witzgall et al., Proc. Natl. Acad. Sci. USA 91, 4514–4518 (1994). Suitable domains for achieving activation include the HSV VP16 activation domain (see, e.g., Hagmann et al., J. Virol. 71, 5952–5962 (1997)) nuclear hormone receptors (see, e.g., Torchia et al., Curr. Opin. Cell. Biol. 10:373–383 (1998)); the p65 subunit of nuclear factor kappa B (Bitko & Barik, J. Virol. 72:5610–5618 (1998)and Doyle & Hunt, Neuroreport 8:2937–2942 (1997)); Liu et al., Cancer Gene Ther. 5:3–28 (1998)), or artificial chimeric functional domains such as VP64 (Seifpal et al., EMBO J. 11, 4961–4968 (1992)).

Additional exemplary activation domains include, but are not limited to, VP16, VP64, p300, CBP, PCAF,SRC1 PvALF, AtHD2A and ERF-2. See, for example, Robyr et al. (2000) Mol. Endocrinol. 14:329–347; Collingwood et al. (1999) J. Mol. Endocrinol. 23:255–275; Leo et al. (2000) Gene 245:1–11; Manteuffel-Cymborowska (1999) Acta Biochim. Pol. 46:77–89; McKenna et al. (1999) J. Steroid Biochem. Mol. Biol. 69:3–12; Malik et al. (2000) Trends Biochem. Sci. 25:277–283; and Lemon et al. (1999) Curr. Opin. Genet. Dev. 9:499–504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21–29; Okanami et al. (1996) Genes Cells 1:87–99; Goff et al. (1991) Genes Dev. 5:298–309; Cho et al. (1999) Plant Mol. Biol. 40:419–429; Ulmason et al. (1999) Proc. Natl. Acad. Sci. USA 96:5844–5849; Sprenger-Haussels et al. (2000) Plant J. 22:1–8; Gong et al. (1999) Plant Mol. Biol. 41:33–44; and Hobo et al. (1999) Proc. Natl. Acad. Sci. USA 96:15,348–15,353.

Additional exemplary repression domains include, but are not limited to, KRAB, SID, MBD2, MBD3, members of the DNMT family (e.g., DNMT1, DNMT3A, DNMT3B), Rb, and MeCP2. See, for example, Bird et al. (1999) Cell 99:451–454; Tyler et al. (1999) Cell 99:443–446; Knoepfler et al. (1999) Cell 99:447–450; and Robertson et al. (2000) Nature Genet. 25:338–342. Additional exemplary repression domains include, but are not limited to, ROM2 and AtHD2A. See, for example, Chem et al. (1996) Plant Cell 8:305–321; and Wu et al. (2000) Plant J 22:19–27.

Additional functional domains are disclosed, for example, in co-owned WO 00/41566.

3. Transfer Component

The exogenous molecule can optionally be designed to include a component/domain that enables the exogenous molecule to be transferred across the plasma membrane. This is of importance since cellular membranes are composed of lipid-protein bilayers that are impermeable to polar compounds and macromolecules such as proteins. However, various proteins and liposomes have been shown capable of translocating proteins.

For example, "membrane translocation polypeptides" have amphiphilic or hydrophobic amino acid subsequences that have the ability to act as membrane-translocating carriers. Such polypeptides include, but are not limited to, certain regions of homeodomain proteins and the h (hydrophobic domain) of signal peptides (see, e.g., Prochiantz, Current Opinion in Neurobiology 6:629–634 (1996); and Lin et al., J. Biol. Chem. 270:1 4255–14258 (1995)). Other peptide sequences that can be used to facilitate uptake include, for example, an 11 amino acid peptide of the tat protein of HIV; a 20 residue peptide sequence which corresponds to amino acids 84–103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223–233 (1997)).

Toxin molecules also have the ability to transport polypeptides across cell membranes. See, e.g., Arora et al., J. Biol. Chem., 268:3334–3341 (1993); Perelle et al., Infect. Immun., 61:5147–5156 (1993); Stenmark et al., J. Cell Biol. 113:1025–1032 (1991); Donnelly et al., PNAS 90:3530–3534 (1993); Carbonetti et al., Abstr. Annu. Meet. Am. Soc. Microbiol. 95:295 (1995); Sebo et al., Infect. Immun. 63:3851–3857 (1995); Klimpel et al., PNAS U.S.A. 89:10277–10281(1992); and Novak et al., J. Biol. Chem. 267:17186–17193 (1992).

Typically, the transfer component is provided as part of a fusion protein. Optionally, a linker can be used to link the transfer component to the remainder of the exogenous molecule. Any suitable linker can be used, e.g., a peptide linker.

D. Preparation

Polypeptides and nucleic acids encoding the same can be made using routine techniques in the field of recombinant genetics. Basic texts disclosing general recombinant methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1987 and periodic updates). Any suitable method of protein purification known to those of skill in the art can be used to purify those exogenous molecules that are proteins (see, Ausubel, supra, Sambrook, supra). In addition, any suitable host can be used for expression, e.g., bacterial cells, insect cells, yeast cells, mammalian cells, and the like.

Oligonucleotides, for use in the construction of genes encoding exogenous molecules, can be chemically synthesized according to the solid phase phosphoramidite triester method first described by Beaucage & Caruthers, Tetrahedron Letts. 22:1859–1862 (1981), and/or using an automated synthesizer, as described in Van Devanter et al., Nucleic Acids Res. 12:6159–6168 (1984). Purification of oligonucleotides is by either denaturing polyacrylamide gel electrophoresis or by reverse phase HPLC. The nucleotide sequence of cloned genes encoding exogenous molecules and/or synthetic oligonucleotides used in their construction can be verified after cloning using nucleotide sequencing methods known to those of skill in the art such as, e.g., the Sanger chain termination method.

VII. Methods for the Design of Vectors Carrying Transgenes

A. General

In order to achieve tissue-specific, copy number-dependent, position-independent, regionally-specific and temporally appropriate gene activity, concerted action of many regulatory DNA sequences is required. Knowledge of the regulatory sequences that regulate particular genes in particular cells as determined according to the methods described herein can be utilized in the design of efficient vector systems for developmentally-, temporally-, and regionally-correct gene expression.

Thus, in general, certain methods directed towards the design of vectors containing transgenes involves inserting one or more regulatory sequences (which can include any or all of the following: locus control regions, enhancers, promoters, boundary elements and matrix attachment regions) as identified according to the methods herein into a vector such that the regulatory sequence(s) is (are) operatively linked to a selected transgene. For example, knowledge of regulatory sequences that mediate expression of a liver-specific gene allows the design of vectors that effectively express transgenes (e.g., therapeutic genes) in the liver, by assembly of one or more liver-specific regulatory elements in a vector also comprising a transgene. Using such a vector allows sustained expression of a transgene, even when the vector is stably integrated into cellular chromatin. Such liver-specific (for example) regulatory elements (and/or their nucleotide sequences) are obtained through identification of accessible regions in liver chromatin according the methods described supra. The formation of databases of accessible sites in a particular cell type, as disclosed herein, facilitates the task of selecting appropriate regulatory elements for inclusion in vectors (see infra).

The use of regulatory sequences that are native to, and active in, the cell into which the vector is introduced confers several advantages. First, such a strategy allows gene activation to be developmentally staged for therapeutic purposes by, for example, the use of a developmental stage-specific regulatory element identified according to the methods disclosed herein. Regional targeting of gene expression is also enhanced by the use of appropriate regulatory elements identified as disclosed herein. Furthermore, the design of vectors in this manner facilitates the ability of transgenes to evade the robust host defense pathways operative in plant and animal cell nuclei such as cellular pathways that recognize foreign DNA (especially cDNAs driven by strong viral promoters, such as are used in many contemporary vectors) and assemble it into heterochromatin (i.e., inactive chromatin). Appropriate inclusion, into vectors, of sequences such as insulators and boundary elements can help counter position effects that lead to silencing of transgenes based on their site of integration. Thus, more sustained and less toxic levels of gene activity are obtained.

B. Vector Structure and Construction

1. Regulatory Elements

Initially, one undertakes a study to identify regulatory sequences active in the particular cell type to which a vector is to be delivered. Such sequences can be identified according to the techniques set forth above. Once such regulatory sequences have been so identified, one or more of the identified regulatory sequences are inserted into a vector capable of expressing the gene in the cells of interest using recombinant techniques that are well-established in the art. The regulatory sequence (or sequences) is inserted into the vector such the regulatory sequence is operatively linked to the transgene, thereby forming an expression cassette.

Various regulatory sequences other than the identified regulatory sequences can be inserted. The expression cassette includes a promoter, which can be specific to the particular type of cell or tissue to which the vector is to be delivered, or can be non-cell-specific (e.g., CMV, RSV and SV40). As noted supra, other potential regulatory sequences that can be included within the vector include, but are not limited to, enhancers, locus control regions, boundary elements, matrix attachment regions and replication origins.

In construction of recombinant vectors, a plant transcriptional regulatory sequence may be employed which will direct expression of the gene in all tissues of a regenerated plant. Such promoters are referred to herein as "plant constitutive" promoters or "non-tissue-specific" promoters. Typically constitutive promoters are active under most environmental conditions and states of development or cell differentiation. Examples of constitutive promoters include, but are not limited to, the ubiquitin promoter (e.g., from soybean and rice), the cauliflower mosaic virus (CaMV) 35S transcription initiation region (e.g., U.S. Pat. No. 5,352,605 Fraley, et al. Oct. 4, 1994), and the T-DNA mannopine synthetase promoter (e.g., the 1'- or 2'-promoter derived from T-DNA of Agrobacterium tumefaciens).

Alternately, transcriptional regulatory sequences may direct expression of an associated polynucleotide in a specific tissue (tissue-specific promoters) or may be otherwise under more precise environmental control (e.g., some inducible promoters). Examples of tissue-specific promoters include promoters that initiate transcription only in certain tissues, such as fruit, seeds, or flowers. Tissue- or developmental-specific promoters, include, but are not limited to, the CHS promoter, the PATATIN promoter, and the tissue specific E8 promoter from tomato, which is particularly useful for directing gene expression so that a desired gene product is located in fruits.

Other transcriptional regulatory sequences include those from genes encoding embryonic storage proteins. Examples of environmental conditions that may affect transcription by inducible promoters include anaerobic conditions, elevated temperature, or the presence of light. For proper polypeptide expression, a polyadenylation region at the 3'-end of the coding region is typically included. The polyadenylation region can be derived, for example, from a variety of naturally occurring plant genes, or from T-DNA.

Plant transcriptional regulatory sequences include but are not limited to the promoters derived from the genome of plant cells (e.g., heat shock promoters such as soybean hsp17.5-E or hsp17.3-B, e.g., Gurley et al. (1986) *Mol. Cell. Biol.* 6:559–565); the promoter for the small subunit of RUBISCO (e.g., Coruzzi et al. (1984) *EMBO J.* 3:1671–1680; Broglie et al (1984) Science 224:838–843); or from plant viral promoters such as the 35S RNA and 19S RNA promoters of CaMV (e.g., Brisson et al. (1984) *Nature* 310:511–514), or the coat protein promoter of TMV (e.g., Takamatsu et al. (1987) *EMBO J.* 6:307–311). In addition, some non-plant promoters function in plant cells as well, including, but not limited to human cytomegalovirus hCMV immediate early gene, the early or late promoters of SV40 and adenovirus, and the promoters of the yeast alpha-mating factors. Other plant promoters commonly used to mediate expression of heterologous polypeptide sequences in plant cells are octopine T-DNA promoters (e.g., U.S. Pat. No. 5,428,147, Barker, et al., issued Jun. 27, 1995), and figwort mosaic virus-derived promoters (e.g., U.S. Pat. No. 6,051,753, Comai, et al., issued Apr. 18, 2000). Further, expression of some sequences may be enhanced in a selected plant type or cell by employing codon optimization (e.g., U.S. Pat. No. 5,082,767, Hatfield, et al., issued Jan. 21, 1992). For example, a method for producing a plant-optimized nucleic acid coding sequence in maize (a monocot) is disclosed in U.S. Pat. No. 6,121,014, Koziel, et al., issued Sep. 19, 2000).

2. Vectors

Any of a number of vectors can be utilized. The vectors can be capable of replication in a variety of cell types, or can be specific to one or more particular cell types. Exemplary vectors are known to those of skill in the art and are disclosed, for example in co-owned WO 00/41566.

For expression in plants a coding sequence is preferably combined with transcriptional and translational regulatory sequences which will direct the expression of the coding sequence in the intended tissues of the transgenic plant. These sequences are typically combined into a vector backbone (e.g., as described in U.S. Pat. No. 5,783,394, Bestwick, et al. Jul. 21, 1998; U.S. Pat. No. 5,866,787, Silverman, et al. Feb. 2, 1999; U.S. Pat. No. 5,939,601, Klessig, et al. Aug. 17, 1999; U.S. Pat. No. 5,952,489, Okada, et al. Sep. 14, 1999).

The vector comprising the sequences (e.g., promoters or coding regions) typically further comprise a marker gene which confers a selectable phenotype on plant cells. For example, the marker may encode biocide resistance, particularly antibiotic resistance, such as resistance to kanamycin, G418, hygromycin, bleomycin, or herbicide resistance, such as resistance to chlorosluforon or Basta. See, for example, use of G418 and Hygromycin B (U.S. Pat. No. 4,727,028, Santerre, et al., issued Feb. 23, 1988); positive selection using other than a toxin, an antibiotic or herbicide resistance (U.S. Pat. No. 5,994,629, Bojsen, et al., issued Nov. 30, 1999); phosphinothricin-resistance (U.S. Pat. No. 5,276,268, Strauch, et al., issued Jan. 4, 1994); and hygromycin phosphotransferase (aphIV) gene from *Escherichia coli* (U.S. Pat. No. 6,048,730, Waldron, issued Apr. 11, 2000).

3. Transgene

A transgene in general refers to any exogenous gene that can be inserted into a vector and expressed in the cell type of interest. Certain transgenes are selected to compensate for a defect in an endogenous gene, with the goal of incorporating a functional copy of the gene into the host genome. Often diseases amendable to such treatment are characterized by recessive mutations (i.e., both copies of an endogenous gene must be defective for symptoms to appear). Hence, the transgene can be a therapeutic gene that counteracts some malady associated with certain cells or all cells in an organism.

Alternatively, the transgene can include the gene for an immunogenic epitope for certain infectious organisms; expression of the gene triggers an immune response to protect against subsequent infection. A transgene can include, for example, a tumor suppressor gene if the vector is to be introduced into cancerous cells (see, e.g., U.S. Pat. No. 5,532,220). Expression of a tumor suppressor gene can slow, stop or reverse cellular proliferation and other manifestations of a cancerous state. The transgene can also be, for example, a drug-resistance gene. Any therapeutically-relevant gene can be used as a transgene in the vectors disclosed herein.

C. Administration of Vector

Once the vectors have been designed, a variety of options are available for administering the vector to an individual. In some instances, the vector is administered as a composition in a buffered solution or, optionally, as a component in a lotion or cream. Such compositions can include, depending upon the particular formulation desired, various pharmaceutically acceptable carriers or diluents (see, e.g., Remington's Pharmaceutical Sciences (1985) Mace Publishing Company, Philadelphia, Pa., 17th ed.) Another option is to administer the vector by a gene gun. In general, this approach involves precipitating the vector of interest onto the surface of a microscopic metal bead to generate a microprojectile that can be accelerated by shock wave or expanding gas to penetrate tissue. DNA vectors can also be administered using liposomes. A variety of liposome composition suitable for administration of the designed vectors are commercially available from a number of different vendors.

Additional methods of administration of vectors are known to those of skill in the art and are disclosed, for example, in co-owned WO 00/41566.

DNA constructs may be introduced into the genome of the desired plant or plant cells by a variety of conventional techniques. See, for example, Weissbach & Weissbach *Methods for Plant Molecular Biology* (1988, Academic Press, N.Y.) Section VIII, pp. 421–463; and Grierson & Corey, *Plant Molecular Biology* (1988, 2d Ed.), Blackie, London, Ch. 7–9. For example, a DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70–73). Alternatively, the DNA constructs may be combined with T-DNA flanking regions and introduced into a conventional Agrobacterium tumefaciens host vector. Agrobacterium tumefaciens-mediated transformation techniques, including disarming and use of binary vectors, have been described. See, for example Horsch et al (1984) *Science* 233:496–498; Fraley et al (1983) *Proc. Nat'l. Acad. Sci. USA* 80:4803; Bevan (1984) *Nuc. Acid Res.* 12:8711–8721; and Horsch et al (1985) *Science* 227:1229–1231. Generally, the Agrobacterium transformation system is used to engineer dicotyledonous plants (Bevan et al (1982) *Ann. Rev. Genet* 16:357–384; Rogers et al (1986) *Methods Enzymol.* 118:627–641). However, the Agrobacterium transformation system may also be used to manipulate monocotyledonous plants and plant cells. See, for example, Hernalsteen et al (1984) *EMBO J* 3:3039–3041; Hooykass-Van Slogteren et al (1984) *Nature* 311:763–764; Grimsley et al (1987) *Nature* 325:1677–179; Boulton et al (1989) *Plant Mol. Biol.* 12:31–40.; and Gould et al (1991) *Plant Physiol.* 95:426–434.

Thus, gene transfer and transformation methods for use with plant cells include, but are not limited to, protoplast transformation through calcium-, polyethylene glycol (PEG)- or electroporation-mediated uptake of naked DNA (see Paszkowski et al. (1984) *EMBO J* 3:2717–2722, Potrykus et al. (1985) *Molec. Gen. Genet.* 199:169–177; Fromm et al. (1985) *Proc. Nat. Acad. Sci. USA* 82:5824–5828; and Shimamoto (1989) *Nature* 338:274–276) and electroporation of plant tissues (D'Halluin et al. (1992) *Plant Cell* 4:1495–1505). Additional methods for plant cell transformation include microinjection, silicon carbide mediated DNA uptake (Kaeppler et al. (1990) *Plant Cell Reporter* 9:415–418), and microprojectile bombardment (see Klein et al. (1988) *Proc. Nat. Acad. Sci. USA* 85:4305–4309; and Gordon-Kamm et al. (1990) *Plant Cell* 2:603–618).

Transformed plant cells produced by any transformation technique typically can be cultured to regenerate a whole plant possessing the transformed genotype and, accordingly, the desired phenotype. Plant regeneration from cultured protoplasts is described in Evans, et al., "Protoplasts Isolation and Culture" in *Handbook of Plant Cell Culture*, pp. 124–176, Macmillian Publishing Company, New York, 1983; and Binding, *Regeneration of Plants, Plant Protoplasts*, pp. 21–73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467–486.

A wide variety of plants and plant cell systems may be manipulated as described herein. In preferred embodiments, target plants and plant cells include, but are not limited to, monocotyledonous and dicotyledonous plants, such as crops including grain crops (e.g., wheat, maize, rice, millet, barley); fruit crops (e.g., tomato, apple, pear, strawberry, orange); forage crops (e.g., alfalfa); root vegetable crops (e.g., carrot, potato, sugar beets, yam); leafy vegetable crops (e.g., tobacco, lettuce, spinach); flowering plants (e.g., petunia, rose, chrysanthemum); conifers and pine trees (e.g., pine fir, spruce); woody plants (e.g., raspberry, blackberry); plants used in phytoremediation (e.g., heavy metal accumulating plants); oil crops (e.g., sunflower, rape seed); multiple use food sources (e.g., soy); and plants used for experimental purposes (e.g., Arabidopsis).

One of skill in the art will recognize that after a polynucleotide of interest has been stably incorporated in a transgenic plant and is confirmed to be operable, it can be introduced into other plants by sexual crossing. Any of a number of standard breeding techniques can be used, depending upon the species to be crossed. Further, progeny, seeds, clones, cell lines or cells may be obtained from such transgenic plants.

VIII. Uses of Libraries and Databases of Accessible Regions

Collections of sequences corresponding to accessible regions can be utilized to conduct a variety of different comparisons to obtain information on the regulation of cellular transcription. Such collections of sequences can be obtained as described supra. Sequence comparisons can be performed visually if the number of sequences is relatively limited and the length of the sequences relatively short (see, e.g., Current Protocols in Molecular Biology (1995 Supplement) F. M. Ausubel, et al. Eds., in Current Protocols, a joint venture between Greene Publishing Associates, Inc. and John Wiley and Sons, Inc.). More typically, however, the sequences obtained as described herein are used to populate a database, which in turn is utilized in conjunction with the computerized systems and programs disclosed herein to conduct the comparison (the databases, computer systems and programs are discussed further infra).

A. Identification of Sequences Active in Particular Cells

In certain methods for analysis of accessible regions and characterization of cells with respect to their accessible regions, a collection of accessible region sequences from one cell is compared to a collection of accessible region sequences from one or more other cells. For example, databases from two or more different cell types can be compared, and sequences that are unique to one or more cell types can be determined. These types of comparison can yield developmental stage-specific regulatory sequences, if the different cell types are from different developmental stages of the same organism. They can yield tissue-specific regulatory sequences, if the different cell types are from different tissues of the same organism. They can yield disease-specific regulatory sequences, if one or more of the cell types is from a diseased tissue and one of the cell types is the normal counterpart of the diseased tissue. Diseased tissue can include, for example, tissue that has been infected by a pathogen, tissue that has been exposed to a toxin, neoplastic tissue, and apoptotic tissue. Pathogens include bacteria, viruses, protozoa, fungi, mycoplasma, prions and other pathogenic agents as are known to those of skill in the art. Hence, comparisons can also be made between infected and uninfected cells to determine the effects of infection on host gene expression. In addition, accessible regions in the genome of an infecting organism can be identified, isolated and analyzed according to the methods disclosed herein. Those skilled in the art will recognize that a myriad of other comparisons can be performed.

B. Mapping Accessible Regions and Identification of Genes and Coding Regions

A collection of nucleotide sequences of accessible regions in a particular cell type is useful in conjunction with the genome sequence of an organism of interest. In one embodiment, information on regulatory sequences active in a particular cell type is provided. Although the sequences of regulatory elements are present in a genome sequence, they may not be identifiable (if homologous sequences are not known) and, even if they are identifiable, the genome sequence provides no information on the tissue(s) and developmental stage(s) in which a particular regulatory sequence is active in regulating gene expression. However, comparison of a collection of accessible region sequences from a particular cell with the genome sequence of the organism from which the cell is derived provides a collection of sequences within the genome of the organism that are active, in a regulatory fashion, in the cell type from which the accessible region sequences have been derived. This analysis also provides information on which genes are active in the particular cell, by allowing one to identify coding regions in the vicinity of accessible regions in that cell.

In addition, the aforementioned comparison can be utilized to map regulatory sequences onto the genome sequence of an organism. Since regulatory sequences are often in the vicinity of the genes whose expression they regulate, identification and mapping of regulatory sequences onto the genome sequence of an organism can result in the identification of new genes, especially those whose expression is at levels too low to be represented in EST databases. This can be accomplished, for example, by searching regions of the genome adjacent to a regulatory region (mapped as described above) for a coding sequence, using methods and algorithms that are well-known to those of skill in the art. The expression of many of the genes thus identified will be specific to the cell from which the accessible region database was derived. Thus, a further benefit is that new probes and markers, for the cells from which the collection of accessible regions was derived, are provided.

In addition to comparing the collection of polynucleotides against the entire genome, the sequences can also be compared against shorter known sequences such as intergenic regions, non-coding regions and various regulatory sequences, for example.

C. Characterization of Disease

Comparisons of collections of accessible region sequences with other known sequences can be used in the analysis of disease states. For instance, collections such as databases of regulatory sequence are also useful in characterizing the molecular pathology of various diseases. As one example, if a particular single nucleotide polymorphism (SNP) is correlated with a particular disease or set of pathological symptoms, regulatory sequence collections or databases can be scanned to see if the SNP occurs in a regulatory sequence. If so, this result suggests that the regulatory sequence and/or the protein(s) which binds to it, are involved in the pathology of the disease. Identification of a protein that binds differentially to the SNP-containing sequence in diseased individuals compared to non-diseased individuals is further evidence for the role of the SNP-containing regulatory region in the disease. For example, a protein may bind more or less avidly to the SNP-containing sequence, compared to the normal sequence.

In other methods, comparisons can be conducted to determine correlation between microsatellite amplification and human disease such as, for example, human hereditary neurological syndromes, which are often characterized by microsatellite expansion in regulatory regions of DNA. Other comparisons can be conducted to identify the loss of an accessible region, which can be diagnostic for a disease state. For instance, loss of an accessible region in a tumor cell, compared to its non-neoplastic counterpart, could indicate the lack of activation of a tumor suppressor gene in the tumor cell. Conversely, acquisition of an accessible region, as might accompany oncogene activation in a tumor cell, can also be an indicator of a disease state.

D. Comparison to Gene Expression Profiles

A library of accessible sites that is specific to a particular cell can be compared with a gene expression profile of the same cell, such as is obtained by DNA microchip analysis. For example, serum stimulation of human fibroblasts induces expression of a group of genes (that are not expressed in untreated cells), as is detected by microchip analysis. See, for example, Iyer et al. (1999) Science 283:83–87. Identification of accessible regions from the same serum-treated cell population can be accomplished by any of the methods disclosed herein. Comparison of accessible regions in treated cells with those in untreated cells, and determination of accessible sites that are unique to the treated cells, identifies DNA sequences involved in serum-stimulated gene activation.

IX. Pharmacogenomics: Elucidating Signal Transduction Pathways and Identification of Drug Targets Determining the location and/or sequence of accessible regions in a given cell is useful in pharmacogenomics. The libraries and methods described herein are also useful in elucidating information about signal transduction pathways involved in gene expression, and in modulating one or more members of a signal transduction pathway to regulate gene expression.

A. Pharmacogenomics

Pharmacogenomics (sometimes termed pharmacogenetics) refers to the application of genomic technology in drug development and drug therapy. In particular, pharmacogenomics focuses on the differences in drug response due to heredity and identifies polymorphisms (genetic variations) that lead to altered systemic drug concentrations and therapeutic responses. See, e.g., Eichelbaum, M. (1996) Clin. Exp. Pharmacol. Physiol. 23(10–11):983–985 and Linder, M. W. (1997) Clin. Chem. 43(2):254–266. The term "drug response" refers to any action or reaction of an individual to a drug, including, but not limited to, metabolism (e.g., rate of metabolism) and sensitivity (e.g., allergy, etc). Thus, in general, two types of pharmacogenetic conditions can be differentiated: genetic conditions transmitted as a single factor altering the way drugs act on the body (altered drug action) and genetic conditions transmitted as single factors altering the way the body acts on drugs (altered drug metabolism).

On a molecular level, drug metabolism and sensitivity is controlled in part by metabolizing enzymes and receptor proteins. In other words, a molecular change in a metabolic enzyme can cause a drug to be either slowly or rapidly metabolized. This can result in overabundant or inadequate amounts of drug at the receptor site, despite administration of a normal dose. Exemplary enzymes involved in drug metabolism include: cytochrome P450s; NAD(P)H quinone oxidoreductase; N-acetyltransferase and thiopurine methyltransferase (TPMT). Exemplary receptor proteins involved in drug metabolism and sensitivity include beta2-adrenergic receptor and the dopamine D3 receptor. Transporter proteins that are involved in drug metabolism include but are not limited to multiple drug resistance-1 gene (MDR-1) and multiple drug resistance proteins (MRPs).

Genetic polymorphism (e.g., loss of function, gene duplication, etc.) in these genes has been shown to have effects on drug metabolism. For example, mutations in the gene TPMT, which catalyzes the S-methylation of thiopurine drugs (i.e., mercaptopurine, azathioprine, thioguanine), can cause a reduction in its activity and corresponding ability to metabolize certain cancer drugs. Lack of enzymatic activity causes drug levels in the serum to reach toxic levels.

The methods of identifying accessible regions described herein can be used to evaluate and predict an individual's unique response to a drug by determining how the drug affects chromatin structure. In particular, alterations to accessible regions, particularly accessible regions associated with genes involved in drug metabolism (e.g., cytochrome P450, N-acetyltransferase, etc.), in response to administration of drugs can be evaluated in an individual subject. Accessible regions are identified, mapped and compared as described herein. For example, an individual's accessible region profile in one or more genes involved in drug metabolism can be obtained. Regulatory accessible region patterns and corresponding regulation of gene expression patterns of individual patients can then be compared in response to a particular drug to determine the appropriate drug and dose to administer to the individual.

Thus, identification of alterations in accessible regions in a subject will allow for targeting of the molecular mechanisms of disease and, in addition, design of drug treatment and dosing strategies that take variability in metabolism rates into account. Optimal dosing can be determined at the initiation of treatment, and potential interactions, complications, and response to therapy can be anticipated. Clinical outcomes can be improved, risk for adverse drug reactions (ADRs) will be minimized, and the overall costs for managing these reactions will be reduced. Pharmacogenomic testing can optimize the drug dose regimen for patients before treatment or early in therapy by identifying the most patient-specific therapy that can reduce adverse events, improve outcome, and decrease health costs.

B. Elucidating Signal Transduction Pathways and Identification of Drug Targets

Analysis of accessible regions also provides information about signal transduction pathways involved in gene regulation. Once identified, the accessible region(s) related to a gene of interest can be sequenced and it can be determined which signal transduction pathways play a role in gene regulation. Furthermore, identification of these signal transduction pathways expands the potential drug targets to include upstream molecules in the implicated pathway(s). Thus, a drug target includes, but is not limited to, nucleotide sequences (e.g., transcriptional binding sites); or a protein or protein complex (e.g., histones, transcription factors, molecules involved in upstream mediation of signal transduction, kinases, phosphatases, membrane-associated receptors). These drug targets can then be readily tested as described herein.

Signal transduction pathways mediate gene expression through a membrane receptor capable of transducing signal to the nucleus through an intricate network of molecules, which in turn control gene expression. Various signal transduction pathways are currently under study. See, e.g., (1999) Science 284:755–770 and articles cited therein and Internet address www.stke.org, accessed on Aug. 11, 2000.

One of the largest and most complex group of membrane receptors is the family of receptors coupled to G-proteins. (see, e.g., Murga et al. (1999) TEM 10(4):122–127. FIG. 12 is a schematic representation of various mitogen-activated protein kinase (MAPK) signaling cascades. Various cell surface receptors transduce signal specified by extracellular stimuli by mediating the activity of intracellular molecules. In turn, MAPKs phosphorylate additional kinases or nuclear transcription factors, thereby regulating the expression of genes.

The JAK (Janus protein tyrosine kinase) and STAT (signal transducer and activator of transcription) protein families form a key portion of many intracellular signaling networks that respond to the presence of extracellular cytokines. The JAK proteins are associated with the cytoplasmic portion of transmembrane cytokine receptors. Ligand-induced aggregation of receptors (often dimerization) brings two or more JAK proteins into sufficient proximity that they are able to phosphorylate one another. The phosphorylated JAKs are then able to phosphorylate the receptors at multiple sites, allowing recruitment of STAT proteins to the activated receptor-JAK complex. The recruited STAT proteins are also phosphorylated by JAKs, allowing them to dimerize and dissociate from the JAK-receptor complex. Dimerization of STATs is mediated by interactions between a SH2 domain on one STAT protein and a phosphotyrosine residue on the other. Phosphorylated STAT dimers translocate to the nucleus and bind to specific DNA sequences, either as a STAT dimer or as a higher-order complex comprising a STAT dimer, thereby participating in the activation of transcription of cytokine-responsive genes. Six STAT proteins, and their homologues, have been identified. Ihle et al. (1996) *Cell* 84:331–334. Both homo- and heterodimers of STAT proteins can be formed.

Receptors with intrinsic tyrosine kinase activity such as, for example, the epidermal growth factor (EGF) receptor, the platelet-derived growth factor (PDGF) receptor and the colony-stimulating factor-1 (CSF-1) receptor, are capable of direct phosphorylation of STAT proteins. Thus, STATs are involved in both JAK-dependent and JAK-independent signaling pathways.

An example of a JAK-STAT pathway is provided by the interferon response. The transmembrane interferon receptor has two subunits, α and β. The presence of extracellular interferon (IFN) induces the formation of αβ dimers. Dimerization of the cytoplasmic components of the IFNα and IFNβ receptors results in phosphorylation of certain tyrosine residues on both subunits, as well as tyrosine phosphorylation of associated JAK proteins. The dimerized, phosphorylated receptor-JAK complex is able to bind intracellular STAT proteins, inducing tyrosine phosphorylation of STAT.

In response to IFNα and/or IFNβ, a complex comprising STAT1, STAT2 and the p48 protein binds to DNA sequences known as interferon-stimulated response elements (ISREs). When cells are exposed to IFNγ, a STAT1 homodimer binds to sequences termed IFNγ-activated sequences (GAS elements).

In another example, a JAK-STAT signal transduction pathway is involved in positive feedback control of transcription of the erythropoietin (EPO) gene. Extracellular EPO induces dimerization of the EPO receptor and its associated JAK2 proteins. This leads to dimerization of the STAT5 protein and translocation of a STAT5 dimer to the nucleus, where it binds to a site in the upstream region of the EPO gene, thereby activating EPO transcription. Quelle et al. (1996) *Mol. Cell. Biol.* 16:1622–1631.

Further details on signaling networks involving JAK and STAT proteins can be found in Darnell et al. (1994) *Science* 264:1415–1421; Ihle (1996) *Cell* 84:331–334; and Darnell (1997) *Science* 277:1630–1635.

Thus, determining accessible regions in a gene of interest will allow reconstruction of a signal transduction pathway. Exemplified herein is a method of reconstructing the signal transduction pathway involved in VEGF expression. It will be apparent that such methods are equally applicable to any gene of interest. FIG. 9 and Example 13 describe how the U87MG cell line (which expresses VEGF at levels 100 fold more than other cell lines) contains a unique accessible region around −1000, relative to the transcriptional start site. Sequencing of the DNA in this unique accessible region revealed the presence of several known regulatory elements, for example an AML-1 binding site and an AP-1 binding site. See FIG. 11.

The JNK family of proteins is also activated by certain growth factors, although less efficiently than the ERK family. Efficient activation of JNK proteins is induced by inflammatory cytokines and cellular stresses of a different nature that can be mediated via G-protein-coupled receptors (GPCR). Bioactive amines, peptides, glycopeptides, phospholipids, proteases, odorants, certain taste ligands and even photons can all promote the functional coupling of their receptor-ligand complex with heterotrimeric G proteins located at the intracellular side of the plasma membrane. This causes a conformational change in three key flexible "switch" regions in the G-protein alpha subunit, thereby promoting the exchange of the bound GDP for GTP and the dissociation of the βγ heterodimers (FIG. 12). In turn, GTP-bound G protein α-subunits and complexes initiate a broad range of intracellular signaling events, including the activation of classic effectors such as adenylyl cyclases, phosphodiesterases and phospholipases, and the regulation of activity of ion channels, ion transporters and several protein kinases. As with tyrosine kinase receptors, GPCR are able to promote the activation of guanine nucleotides exchange factors (GEFs) acting on small GTP-binding proteins of the Ras superfamily. The Ras/Rac pathway is involved in the kinase cascade leading to JNK. Another mammalian cell MAPK scaffold protein, JIP-1 (JNK-interacting protein-1) has been shown to inhibit the JNK activity (FIG. 13(B)). JIP-1 also binds a MKKKK, MKKK and MKK for selective regulation of JNK activation. A third potential MAPK scaffold protein in mammalian cells is a functional MKKK (FIG. 13(C)). MEKK1 binds directly to JNK.

Finally, phosphorylation of AP-1 (Fos/Jun) stimulates interaction with other proteins, for example CBP/p300 which are necessary for AP-1-mediated transcription (Arias et al., (1994) *Nature* 370:226; Bannister et al. (1995) *EMBO* 14:4758). p300 has also been shown to be recruited by AML-1 and, although independent of phosphorylation, it is necessary for AML-1-dependent transcription (Kitabayashi et al. (1998) *EMBO J* 17:2994–3004). CBP is also recruited by nuclear hormone receptors upon their activation by cognate hormones (FIG. 14) and it has been shown that mutual inhibition of the cell surface receptor-regulated AP-1 mediated transcription and nuclear hormone receptor-mediated transcription is due to competition for limited amounts of CBP (Kamei et al. (1996) *Cell* 85:403–414). Therefore, without being bound by one theory, it appears as though VEGF may be directly regulated by AP-1 activation and/or indirectly regulated by competition of AP-1 with other regulatory factors such as AML-1.

Thus, identification of the existence and location of accessible regions in test cells allows for reconstruction of signal transduction pathways. In certain embodiments, for example, cells are exposed to a molecule that is known to bind to the any of the regulatory sites identified in the accessible regions. The effect of that molecule on expression (e.g., by Northern or by immunoprecipitation with antibodies against RNA polymerases) of the related gene and/or on chromatin structure (e.g., by sensitivity to a probe of chromatin structure or immunoprecipitation with antibodies against modified histones) is evaluated. In this way, a role for a signal transduction pathway associated with the binding site can be determined. Note that several signal transduction pathways can converge upon a single gene and that a given signal transduction pathway can affect expression of multiple genes. Furthermore, once identified, molecules which affect upstream components of the signal transduction pathway can be tested for their effects on chromatin structure and/or transcription. As will be readily apparent from the teachings herein, by comparing the effects of these molecules at different stages of the pathway and in various combinations, the role of the various pathways involved in gene regulation can be elucidated.

In addition, sequence analysis and identification of regulatory binding sites in accessible regions can also be used to identify drug targets; potential drugs; and/or to modulate expression of a target gene. As described above, the sequences of accessible regions of genes associated with a disease or condition are examined to identify one or more binding sites for a regulatory molecule and to determine if any of these binding sites are known to form part of a signal transduction pathway. Once a particular signal transduction pathway has been implicated in regulation of the gene of interest, any member of this signal transduction pathway can be a target for regulation. For example, analysis and sequencing of a unique accessible region in cells that overexpress VEGF identified multiple signal transduction pathways, including those associated with AP-1 and AML-1. Thus, upstream molecules involved in the AP-1 or AML-1 pathways (described herein) represent potential drug targets for mediating expression of VEGF.

Additional drug targets can also be identified after identification of accessible region(s), followed by partial or full reconstruction of the signal transduction pathway, has elucidated some of the complexities involved in regulation of the gene interest; for example, if reconstruction of the signal transduction pathway implicates certain upstream molecules as having the desired outcome on gene expression.

The methods of identifying drug targets, and molecules that affect expression of the gene of interest (e.g., drugs) described herein can be used in any suitable cell, including, but not limited to, human cells, animal cells (e.g., farm animals, pets, research animals), plant cells, and/or microbial cells. In plants, as described above, drug targets and effector molecules can be identified for their effects on herbicide resistance, pathogens, growth, yield, compositions (e.g., oils), production of chemical and/or biochemicals (e.g., proteins including vaccines). Methods of identifying drug targets can also find use in identifying drugs which may mediate expression in animal (including human) cells. In certain animals, for instance cows or pigs, drug targets are identified by determining potential regulatory accessible regions in animals with the desirable traits or conditions (e.g., resistance to disease, large size, suitability for production of organs for transplantation, etc.) and the genes associated with these accessible regions. In human cells, drug targets for many disease processes can be identified.

X. Computerized Methods

A number of computerized methods described herein can be utilized to conduct the facile comparison of one or more collections of accessible regions against one or more other collections of accessible regions, or one or more known sequences (e.g., known regulatory sequences) such as the comparisons described above. These computerized methods utilize data structures such as databases that contain the sequences that correspond to the accessible regions identified according to the methods set forth herein. The databases can also include information generated during the comparison and other information concerning the accessible regions as described in greater detail infra.

A. Populating the Database

The sequences corresponding to accessible regions that are input into the database are obtained by first isolating accessible regions according to any of the various methods described herein and then sequencing the isolated polynucleotides as set forth above. One or more polynucleotide sequences that correspond to an accessible region in cellular chromatin are referred to as a record. Thus, a record typically refers to a sequence corresponding to an accessible region in a particular cell or population of cells.

The database can contain a variety of other types of information related to the sequences contained within the database. For example, the database can include information on the library to which the sequence belongs and the name of a gene that the accessible region appears to be adjacent. The sequence can also be cross-tabulated with information regarding the nature of the chromatin sample from which the sequence was obtained. Such information can include, but is not limited to, whether the cells from which the chromatin was obtained were healthy or diseased, the developmental stage of the cells, a patient identifier indicating the identity of the patient from which the sample was obtained and the method by which the accessible regions were identified.

The database that is populated with the sequences corresponding to accessible regions and other related information is typically an internal database which is a private database that is optionally maintained behind a firewall within an enterprise, typically the entity that has identified the accessible regions. However, the database need not be a private database and can be made available to the public. Additionally, the database can include sequence information from the entity that develops and maintains the database, as well as sequence and other related information from external sources.

B. Comparisons

As described herein, a number of different types of comparisons can be conducted using the databases described herein. A "project" refers to a comparison between one or more polynucleotide sequences corresponding to an accessible region and one or more other polynucleotide sequences (the "comparison sequence" or "reference sequence") such as described above. These comparison or reference sequences can be other sequences that correspond to accessible regions from a different chromatin sample, a known regulatory sequence, a cDNA sequence and/or a genomic DNA sequence, for example.

The sequence(s) to be compared against a comparison sequence is(are) typically obtained from an internal database populated as set forth supra, but can also be obtained from an external database. In general, an external database refers to a database that is located outside of the internal database. Most typically, such a database is one that has not been developed and maintained by the entity conducting the comparison but rather has been developed by an entity other than the one that maintains the internal database. Examples of external databases include GenBank and other associated databases that are maintained by the National Center for Biotechnology Information (NCBI), part of the National Library of Medicine. Other examples of external databases include the Blocks database maintained by the Fred Hutchinson Cancer Research Center in Seattle, Wash., and the Swiss-Prot site maintained by the University of Geneva. The comparison or reference sequences can be stored with the sequences being compared on the internal database or can be stored in a separate database that is either another internal database or an external database.

The sequence providing or retrieval process can be executed using standard processing programs. The parameters to be utilized in conducting the search such that sequences having the desired characteristics are identified can be input into a computer/workstation using the sequence comparison algorithms described further below or other appropriate input or processing routines.

Comparison of the polynucleotide sequences stored in the various databases can be conducted using sequence comparison algorithms that are known in the art. The comparisons can be conducted to identify sequences that are identical, have a high degree of homology or that are unique within a collection of sequences. Sequences that are identical or have the requisite degree of homology as input by the user are referred to common sequences since the sequences are common or shared between one or more collections of sequences. Likewise, sequences that are unique to one or more collections are referred to as unique sequences. Common and unique sequences can be common or unique to a selected subset of all the various collections of sequences being compared or to all of the collections being compared. For instance, if four different collections of sequences corresponding to accessible regions are being compared, a common sequence can refer to a sequence that occurs in all of the different collections or only 2 or 3 of the different collections. In like manner, a unique sequence can refer to a sequence that is unique to 2 or 3 of the collections, or to all four of the collections being compared. Sequences such as common and unique sequences that satisfy search criteria are referred to as "hits."

Typically, the comparative methods described herein involve comparisons between polynucleotide sequences to assess the relationship or degree of sequence similarity. Such analyses utilize a sequence alignment algorithm such as BLAST (Basic Local Alignment Search Tool; see, for example, Altschul et al. (1990) J. Mol. Biol. 215:403–410) or the Smith-Waterman algorithm (see, e.g., Smith and Waterman (1981) Adv. Appl. Math. 2:482). Software for performing BLAST analyses is publicly available through the National Center for Biotechnology Information. Other suitable alignment algorithms include the homology alignment algorithm of Needleman and Wunsch, (1970) J. Mol. Biology 48:443 and the search for similarity method of Pearson and Lipman, (1988) Proc. Natl. Acad. Sci. USA 85:2444. Computerized implementations of several sequence comparison algorithms are available in the Wisconsin Genetic Software Package, Genetics Computer Group, 575 Science Drive, Madison, Wis.

These algorithms are designed to identify regions of ungapped similarity between two sequences, although the Smith-Waterman algorithm can handle gaps as well. The algorithms accomplish this by first aligning regions having sequence similarity and then determining the percent identity between the sequences being compared. The alignment is calculated by matching, nucleotide by nucleotide, the regions that have substantial similarity and assigning a score based upon the degree of similarity. For comparisons involving polynucleotides, identical bases are scored with a value of +5, whereas mismatched bases are scored with a value of −4. Regions of contiguous bases having a sufficiently high score are referred to as "High Scoring Pairs," or simply HSPs. The BLAST program is designed to output the score of the best HSP (the BLAST Score). Additionally, for each HSP, the percent identity is calculated; the identity calculation and the alignment are also provided as outputs. A P-value for each HSP is also determined, and represents the probability that the observed sequence similarity results from a random occurrence. Consequently, lower P-Values indicate a greater confidence that the observed similarity is not due to a random event (see, e.g., Karlin and Altschul, (1993) Proc. Natl. Acad. Sci. USA 90:5873–5787).

Comparisons can also be conducted using FASTA, which is a modular set of sequence comparison programs used to compare an amino acid or DNA sequence against all entries in a sequence database. The program was written by Professor William Pearson of the University of Virginia Department of Biochemistry and utilizes the sequence algorithm of Lipman and Pearson and the Smith-Waterman sequence alignment protocol, both of which are referenced above.

As indicated above, the comparisons can be conducted to identify sequences that are common or unique between one or more collections of accessible regions. Such comparisons can identify sequences that are candidate functional accessible sequences, positive or negative regulatory sequences and/or gateway sequences according to the comparative methods set forth supra. Alternatively, accessible sequences in the database can be compared to known sequences. The known sequences can be relatively short sequences such as known regulatory sequences or long sequences such as the genomic sequence of the organism from which a chromatin sample was obtained. Sequences identified through the comparisons (i.e., hits) can then be output using a computer as described in greater detail below. Further information on conducting sequence comparisons is set forth in U.S. Pat. Nos. 5,706,498; 5,966,712; and 5,970,500, each of which is incorporated by reference in its entirety.

A variety of computer platforms can be utilized to conduct the sequence comparison algorithms just described during a project. Workstations from a number of computer manufacturers can be used. Suitable workstations include those manufactured by: Sun Microsystems, Inc. of Mountain View, Calif. (e.g., the Sun-Ultra-Sparc 2™ and the Sun Ultra Sparc Enterprise 4000 ™); Silicon Graphics, Inc. (SGI) of Mountain View, Calif. (e.g., the SGI-Challenge L™ and SGI-Challenge XL™), and by Digital Electronics Corporation (DEC) of Maynard, Mass. (e.g., multiprocessor Alpha ™ systems, the DEC-2100A™ and DEC-8400™). One can also use any of the personal computer systems available from a number of different manufacturers provided the system has sufficient memory, processing capabilities and display capabilities to run the computerized algorithms.

XI. Computer Systems

Various computer systems can be used to store and retrieve the sequence information necessary to conduct the computerized methods described herein. The system can be as simple as a stand-alone computer that is not networked to other computers, provided the system has the necessary processing power to conduct the necessary comparisons. Alternatively, the system can include a networked computer system in which a computer is linked to one or more additional computers such as a server and potentially linked to computers located outside the entity conducting the analysis. The networked system can be an intranet system and/or a system linked to other computers via the Internet. Thus, the computer systems can be Internet based systems or non-Internet based systems.

In general the computer systems are used as follows. A project is commenced by providing or retrieving one or more sequences from an internal database and comparing the sequence or sequences with comparison or reference sequences to identify sequences that satisfy certain input parameters. A comparison against other sequences in the same collection of sequences can also be performed. The sequence providing or retrieval process can be executed using standard processing programs and the comparison can be conducted using the sequence alignment algorithms described above, for example. The parameters to be utilized in conducting the search, can be input into the workstation using the computer algorithms described above or other appropriate input and processing routines. The results of the comparison are then displayed for viewing by the user.

A. General Configurations

1. Local System

FIG. 15 depicts a representative computer system 10 suitable for implementing certain methods described herein. Such a system can be used as a stand-alone system in which the computer is not linked to other computers; in other configurations the computer can be linked to other computers (e.g., via a modem). As shown in FIG. 15, computer system 10 typically includes a bus 12 that interconnects major subsystems such as a central processor 14, a system memory 16, an input/output controller 18, an external device such as a printer 23 via a parallel port 22, a display screen 24 via a display adapter 26, a serial port 28, a keyboard 30, a fixed disk drive 32 via storage interface 34, and a floppy disk drive 33 operative to receive a floppy disk 33A. Many other devices can be connected such as a scanner 60 via I/O controller 18, a mouse 36 connected to serial port 28, a CD ROM player 40 operative to receive a CD ROM 42, or a network interface 44. Source code to implement the methods described herein can be operably disposed in system memory 16 or stored on storage media such as a fixed disk 32 or a floppy disk 33A. Other devices or subsystems can be connected in a similar manner. All of the devices shown in FIG. 15 are not required to practice the methods described herein. The devices and subsystems can also be interconnected in different ways from that shown in FIG. 15. The operation of a computer system 10 such as that shown in FIG. 15 is known in the art; hence, operations of the system are not described in detail herein.

FIG. 16 is an illustration of a representative computer system 10 of FIG. 15 suitable for performing the methods described herein; however, FIG. 16 depicts but one example of many possible computer types or configurations capable of being used with the methods described herein. As depicted in FIG. 16, computer system 10 can include display screen 24, cabinet 20, keyboard 30, a scanner 60, and mouse 36. Mouse 36 and keyboard 30 are examples of "user input devices." Other examples of user input devices include, but are not limited to, a touch screen, light pen, track ball and data glove.

Mouse 36 can have one or more buttons such as buttons 37. Cabinet 20 houses familiar computer components such as floppy disk drive 33, a processor 14 and a storage means (see FIG. 15). As used in this specification "storage means" includes any storage device capable of storing data that can be used in connection with a computer system. Examples of such devices include, but are not limited to, disk drives, ZIP drives, WORM drives, optical medium (e.g., CD-ROM), magnetic tape, solid-state memory and bubble memory. Cabinet 20 can include additional hardware such as input/output (I/O) interface for connecting computer system 10 to external devices such as a scanner 60, external storage, other computers or additional peripheral devices.

In some instances, system 10 includes a computer having a Pentium® microprocessor 14 that runs the WINDOWS® Version 3.1, WINDOWS95®, WINDOWS98®, or WINDOWS2000® operating system by Microsoft Corporation. Of course other microprocessors such as the ATHLON microprocessor manufactured by Advanced Micro Devices, Inc. and the CELERON and XEON microprocessors by Intel can be utilized. The methods and systems can also easily be adapted to other operating systems (e.g., UNIX, LINUX and Apple's operating systems such as OS 9 and OS X) without departing from the scope of the present disclosure.

2. Networked Systems

An exemplary basic networked system suitable for conducting the sequence analyses described herein is depicted in FIG. 17 which is a block diagram showing the general configuration of one example of a suitable system. As shown in FIG. 17, the networked system 70 includes a workstation 80, an internal database 82 located within an organization, an optional external database 84 typically located outside the organization, a communications modem 86 and a network system 88 that allows the workstation 80 to access information from external data storage systems such as the external database 84. Thus, for example, the workstation 80 can be connected via the modem 86 and network system 88 to another database 84 at a research institute or university. As indicated supra, in some instances the external database 84 is the GenBank database or a similar type database maintained by a research institute, university or company. In this manner, sequence information stored on the internal database 82 can be supplemented with sequence information and other related types of information concerning the sequences from an external database 84.

Sequence data corresponding to accessible regions obtained according to the methods set forth herein can be input via workstation 80 directly through a keyboard or indirectly through a computer-readable storage medium such as a floppy disk, computer hard drive, CD-ROM or tape storage device. With certain commercially-available nucleic acid sequencers, sequence data can be directly input into the computer from the sequencer via a data connection between the system and sequencer. The sequence data is stored in a data structure such as the internal database 82 that is connected to the workstation 80.

A somewhat more complex computer system that includes multiple computers is shown in FIG. 18. This is another specific example of a network system that can be utilized for storing, retrieving and comparing polynucleotide sequence data according to the methods described herein. With reference to FIG. 18, certain network systems 100 include a network server 102 and one or more auxiliary computers 104a, 104b (or clients) that can be located within the same organization that has the network server 102 and/or that can be located external to the organization that maintains the network server 102. The network system 100 also includes a network cable 106 to which the network server 102 and auxiliary computers 104a, 104b are connected; the cable 106 is connected to the Internet 110 via an optional firewall 108. The firewall 108 is designed to prevent unauthorized access to the network server 102. The network server is also connected to an internal sequence database 124 that stores the sequence information on isolated accessible regions and other related information.

The network system 100 can be selected from a number of network systems known to those skilled in the art, including, but not limited to, a local area network (LAN) or a wide area network (WAN), using Ethernet or IBM Token Ring, for example. The network system 100 includes the necessary functionality for packaging client calls in established formats such as URL in combination with any parameter information into a format suitable for transmission across a transmission line for delivery to a database server.

The network server 102 includes the hardware and software necessary to permit users to access database sequence and other related data to process user requests and to provide an interface for providing information to the auxiliary computers 104a, 104b. In certain systems, the software run on the network server supports the World Wide Web protocol for providing page data between the server 102 and the auxiliary computers 104a, 104b. Information sufficient to guide one skilled in the art in the selection and use of servers and systems that utilize auxiliary and server computers (e.g., client/server environments) is provided, for example, by Nath, A. (1995) The Guide to SQL Server, 2nd ed., Addison-Wesley Publishing Co., which is incorporated by reference in its entirety.

The network server 102 includes an operating system 112 (e.g., Microsoft WINDOWS95®, Microsoft WINDOWS98®, Microsoft WINDOWSNT®, UNIX, LINUX, and Apple operating systems such as OS 9 and OS X) on which a relational database management system (RDMS) 114, a World Wide Web application 116, and a World Wide Web server 118 are included. The software on the server 102 can be arranged in various configurations. For example, all the software necessary to perform the analyses can be located on a single computer or placed on several different computers.

If the network server 102 includes a World Wide Web application 116, the application includes the executable code required to generate database language statements (e.g., SQL statements). Such executables typically include embedded SQL statements. The application 116 further includes a configuration file 120 that contains pointers and addresses to the various software entities that are located on the server 102 in addition to the different external and internal databases that are accessed in response to a user request. The configuration file 120 also directs requests for server 102 resources to the appropriate hardware, as may be necessary if the server 102 is distributed over two or more different computers.

Usually each of the auxiliary computers 104a, 104b includes a World Wide Web browser 122a, 122b that provides a user interface to the network server 102. The auxiliary computers 104a, 104b are able to construct search requests for retrieving sequence information from a sequence database 124 via such a browser. With access to a browser 122a, 122b, users can typically point and click to user interface elements such as buttons, pull down menus, and other graphical user interface elements to prepare and submit a query that extracts the relevant sequence and/or other related information from the internal database 124. Requests formulated in this manner are subsequently transmitted to the Web application 116 that formats the requests to produce a query that can be used to extract the relevant information from the internal database 124.

When Web-based applications are utilized, the Web application 116 accesses data in the internal database 124 by constructing a query in a database language such as Sybase or Oracle SQL which is then transferred to a relational database management system 114 that in turn processes the query to obtain the pertinent information from the internal database 124. A more detailed summary of the process by which user queries are processed is illustrated in FIG. 19. As shown in this figure, with certain systems the World Wide Web server component of the server 102 provides Hypertext Mark-up Language documents 126, i.e., "HTML pages," to the auxiliary computers 104a, 104b. At the auxiliary computers 104a, 104b, the HTML document 126 provides a user interface 128 that can be utilized by the user to formulate a request for access to the internal database 124. Such requests are converted by the Web application component 116 of the server 102 to a SQL query 130. The database management system 114 of the server 102 uses the SQL query to access the pertinent data in the internal database 124 and to provide the data to the user in an appropriate format. The server subsequently generates a new HTML document that relays the information obtained from the internal database to the auxiliary computers as a view in the user interface 128.

Various other computer communications protocols can be utilized instead of the system described above which uses a World Wide Web server and World Wide Web browser to permit communications between the network server 102 and the auxiliary computers 104a, 104b. In certain systems, for example, calls from clients can be packaged directly as SQL statements, without needing to rely on Web application 116 for a conversion to SQL.

However, for systems 100 that do utilize a World Wide Web server and clients, the system should support a TCP/IP protocol. Local networks such as this are sometimes referred to as "Intranets." Such intranets have the advantage that they permit facile communication with public domain databases on the World Wide Web, such as GenBank. Hence, in certain systems, the auxiliary computers 104a, 104b can directly access data (e.g., via Hypertext links) residing on the Internet databases using a HTML interface provided by Web browsers and Web server 118.

B. Exemplary Databases

In general the databases comprise sequences that correspond to sequences for accessible regions of cellular chromatin that are obtained using the various methods disclosed herein. The databases can include raw sequence data or can also include additional related information. The databases can take a number of different forms or be structured in a variety of ways as those skilled in the art will appreciate.

For example, one general arrangement is a flat file database in which the sequences for accessible regions for different cells or populations of cells are stored in separate partitions. Other partitions can include data relevant to different projects. In another arrangement the sequence data can be partitioned according to whether the sequences have been found to be unique to different databases of sequences.

Certain other databases that store sequences of accessible regions are relational databases. Relational databases typically support a set of operations defined by relational algebra. Such databases typically include tables composed of columns and rows for the data included in the database. Each table of the database has a primary key, which can be any column or set of columns, the values for which uniquely identify the rows in a table. The tables in the database can also include a foreign key that is a column or set of columns, the values of which match the primary key values of another table. Typically, relational databases also support a set of operations (e.g., select, join and combine) that form the basis of the relational algebra governing relations within the database.

One basic arrangement or data model 140 of a relational database 124 is one in which there is a "Sequence Table" or entity 142 and a "Library Table" or entity 144 (see FIG. 20). The Sequence Table 142 contains all the sequences corresponding to accessible regions for any given library. Each sequence in the table is typically identified by a sequence identifier. The "Library Table" 144 includes a list of the various libraries for which sequences of accessible regions have been determined; each library is identified by a library identifier (e.g., LibraryID). Since each library usually includes multiple sequences, each library in the Library Table 144 typically has many different sequences represented in the Sequence Table 142. Hence, each entry in the Library Table 144 can correspond to many entries in the Sequence Table 142. Such multiple relationships are referred to as "one-to-many" relationships and the multiple relationships are depicted by the branches at the Sequence Table 142 in the line that connect the Sequence Table 142 with the Library Table 144.

As just indicated, each library in the Library Table 144 is uniquely specified by a libraryID. The libraries in the database are those generated according to the methods described herein and include the sequences corresponding to accessible regions in a cell or population of cells. One attribute of the Library Table 144 is a source identifier that indicates the source of a chromatin sample from which the accessible regions of a library were obtained. Another attribute is an attribute for the number of sequences that indicates the number of sequences in a library and stored in the database. Other attributes include a cloneID attribute that is utilized to identify the clones from which accessible regions in a library were obtained and an attribute for isolation protocol that describes how the accessible regions were identified. A library description attribute includes a short description of other aspects of a library and a comment attribute allows for a more detailed description.

Other relational databases can include two general modules, a "sequence module" and a "project module." The sequence module can store unannotated sequences (i.e., sequence information only) for accessible regions identified for a particular cell or population of cells. The project module identifies the sequences corresponding to accessible regions by sequence identifiers and can include annotated information regarding each of the identified sequences. In general, such annotations can refer to information about how the sequences relate to one another, if at all, and the source of the sequences.

Such relational databases can be implemented in various ways. For instance, in Sybase™ databases, the tables can be physically segregated into different databases. With Oracle™ databases, in contrast, the various tables are not physically separated, since there is one instance of work space with different ownership specified for different tables. In some configurations, databases for sequences (e.g., sequences being compared, comparison sequences) and project information are all located in a single database on a single computer. In other instances, the various databases are split between different computers.

Still other databases are arranged to include sequence and other related information in a form such as shown in FIG. 21. This figure is a block diagram depicting certain entities of a particular data model 150 of one database 124. In general, each block represents a separate relational table in the database 124. The lines between entities represent relationships between the various entities.

The "Sequence Project Table" 152 (SeqProj Table) is a table that includes all the sequences associated with a particular project. Hence, this table includes all the sequences corresponding to accessible regions in a particular cell or population of cells which are to be compared against other sequences. Each sequence is represented by a distinct sequence identifier (sequenceID). The table 152 can include a variety of other attributes that involve information related to the various sequences. Examples of such attributes include, but are not limited to, a cloneID, sample fields regarding the nature of the sequence, sequence length, various hit attributes and different sequence comparison attributes (e.g., various BLAST values). Such attributes can be provided for each of the sequences in a library.

The clone ID field indicates the identity of the clone from which a particular sequence was obtained. The sample field can include specifics regarding the nature of the cell from which the chromatin sample was obtained including, for example, the type of cell, the developmental stage of the cell, whether the cell was diseased or healthy, or whether the cell was infected or uninfected. The hit identifier field specifies identifying information concerning a sequence that has the requisite sequence similarity to a sequence selected for comparison. The sequence length field indicates the length of the isolated sequence.

The hit source field indicates the database source from which the comparison or reference sequence was obtained. Thus, for example, the hit source field can indicate whether the comparison sequence was obtained from an internal or an external database such as a public domain database (e.g., GenBank). In the case of a public domain database such as GenBank, the field can specifically identify the database within GenBank from which the sequence was obtained. A hit description field can provide descriptive information regarding the comparison or reference sequence. This information can be provided by the user or, in the case of an external database maintained by another organization, the information can simply come from the information provided by the organization maintaining the external database.

The sequence comparison fields (e.g., BLAST fields) can provide information on the key output values from various sequence analysis algorithms. If BLAST comparisons have been made, for example, the fields can include values for the BLAST score, BLAST P-Value and BLAST percent identity.

Another table called the "Project Table" 154 typically includes a record for each project which is identified by a project ID. This table includes data on the results of a project. The attributes of records in the table include one or more hit sequences, each having a sequence identifier. As indicated supra, in comparisons of sequences in different collections of accessible regions, hit sequences can include those determined to be unique or common to the collections being compared. A hit identifier and hit description can be used to indicate the identity and describe a sequence identified as being common to two or more collections. When sequences corresponding to accessible regions are compared to known sequences (e.g., known regulatory sequences or sequences provided in public domain databases), a hit includes sequences identified as being identical to, or having a specified degree of sequence homology to, a known sequence. The hit identifier in this instance can be the identifier provided by the external database for the sequence that has been hit.

In addition to fields that list hits generally, the Project Table 154 can include specific attributes for sequences identified as being common or unique to one or more libraries, as well as sequences that are identical or have a specified degree of homology to known sequences in external databases. The database can also include fields for describing the particular types of sequences identified during a comparison such as potential positive regulatory sequences, potential negative regulatory sequences, gateway sequences and functional accessible sequences (see supra for definitions of these sequences).

The database can optionally include a table denoted as an External Hit Table 156 to summarize information on hits against sequences stored in public domain sequence databases such as GenBank, for example. Hence, if a sequence in the Sequence Project Table 152 matches a sequence in the public database with the requisite degree of specificity as input by the user, then the match from the public database is provided as a record in the External Hit table 156. Typically, each record in this table includes at least a hit ID and a hit description to fully identify the sequence. In like manner, the database can include an Internal Hit Table 158 to summarize information on hits against sequences stored on an internal database. This can be useful when different collections of accessible regions are stored on one or more storage devices within an organization.

Tables referred to as "All Sequences" 160 and "Project Sequences" 162 can be included in the database to enable a user to view sequences associated with a particular project or the results of a particular project. If a user desires access to all sequences associated with a particular project, then the All Sequences Table 160 is accessed. If, however, the user desires only to see those sequences that have been identified through a comparative analysis to be common or unique to different collections, similar to known sequences, or potential regulatory, gateway or functionally accessible sequences, for example, then the Project Sequences Table 162 is accessed.

It should be understood, of course, that the databases are not limited to the foregoing arrangements or structures. A variety of other arrangements will be apparent to those of skill in the art. The tables shown in FIG. 21 can also be associated with those shown in FIG. 20, as those skilled in the art will recognize. For example, the Sequence Table 142 and Library Table 144 can be linked to the Sequence Project Table 152. Further guidance regarding the structure of certain types of bioinformatic databases is provided by, for example, U.S. Pat. Nos. 5,966,712; 5,970,500; 6,023,659; 5,706,498; 5,953,727; and PCT publication WO 00/29984, each of which is incorporated by reference in its entirety.

C. Graphical User Interface

In certain of the computer systems, an interface such as an interface screen that includes a suite of functions is included to enable users to easily access the information they seek from the databases described herein. Such interfaces usually include a main menu page from which a user can initiate a variety of different types of analyses, particularly comparative sequence analyses for collections of accessible regions. The main menu page for the databases described herein generally include buttons for accessing certain types of information, including, but not limited to, project information, the sequence database and interproject comparisons.

By selecting the project information button, a user receives a project information screen that allows the user to input a project identifier in the query screen. The computer system then retrieves a list of information regarding the selected project, such as information on the sequences of the accessible regions associated with the particular project, the nature of the sample from which the chromatin sample was obtained and hits against internal and external databases and comparisons against other libraries. The screen can also permit other types of identifying information to be utilized to allow access to information in the database based on other types of criteria. For example, the project information screen can allow the user to input a particular clone identifier, a hit identifier or description, and receive a listing of projects that include information that match the input parameters.

The sequence database button allows a user to input one or more sequence identifiers to retrieve polynucleotide sequence information on accessible regions and other related sequences. This button also provides screens that allow the user to conduct various types of sequence alignment searches such as those described supra (e.g., BLAST and FASTA) against other collections of sequences for accessible regions or against known sequences contained in external databases such as public databases. Screens are also provided that enable the user to view alignments between accessible regions and other sequences; for example, the screen permits the user to view how selected sequences corresponding to accessible regions overlap genomic sequences.

The interproject comparison button on the main menu facilitates retrieval of sequence or other related information from different projects so that results from various projects can be compared. For example, certain projects may involve comparing accessible regions in certain diseased cells against healthy cells (e.g., cancerous cells against healthy cells) to identify accessible regions that are unique to the cancerous cells. A number of similar comparative projects for different cancer patients can be performed. A researcher may then want to analyze the results of each project (each project corresponding to a different cancer patient) to determine if the accessible regions unique to the cancerous cells is the same for each of the cancerous patients or if there is a variation between patients. Variations between patients could indicate that what appears to be a single type of disease actually is multiple diseases with subtle genetic variations. A number of other types of project comparisons can be conducted to gain insight into cellular differentiation, species similarity and differences, and disease states.

XII. Computer Program Products

A variety of computer program products can be utilized for conducting the various methods and analyses disclosed herein. In general, the computer program products comprise a computer-readable medium and the code necessary to perform the various steps of the methods set forth supra. The computer-readable medium on which the program instructions are encoded can be any of a variety of known medium types, including, but not limited to, floppy disks, hard drives, ZIP drives, WORM drives, magnetic tape and optical medium such as CD-ROMs.

FIG. 22 depicts a flowchart of the major steps in certain program instructions for analyzing accessible regions identified in cellular chromatin. At the start 200 of the process a plurality of collections of polynucleotide sequences is provided or received 202 to a computer microprocessor. Each of the collections comprises a plurality of polynucleotide sequences that corresponds to accessible regions in cellular chromatin, with different collections comprising accessible regions for different samples of cellular chromatin. In a subsequent identification step 204, sequences that are unique or common to one or more of the plurality of collections are identified. Following identification, in a displaying step 206, information concerning the polynucleotide sequences identified during the identification step is displayed for viewing by the user of the program.

As depicted in FIG. 23, the aforementioned code of the program can be expanded to include the code necessary to perform a comparison step 208 to assess sequence similarity between sequences in the different collections. In a decisional step 210, the program determines whether all of the sequences in the plurality of sequences have been compared. If not, the comparison process is repeated until all the sequences in any given collection have been compared against the sequences in the other collections. The computer program can include the necessary code to actually conduct the sequence comparisons or simply include the code necessary to access one or more of the sequence alignment algorithms described supra to conduct a comparison of the polynucleotide sequences in the different collections.

Other computer program products contain the code necessary to perform the steps illustrated in the flowchart shown in FIG. 24. The process starts 220 with a computer providing or receiving 222 a collection of polynucleotide sequences that correspond to accessible regions of chromatin. In a comparing step 224, the various polynucleotides in the collection are compared against one or more known sequences to assess the sequence similarity between the polynucleotide sequences in the collection and the known sequences. Then, in a displaying step 226, information concerning the sequence similarity between the polynucleotide sequences is displayed for a user to view. Here, too, the computer program can include the code to conduct the comparison or simply contain the code necessary to access the known sequence alignment algorithms described above.

Still other computer program products contain the code necessary to allow users to input queries and view project information using the computer systems described herein. Thus, certain programs include code for providing a user interface to allow the user to input information concerning one or more projects and code for displaying information regarding the project or projects of interest. More specifically, certain program products are designed to provide an interface such as those described supra that permit a user to input a query concerning one or more projects. The program also includes code for locating the sequence data that correspond to the query and for displaying information such as sequence data (e.g., sequences common or unique to different collection of accessible sequences, potential regulatory sequences, gateway sequences and functionally accessible sequences) that correspond to the query.

Other program products include code for providing an interface that permits a user to input a query concerning different collections of accessible regions that the user wants to compare. Additionally, the program contains code for identifying sequences that are unique or common between the collections and code for displaying information concerning the results of the sequence comparison. Related computer program products include the code to provide an interface that allows for the input of a query concerning one or more collections of accessible regions and code for identifying sequences within the collection(s) that have sequence similarity with known sequences. For instance, certain programs contain code for overlaying one or more of the sequences within a collection of sequences that correspond to accessible regions on the genomic sequence of the organism from which the chromatin sample was obtained.

The following examples are provided as illustrative of, but not limiting, the claimed subject matter.

EXAMPLES

Example 1

Cell Growth and Isolation of Nuclei for Studies of Nuclease Hypersensitivity

Transformed human embryonic kidney 293 cells were grown in DMEM+10% fetal calf serum, supplemented with penicillin and streptomycin, in a 37° C. incubator at 5% $CO_2$. Typically, two 255 $cm^2$ plates of cells were used in an experiment. When the cells reached greater than 90% confluence (~$2.5 \times 10^7$ cells per plate), medium was removed and the cells were rinsed twice with 5 ml of ice-cold PBS (Gibco/Life Technologies, Gaithersburg, Md.). Cells were then scraped from the plates in 5 ml of ice-cold PBS and combined in a 50 ml conical centrifuge tube. The plates were then washed with 10 ml of ice-cold PBS and the washes were added to the tube. Nuclei were pelleted by centrifugation (1400 rpm for 5 min) and the supernatant was removed. The pellet was mixed by vortexing and, while vortexing, 20 ml of lysis buffer (10 mM Tris pH 7.5, 1.5 mM $MgCl_2$, 10 mM KCl, 0.5% IGEPAL CA-630 (Sigma), 1 mM phenylmethylsulfonyl fluoride, 1 mM dithiothreitol) was added. The cell pellet was resuspended in lysis buffer by pipetting and the tube was centrifuged at 1400 rpm for 5 min. The supernatant was removed and the pellet was resuspended in 20 ml of lysis buffer and centrifuged as before. The final pellet was resuspended in 1.5 ml dilution buffer (15 mM Tris pH 7.5, 60 mM KCl, 15 mM NaCl, 5 MM $MgCl_2$, 0.1 mM dithiothreitol, 10% glycerol), nuclei were counted in a microscope and the solution was adjusted so that a concentration of approximately $10^7$ nuclei per ml was obtained.

Example 2

DNase Treatment of Nuclei

Nuclei, at a concentration of $10^7$ per ml in dilution buffer, were digested with different concentrations of DNase I. DNase I dilutions were prepared by diluting deoxyribonuclease I (Worthington, Freehold, N.J.) in dilution buffer (see previous example) supplemented with 0.4 mM $CaCl_2$. To 100 μl of resuspended nuclei was added 25 μl of a DNase I dilution to give final DNase I concentrations ranging from 0.07 Units/ml to 486 Units/ml in three-fold concentration increments. Digestions were conducted at room temperature for 5 min. Digestion reactions were then stopped by addition of 125 μl of Buffer AL (Qiagen DNeasy™ Tissue Kit) and 12.5 μl of a 20 mg/ml solution of Proteinase K (Qiagen DNeasy™ Tissue Kit), followed by incubation at 70° C. for 10 min. Digested DNA was purified using the DNeasy™ Tissue Kit (Qiagen, Valencia, Calif.) according to the manufacturer's instructions.

Purified DNase-treated DNA was digested with restriction enzyme at 37° C. overnight with 40 Units of restriction enzyme in the presence of 0.4 mg/ml RNase A. For the analysis shown in FIG. 2, an Xba I digestion was conducted. After digestion, DNA was ethanol-precipitated from 0.3 M sodium acetate.

Example 3

Micrococcal Nuclease Treatment of Nuclei

Treatment of nuclei, obtained as described supra, with micrococcal nuclease is conducted as described by Livingstone-Zatchej et al. in *Methods in Molecular Biology*, Vol. 119, Humana Press, Totowa, N.J., pp. 363–378.

Example 4

Treatment of Nuclei with a Chemical Probe

Nuclei are treated with MPE using the following procedure adapted from Cartwright et al., supra. A freshly-diluted stock of 0.4 M $H_2O_2$ is prepared by making a 25-fold dilution of a 30% stock solution. A freshly-prepared stock of 0.5 M ferrous ammonium sulfate is diluted 400-fold in water. A solution of methidiumpropyl EDTA (MPE) is prepared by adding 30 μl of 5 mM MPE to 90 μl of water. To this MPE solution is added 120 μl of the ferrous ammonium sulfate dilution and 2.5 μl of 1 M dithiothreitol (DTT, freshly prepared from powder). To a suspension of nuclei, obtained as described supra, are added, in sequence: 3.5 μl of 0.4 M $H_2O_2$ and 37.5 μl of the MPE/ferrous ammonium sulfate/DTT mixture. The reaction is terminated after an appropriate time period (determined empirically) by addition of 40 μl of 50 mM bathophenanthroline disulfonate, 0.1 ml of 2.5% sodium dodecyl sulfate/50 mM EDTA/50 mM Tris-Cl, pH 7.5 and 10 μl of Proteinase K (10–14 mg/ml). Digestion is conducted at 37° C. for at least 8 hours and the mixture is then extracted twice with phenol/chloroform and once with chloroform. Nucleic acids are precipitated from the aqueous phase by addition of sodium acetate to 0.3 M and 0.7 volume of isopropyl alcohol, incubation on ice for at least 2 hr, and centrifugation. The pellet is washed with 70% ethanol, dried, resuspended in 10 mM Tris-Cl, pH 8 and treated with RNase A (approximately 0.1 mg/ml) for 15 min at 37° C.

Example 5

Blotting and Hybridization

Pellets of precipitated, digested DNA obtained according to Example 2, were resuspended in 22 µl of loading buffer containing glycerol and tracking dyes ("Gel loading solution," Sigma Chemical Corp., St. Louis, Mo.) and incubated at 55° C. for 3–4 hours. Twenty microliters of resuspended sample was loaded onto a 1% agarose gel containing 1×TAE buffer and 0.5 µg/ml ethidium bromide, and electrophoresis was conducted at 22 Volts for 16 hours in Tris-acetate-EDTA buffer. After electrophoresis, the gel was treated with alkali, neutralized, blotted onto a Nytran membrane (Schleicher & Schuell, Keene, N.H.), and the blotted DNA was crosslinked to the membrane by ultraviolet irradiation.

Probes were labeled by random priming, using the Prime-It Random Primer Labeling Kit (Stratagene, La Jolla, Calif.) according to the manufacturer's instructions. In a typical labeling reaction, 25–50 µg of DNA template was used in a final volume of 50 µl. A specific activity of $10^9$ cpm/µg was typically obtained. Labeled probes were purified on a Nuc-Trap probe column (Stratagene #400702, La Jolla, Calif.).

The membrane was placed in a hybridization bottle and pre-hybridized in Rapid Hybridization Buffer (Amersham, Arlington Heights, Ill.) at 65° C. for 15 min. Probe (a 0.1 kb XbaI-KpnI fragment, see FIG. 2A) was added (approximately 0.03 µg containing approximately $3.3 \times 10^7$ cpm) and hybridization was conducted at 65° C. for 2 hours. Following hybridization, the membrane was washed once at 65° C. for 10 min. with 2×SSC+0.1% SDS, and twice at 65° C. for 10 min. with 0.1×SSC+0.1% SDS. The membrane was then dried and analyzed either by autoradiography or with a phosphorimager.

Results are shown in FIG. 2B for analysis of DNase hypersensitivity within a 10.5 kb region comprising the human erythropoietin (EPO) gene in 293 cells. Increasing DNase concentration resulted in the generation of two new DNA fragments, of 3.3 and 3.9 kb, indicating the presence of two DNase hypersensitive sites located downstream of the EPO coding region. See FIG. 2A.

Example 6

Identification of Accessible Regions of Chromatin Using Methylation-Sensitive Restriction Enzymes The restriction enzyme Hpa II cleaves DNA at the recognition sequence CCGG, but does not digest if the second C residue in the recognition sequence is methylated. In this example, the ability of Hpa II to cleave human genomic DNA was contrasted with a restriction enzyme that has a 4-base pair recognition site with no CpG in the sequence (e.g., Rsa I, target site GTAC), and a restriction enzyme that has a 6 base pair recognition site (e.g., Kpn I, target site GGTACC; SEQ ID NO: 1). Total human genomic DNA (5 µg) was digested to completion with each of these restriction enzymes and resolved on a 2% agarose gel alongside 1 kb (lane 1) or 100 bp (lane 5) size markers. See FIG. 3.

As can be seen from FIG. 3, Hpa II cleaved human DNA less efficiently than either Kpn I or Rsa I. The only portions of the genome that were sensitive to Hpa II are those that contain demethylated CpG residues. These are quite rare, and, as a consequence, the average Hpa II digestion product has a size much larger than 3 kbp (FIG. 3, lane 4).

In a separate experiment, a plasmid containing a human genomic DNA fragment was cleaved with Hpa II or Rsa I, the digestion products were fractionated on an agarose gel, blotted to a membrane, and the membrane was incubated, under conditions favoring hybridization, with probes corresponding to either a known regulatory region or to known non-regulatory DNA.

The results, shown in FIG. 4, indicate that a probe for a known regulatory region of DNA (probe B) hybridizes to small products (~100 bp) in the Hpa II digest (Lane 4), while a probe corresponding to non-regulatory DNA (probe A) hybridizes to large fragments in the Hpa II digest (Lane 2). Importantly, when DNA is digested with Rsa I (whose activity is not blocked by methylation), both probes hybridize to DNA fragments having a size greater than 400 bp (Lanes 1 and 3).

Example 7

Single-step Enrichment for an Intact, CpG Island-containing Fragment of the Human TEF-3 Gene by Digestion with Mse I Examination of the nucleotide sequence of the human TEF-3 (transcription enhancer factor-3, also known as RTEF-1) gene (GenBank accession Number AC00591 1) between −2,940 and +3,060, with respect to the P1 transcription startsite, reveals the presence of a CpG-rich region between −660 and +840, marked by the presence of 30 Hpa II sites (i.e., a CpG island). This sequence was searched for the presence of the sequence 5'-TTAA-3' which is the recognition site for the restriction enzyme Mse I. The search revealed the existence of 13 Mse I sites in this region. Of the 14 predicted Mse I fragments from this region, 13 were smaller than 900 nucleotide pairs. The remaining fragment was predicted to have a length of 1,935 nucleotide pairs, extending from −992 to +943, and contained all 30 of the Hpa II sites in the −660 to +840 CpG island. See FIG. 5. This large, 1,935 nucleotide pair fragment is easily separable, by gel electrophoresis or other size separation methods, from all other products of Mse I digestion of this region.

Three DNase I hypersensitive regions were mapped at the following locations (with respect to the TEF-1 transcriptional startsite): −600 to −360, −170 to +70 and +320 to +470. All three of these hypersensitive regions lie within the 1,935 nucleotide pair Mse I fragment. Thus, digestion with Mse I yields a large fragment containing sequences involved in transcriptional regulation of the TEF-3 gene.

Example 8

Single-step Enrichment for an Intact, CpG Island-containing Fragment of the Human CAP-1 Gene by Double Digestion with Mse I and Tsp509 I An analysis similar to that described in example 7, supra, was conducted on an approximately 7-kilobase pair (kbp) segment of the human TRAF-3 (TNF Receptor-Associated Factor, also known as CAP-1) gene; GenBank Accession Number AF 110907. In this case, a CpG-island, containing 38 Hpa II sites, is present between −840 and +900, with respect to the P2 transcriptional startsite. Analysis of the predicted sizes of Mse I fragments in this 7-kbp region revealed the existence of two large Mse I fragments, of 2,784 and 1,623 nucleotide pairs. All other Mse I fragments (nine in total) had sizes less than 800 nucleotide pairs. See FIG. 6. The larger of these fragments extends from −1,718 ton +1,066, encompassing the CpG island.

This sequence was additionally analyzed with respect to the predicted sizes of restriction fragments generated by digestion with the restriction enzyme Tsp509 I, whose recognition sequence is 5'-AATT-3'. Of the 28 fragments predicted to be obtained from a Mse I/Tsp509 I double digest, 27 fragments have a size less than 800 nucleotide pairs. The remaining fragment has a size of 2,639 nucleotide pairs, extending from −1,718 to +921, and including the CpG island. See FIG. 7.

DNase I hypersensitive regions were mapped in the TRAF-3 gene between −1,420 and −1,170, and between −360 and +120. Both of these hypersensitive regions lie within the 2,639 nucleotide pair I fragment generated by Mse I/Tsp509 I double digestion. Thus, digestion with Mse I and Tsp509 I yields a large, easily isolable fragment containing sequences involved in transcriptional regulation of the TRAF-3 gene.

Example 9

Isolation and Analysis of Sequences Released by DNase I Digestion from Bulk Chromatin A. Preparation of Nuclei Normal (e.g., NIH 3T3 fibroblasts) or transformed (e.g., human kidney 293) cells are grown in minimal essential medium under standard conditions. Nuclei are generally isolated as described by Kornberg et al. (1989) *Meth. Enzymol.* 170:3–14; Zaret et al. (1992) *Proc. Natl. Acad. Sci. USA* 89:6540–6544; and Archer et al. (1999) *Meth. Enzymol.* 304:584–599, with modifications. More specifically, cells are rinsed with ice-cold phosphate-buffered saline (PBS), pelleted briefly, and resuspended in nuclei extraction buffer (10 mM Tris-Cl, pH 7.4, 15 mM NaCl, 60 mM KCl, 1 mM EDTA, 0.1 mM EGTA, 0.1% NP-40, 5% sucrose, 0.15 mM spermine, 0.5 mM spermidine, with the last two components being added immediately prior to use). Cells are lysed by homogenization with a Dounce pestle until the majority of the nuclei are released (as gauged by light microscopy). The nuclei are pelleted by centrifugation through a cushion containing 10% sucrose at approximately 1400×g, rinsed with nuclei extraction buffer, and resuspended in a suitable volume of reaction buffer (10 mM HEPES, pH 7.6, 25 mM KCl, 5 mM $MgCl_2$, 5% glycerol, 0.5 mM PMSF, 0.5 mM dithiothreitol).

B. Treatment with DNase I and Purification of Released DNA Fragments

Small volumes (~400 μl) of nuclei, resuspended in reaction buffer, are placed in a 37° C. water bath for exactly 1 min. DNase I (DPRF grade; Worthington Biochemical, Freehold, N.J.) is then added to three of the samples to generate digestion reactions having a DNase concentration of 1, 10, and 100 Worthington units/ml. Aliquots of 100 μl are removed from each sample at 1 min, 3 min, and 5 min following addition of enzyme, and mixed vigorously with an equal volume of stop buffer (20 mM Tris pH 7.4, 200 mM NaCl, 2 mM EDTA, 2% SDS). PCR-grade Proteinase K (Boehringer Mannheim) is added to a final concentration of 700 μg/ml, and following a 16 hr incubation at 37° C., the DNA is extracted once with phenol, once with phenol-chloroform-isoamyl alcohol (25:24:1, v:v:v), and once with chloroform. DNAse-free RNAse A (Roche Molecular Biochemicals) is added to a final concentration of 10 μg/ml, and the samples are incubated at 37° C. for 30 min, followed by an extraction with phenol-chloroform-isoamyl alcohol (25:24:1, v:v:v) and with chloroform.

DNA is precipitated with 0.3 M sodium acetate, (pH 5.2) and two volumes of ethanol at −20° C., and resuspended in TE buffer, followed by fractionation on a 2% high-resolution blend (Amresco; Solon, Ohio) agarose gel in 1×TAE, along with a sample of purified genomic DNA not treated with DNAse I and a low molecular weight DNA size ladder. The gel is stained with ethidium bromide and analyzed on a ChemiImager low light imaging system equipped with a UV transilluminator and a CCD camera. Samples in which 60–80% of the DNA remains undigested by DNAse I, as gauged by comparison with the undigested DNA sample, are chosen for subsequent analysis. From these samples, DNA fragments ranging in size from 100 to 200 base-pairs are purified directly from the gel using a QIAquick gel extraction kit (Qiagen, Valencia, Calif.) and stored in TE buffer for analysis.

C. Analysis of Released DNA Fragments

Serial dilutions of the 100–200 base-pair DNA fragments obtained in the previous step are slot-blotted onto Nytran Supercharge nylon membranes (Schleicher and Schuell, Keene, N.H.) along with a similar dilution series of input genomic DNA (non-digested). The blot is incubated, under hybridization conditions, with a short labeled probe from the DNase hypersensitive site in the rDNA-promoter. Langst et al. (1998) *EMBO J.* 17:3135–3145. An identical blot is hybridized with a probe from the β-globin gene locus control region (LCR). Forrester et al. (1987) *Nucleic Acids Res.* 15:10,159–10,177. As a control, one or more labeled probes located ca. 1–2 kb away from either the mapped hypersensitive sites in the rDNA gene or the β-globin LCR are used to probe identical blots. Preferential hybridization of the rDNA hypersensitive site probe and the globin LCR probe to the 100–200 bp DNA fragments released by DNase, compared to non-digested DNA, is observed. In addition, the control probes hybridize preferentially to non-digested DNA, compared to the 100–200 bp fragments released by DNase.

D. Cloning of Accessible Sequences Released by DNase Digestion

To obtain a library of accessible region sequences, single-stranded extensions in the DNA fragments in the 100–200 bp pool (obtained as described above) are repaired by incubation with T4 DNA polymerase (New England Biolabs, Beverly, Mass.) and the four deoxyribonucleoside triphosphates; and aliquots of the end-repaired DNA are ligated into SmaI-linearized pBluescript II (Stratagene, La Jolla, Calif.) with a rapid ligation kit (Roche Molecular Biochemicals). Ligated material is transformed into XL1Blue competent *E. coli* (Stratagene, La Jolla, Calif.), and plated on IPTG- and X-gal-containing medium. Cells harboring insert-containing plasmids are grown into minicultures, plasmid DNA is purified from the minicultures, and the inserts are characterized by nucleotide sequencing.

E. Sequence Analysis

The genomic location of sequences contained in the library obtained in the previous step is determined by BLAST searches against the publicly-available human genome sequence. Inserts are characterized for enrichment in trans-acting factor binding sites by comparison to the existing databases (TFSITES/GCG, TFSEARCH, TFCLUSTER, TRANSFAC; see, for example, Wingender et al. (2000) *Nucleic Acids Res.* 28:316–319), and those receiving a high score are selected for further analysis. A restriction map of genomic DNA encompassing an accessible region from the library is obtained from the genome sequence, and confirmation of the cloned sequence as an accessible region (i.e., a DHS) within chromatin is verified by preparing nuclei, treating them with DNase, and purifying the treated DNA (as described above), followed by Southern blotting and indirect end-labeling, using a genomnic sequence in the vicinity of the accessible region as probe. Procedures for indirect end labeling are known in the art, and have been described by Nedospasov et al. (1980) *Biochem. Biophyys. Res. Comm.* 29:532–539; and Wu (1980) *Nature* 286:854–860. The locations of DNase hypersensitive sites, as determined by indirect end-labeling, will coincide or overlap with the locations of the accessible regions.

Example 10

Construction of Libraries of Accessible Regions of Chromatin Using Methylation-Sensitive Restriction Enzymes Libraries can be constructed in one of two ways. In one embodiment ☉, total genomic DNA is used as the starting material for Hpa II cleavage. In another embodiment, that is expected to further enrich for regulatory, accessible DNA, nuclei are treated with Hpa II.

A. Use of Genomic DNA as Starting Material

Total genomic DNA is extracted from ca. $1 \times 10^7$ cultured cells with a DNAeasy kit (Qiagen; Valencia, Calif.) to yield approximately 50 µg. The DNA is digested for 16 hours with 300–500 units of Hpa II (New England BioLabs, Beverly, Mass.) in buffer recommended by the enzyme manufacturer and, following a single round of extraction with phenol-chloroform (50:50) and chloroform-isoamyl alcohol (24:1), is resolved on a 2% high-resolution blend agarose gel (Amresco; Solon, Ohio) alongside size markers. DNA ranging in size from ca. 80 to 200 bp is purified by gel extraction using a QiaEasy kit (Qiagen).

B. Use of Nuclei as Starting Material

Normal cells (e.g., NIH 3T3 fibroblasts) or transformed cells (e.g., human 293 kidney cells) are grown in minimal essential medium under standard conditions. Nuclei are isolated as described supra, with modifications. Kornberg et al. (1989) *Methods Enzymol.* 170:3–14. Cells are rinsed with ice-cold phosphate-buffered saline (PBS), pelleted briefly, and resuspended in nuclei extraction buffer (10 mM Tris-Cl, pH 7.4, 15 mM NaCl, 60 mM KCl, 1 mM EDTA, 0.1 mM EGTA, 0.1% NP-40, 5% sucrose, 0.15 mM spermine, 0.5 mM spermidine—last two components are added immediately prior to use). Cells are lysed by homogenization with a Dounce pestle until the majority of the nuclei are released, as gauged by light microscopy. The nuclei are pelleted by centrifugation through a cushion containing 10% sucrose at ~1400 g, rinsed with nuclei extraction buffer, and resuspended in a suitable volume of Hpa II reaction buffer (New-England BioLabs) supplemented with 10 mM NaCl. The nuclei are warmed to 37° C. for 1 minute, and high-concentration Hpa II is added to 600–1000 units/ml. Aliquots of the nuclei are removed at defined time points following enzyme addition (e.g., 3, 6, 12 minutes), and the reaction is stopped by DNA purification with the DNAeasy kit (Qiagen). Following extraction, the DNA is precipitated with 0.3 M sodium acetate, pH 5.2, and ice-cold ethanol at −20° C. for 16 hours, and then resuspended in a small volume of TE buffer. The DNA is resolved on a gel and 100–200 bp fragments are isolated exactly as described above.

C. Analysis of CpG Island Pool

Small aliquots of size-fractionated HpaII-digested DNA, obtained as described supra, are ligated into pBluescript II (Stratagene, La Jolla, Calif.) which has been digested to completion with ClaI, which generates overhangs compatible with those generated by HpaII. The ligation is performed with a rapid ligation kit (Roche Molecular Biochemicals), transformed into XL1Blue competent *E. coli* (Stratagene, La Jolla, Calif.), and plated on IPTG- and X-gal-containing medium. Insert-containing colonies are grown into minicultures and the inserts are characterized by sequencing. The genomic location of the resulting sequences is determined by BLAST searches against the publicly available human genome sequence.

Example 11

Mapping Accessible Sites in the Mouse Bax Gene By DNase I Cleavage and LM-PCR

A. Cell Culture

Mouse NIH3T3 cells are maintained in Dulbecco's Modified Eagle's Medium supplemented with 10% calf serum. When cells reach approximately 90% confluence, they are washed with ice-cold phosphate-buffered saline (PBS), scraped off the plate, and collected by centrifugation at 1,000×g for 2 min.

B. Isolation of Nuclei

The pelleted cells are resuspended in 10 mM Tris-Cl, pH 7.5, 10 mM KCl, 1.5 mM $MgCl_2$, 0.5% IGEPAL and incubated at t room temperature for 2 to 4 min. The cell suspension is then subjected to centrifugation at 1,000×g for 2 min and the supernatant discarded. The pellet (containing nuclei) is resuspended in 10 mM Tris-Cl, pH 7.5, 10 mM NaCl, 60 mM KCl, 5 mM $MgCl_2$, 1 mM $CaCl_2$. Nuclei are counted using a hemocytometer, and the concentration is adjusted, if necessary, to $1-2 \times 10^7$ nuclei/ml, using the same buffer in which the nuclei are dissolved.

C. DNase Treatment

The nuclear suspension is divided into 100 µl portions. Solutions of DNase I (Worthington, Freehold, N.J.) are prepared at concentrations of 0, 5, 10, 20 and 40 µg/ml, in the same buffer in which the nuclei are dissolved (supra). A 100 µl portion of each DNase dilution is added to 100 µl of nuclei and the reactions are incubated at room temperature for 5 min. Reactions are stopped by addition of 200 µl of AL buffer and 20 µl Proteinase K (DNeasy genomic DNA isolation kit, Qiagen, Valenica, Calif.). DNA is purified using a DNeasy DNA isolation kit (Qiagen, Valencia, Calif.) following the manufacturer's instructions. Concentration of purified DNA is determined by absorbance at 260 nm.

D. End repair

To generate blunt ends at sites of double-stranded cleavage by DNase I, one microgram of the purified, DNase-treated DNA from the previous step is incubated with one unit of T4 DNA Polymerase (New England BioLabs, Beverly, Mass.) and 200 µM each of dATP, dCTP, dGTP and dTTP in a final volume of 25 µl containing 10 mM Tris-Cl, pH 7.9, 10 mM $MgCl_2$, 50 mM NaCl, 1 mM dithiothreitol and 50 µg/ml bovine serum albumin. The reaction is incubated for 30 min at 12° C. and the DNA is purified using a Qiaquick PCR purification kit (Qiagen, Valencia, Calif.).

E. Ligation of Adapter

An adapter is ligated to the ends of the DNA molecules from the previous step by constructing the following reaction mixture:

25 µl (1 µg) of purified blunt-ended DNA (from previous step)

20 µl of 110 mM Tris-Cl, pH 7.5, 18 mM $MgCl_2$, 50 mM dithiothreitol, 125 µg/ml bovine serum albumin 25 µl of ligase mix 5 µl of 50 mM MgCl$_2$, 100 mM dithiothreitol, 15 mM ATP, 125 µg/ml bovine serum albumin.

Ligase mix contains the following components:

5 µl adapter oligonucleotide (100 pmoles)

1.5 µl T4 DNA ligase (3 Units/µl, New England BioLabs, Beverly, Mass.)

13.5 µl H$_2$O

The sequence of the adapter oligonucleotide is:

```
                                              (SEQ ID NO:2)
5'-HO-GCGGTGACCCGGGAGATCTGAATTC-OH-3'

(SEQ ID NO:3)
         3'-HO-CTAGACTTAAG-OH-5'
```

The ligation reaction is conducted at 17° C. for 12 hours and the DNA product is purified by ethanol precipitation and resuspended in 23 µl double-distilled H$_2$O. Only one of the strands of the adapter (the upper, longer strand identified as SEQ ID NO:2) will become ligated to the population of DNase-treated DNA fragments, as the shorter strand does not possess a 5'-phosphate group at its blunt end.

F. Amplification

The ligated DNA from the previous step is transferred to a PCR tube, followed by the addition of 1 µl (25 pmol) of adapter-specific primer (SEQ ID NO:2) and 1 µl (25 pmol) of a primer specific for the mouse Bax gene. The 5' end of this primer is located 662 nucleotides upstream of the transcriptional startsite, and the primer has a polarity such that polymerization from the primer proceeds toward the gene. The sequence of the Bax gene-specific primer is:

```
5'-GCCCATCACTGAGAAATCCCTTCC-3'    (SEQ ID NO:4)
```

25 µl of PCR master mix (Roche, Indianapolis, Ind.) is added to a separate tube, and both tubes are placed in a thermal cycler and heated to 94° C. The contents of the tubes are then combined, and the combined reaction mixture is subjected to the following temperature cycles:

1 cycle of 3 min at 94° C.

30 cycles of 0.5 min at 94° C., 0.5 min at 52° C. and 2 min at 68° C.

1 cycle of 10 min at 72° C.

Amplified material is analyzed by electrophoresis in a 1% agarose gel run in Tris-acetate or Tris-borate buffer. Given that the 5'-end of the Bax gene-specific primer is located approximately 660 nucleotides upstream of the transcription startsite, amplification products having sizes of approximately 650, 760, 840, 920 and 1020 nucleotides indicate the presence of accessible regions whose borders are located approximately 11 nucleotides upstream and 100, 180, 260 and 360 nucleotides downstream of the Bax gene transcriptional startsite.

Example 12

Construction of a Library of Accessible Sites using DNase I Cleavage and LM-PCR

Cell culture, isolation of nuclei, DNase I digestion, and end repair with T4 DNA Polymerase are performed as described in Example 11.

A. Ligation of First Adapter to DNase-generated Ends

A double-stranded adapter is ligated to the end-repaired DNase-generated fragments. Ligation is performed as described in the previous example, except that the following adapter oligonucleotide is used:

```
5'-pGCGGTGACCCGGGAGATCTGAATTCTT-OH-3'   (SEQ ID NO:5)

3'-HO-CGCCACTGGGCCCTCTAGACTTAAG-OH-5'   (SEQ ID NO:6)
```

Because the adapter has a two-nucleotide 3'-extension at one end, only the left end of the adapter, as shown above, will be ligated to the repaired DNase-generated ends. Unligated adapters are removed using a Qiaquick PCR purification kit (Qiagen, Valencia, Calif.).

B. Restriction Digestion

Purified DNA from the previous step (1 µg) is digested with 10 Units Rsa I in 10 mM Bis Tris Propane-HCl, 10 mM MgCl$_2$, 1 mM dithiothreitol, pH 7.0. Digested DNA is purified using a Qiaquick PCR purification kit (Qiagen, Valencia, Calif.) and is eluted into 25 µl of double-distilled water.

C. Primer Extension of Fragments Containing a DNase-generated End

To 24 µl (i.e., approximately 1 µg) of Rsa I-digested DNA in a PCR tube, 1 µl (25 pmol) of primer (SEQ ID NO:6) is added. Twenty-five microliters of PCR master mix (Roche, Indianapolis, Ind.) is placed in another PCR tube. The two tubes are placed in a thermal cycler and heated to 94° C., then the contents of the two tubes are combined and mixed. The mixture is incubated at 94° C. for 4 min, 55° C. for 1 min and 68° C. for 2 min. DNA is purified Qiaquick PCR purification kit (Qiagen, Valencia, Calif.).

For fragments having one end generated by DNase digestion and one end generated by Rsa I cleavage, this procedure results in the production of double-stranded molecules having the first adapter sequence (with a two-base 3'-extension) at the DNase-generated end and a single-nucleotide 3' extension (an A residue) at the Rsa I-generated end (due to the terminal transferase activity of the thermophilic DNA Polymerase). Because of this 3'-extension, these molecules are substrates for the succeeding cloning step. Fragments with two Rsa I ends are not do not contain this 3'-extension and therefore will not be cloned.

D. Ligation of Second Adapter to Rsa I-generated Ends

The extended DNA from the previous step is ligated to the double-stranded adapter oligonucleotide shown in FIG. 25 (SEQ ID NOS:7 and 8). This adapter is commercially available from Invitrogen (Carlsbad, Calif.). The "E" in the upper sequence refers to a molecule of DNA topoisomerase covalently attached to the 3'-phosphate moiety of the upper strand. Because of its structure, this adapter can only be ligated to a DNA fragment with a 3'-extension containing a single A residue. Consequently, the right end of this adapter, as shown in FIG. 25, will be ligated to the Rsa I-generated ends of fragments whose other end has been generated by DNase cleavage. Ligation is performed using an Invitrogen (Carlsbad, Calif.) TOPO Walker Kit® according to the manufacturer's instructions, and the ligation products are purified using a Qiaquick PCR purification kit.

E. Amplification

PCR is conducted using primers complementary to the first and second adapters. The first adapter-specific primer is SEQ ID NO:6, supra. The second adapter-specific primer has the following sequence:

5'-AGGCACAGTCGAGGACTTATCCTA-3' (SEQ ID NO.9)

50 pmol of each primer (1 µl of each) is added to 46 µl (0.25 µg) of the purified ligation product of the previous step, in a PCR tube. 50 µl of PCR master mix (Roche, Indianapolis, Ind.) is placed in a separate tube. The two tubes are placed in a thermal cycler and heated to 94° C., then the contents of the two tubes are combined and mixed. The mixture is incubated at 94° C. for 4 min, then for 25 cycles of 94° C. for 0.5 min, 55° C. for 0.5 min and 68° C. for 3 min. A final incubation at 72° C. for 10 min is then conducted. DNA is purified using a Qiaquick PCR purification kit (Qiagen, Valencia, Calif.).

F. Cloning

Amplification products from the previous step are ligated into a pCR®4-TOPO vector, using a TOPO TA cloning® kit according to the manufacturer's instructions (Invitrogen, Carlsbad, Calif.). Ligation products are transformed into *E. coli* and recombinants are selected and analyzed using standard procedures. See, for example, Current Protocols in Molecular Biology, F. M. Ausubel et al., eds., Current Protocols, a joint venture between Greene Publishing Associates, Inc. and John Wiley & Sons, Inc., (1998 Supplement) (Ausubel); and Sambrook, et al. (1989) Molecular Cloning: A Laboratory Manual, 2nd ed.

Example 13

Accessible Regions in the Human VEGF Gene

The presence of DNase hypersensitive sites in the upstream region of the human VEGF gene (Tischer et al. (1991) *J. Biol. Chem.* 266:11,947–11,954) was examined by DNase digestion of nuclei from human 293 cells, followed by indirect end labeling, as described in Examples 1, 2 and 5 supra. Representative results are shown in FIGS. 8 and 10. In the experiment shown in FIG. 8, two accessible regions, centered around +1 (−100 to +100) and −550 (−600 to −500), with respect to the transcriptional startsite, were identified. Similar experiments using different probes indicated the presence of accessible regions centered around −1000, −2000 and −3000. See FIG. 10 for data defining and characterizing the hypersensitive region around −1,000 in U87MG cells.

Comparison of DNase hypersensitive region profiles from different cells indicated that the hypersensitive region centered around −1,000 is present only in chromatin from cells expressing high levels of VEGF. See FIGS. 9 and 10.

Example 14

VEGF Regulatory Elements

Examination of the nucleotide sequence of the functional accessible region associated with the VEGF gene indicated that this region (the unique accessible region centered around −1000) contained several known transcription factor binding sites, for example a target site for the myeloid-specific transcription factor AML-1 and a target site for AP-1. See FIG. 11. This identifies these transcription factors as lead candidates for a VEGF gene regulator and, hence, identifies signal transduction pathways which regulate these factors as potential therapeutic targets for regulation of the VEGF gene.

The presence of binding sites for AP-1, AML-1 and other regulatory factors in a unique accessible region in the VEGF promoter allows reconstruction of one or more of the signal transduction pathways in the regulation of VEGF expression. For example, the activity of AP-1 is augmented by many oncoproteins. In particular, the c-Jun oncoprotein is a component of AP-1 whose its activity is regulated by its N-terminal phosphorylation. A number of angiogenic factors, including VEGF itself, activate AP-1 via the c-Jun N-terminal kinase (JNK) and extracellular regulated kinase (ERK) pathways. (See, also, FIGS. 20–22). Further, JNK and ERK are themselves targets of upstream regulatory pathways that include a large group of interacting proteins (FIG. 12) and play a crucial role in a wide variety of cellular functions. ERK1 and ERK2, also know as $p44^{MAPK}$ and $p42^{MAPK}$, respectively, are rapidly activated by a variety of environmental stimuli, including agonists acting on tyrosine kinase receptors (e.g., epidermal growth factor; EGF) and G-protein-coupled receptors (e.g., thyroid stimulating hormone, TSH). When stimulated, the tyrosine kinase class of receptors transmits signal to ERKs in a multistep process. Activated receptors provide docking sites for adapter proteins (e.g., Shc and GRB2) that promote the recruitment of guanine nucleotide exchange proteins for Ras (e.g., SOS) to the plasma membrane, causing exchange of GDP for GTP bound to Ras. GTP-bound Ras then activates MAPKK kinases (MAPKKKs), represented by Raf family members in FIG. 13(A). Another protein, MP1 (MEK partner 1), appears to be a scaffold protein for ERK (FIG. 13). While MP1 binds MEDK1, it also binds ERK1 and enhances activation of ERK1. MP1 is predicted to increase the efficiency of MKKK activation of the MED1-ERK1 pathway. Finally, activated ERKs are translocated to the nucleus where they phosphorylate their ultimate substrates, e.g., c-Jun. Thus, all of the aforementioned molecules represent therapeutic targets for regulation of the VEGF gene.

Since VEGF is itself capable of activating AML-1 via signal transduction pathways downstream of VEGF, autocrine regulation of VEGF through AML-1 is also suggested.

Example 15

Construction of Libraries Enriched in Accessible CpG Island Sequences

Human embryonic kidney 293 cells were grown in Dulbecco's modified Eagle's medium at 37° C. and 5% $CO_2$ until the cells reached 60% confluence, at which point nuclei were isolated according to the method of Archer et al. (1999) *Meth. Enzymol.* 304:584–599. Briefly, the plate was rinsed with PBS, cells were detached from the plate and washed with PBS, then homogenized (Dounce A) in 10 mM Tris-Cl, pH 7.4, 15 mM NaCl, 60 mM KCl, 1 mM EDTA, 0.1 mM EGTA, 0.1% NP-40, 5% sucrose, 0.15 mM spermine and 0.5 mM spermidine at 4° C. Nuclei were isolated from the homogenate by centrifugation at 1,400×g for 20 min at 4° C. through a cushion of 10 mM Tris-Cl, pH 7.4, 15 mM NaCl, 60 mM KCl, 10% sucrose, 0.15 mM spermine and 0.5 mM spermidine. Pelleted nuclei were resuspended, to a concentration of $2\times10^7$ nuclei per ml, in 10 mM HEPES, pH 7.5, 25 mM KCl, 5 mM $MgCl_2$, 5% glycerol, 0.15 mM spermine, 0.5 mM spermidine, 1 mM dithiothreitol, 0.5 mM phenylmethylsulfonylfluoride (PMSF). 5,000 Units/ml of Hpa II was added and the mixture was incubated at 37° C. for 5 min. EDTA was then added to 50 mM. An equal volume of 1% low-melting point agarose in 1×PBS (warmed to 37° C.) was then added, and the mixture was aspirated into the barrel of a 1 ml tuberculin syringe and incubated at 4° C. for 10 min. The agarose plugs were gently extruded from the syringe, and incubated for 36 hr with gentle shaking at 50° C. in 5 ml of 0.5 M EDTA, 1% SDS, 50 µg/ml Proteinase K.

The plugs were washed 3 times with 5 ml of 1×TE buffer (10 mM Tris-Cl, pH 8.0, 1 mM EDTA), then incubated for 1 hr at 37° C. in 1×TE with 1 mM PMSF, followed by two more washes with 1×TE. The plugs were placed in 2 ml of Sau3AI reaction buffer (100 mM NaCl, 10 mM bis-Tris-propane HCl, pH 7.0, 10 mM MgCl$_2$, 1 mM DTT) for 30 min on ice to allow equilibration. Sau3AI was then added to 2000 units/ml and the plugs incubated with gentle shaking for 16 hr at 37° C. The plugs were then sliced with a razor blade and slices were placed in the well of a 0.8% agarose gel in 1×TAE. The gel was run at 50V for 8 hr, stained with SYBR-Gold, and visualized on a Dark Reader transilluminator.

Fragments having an average size between 50 and 1000 nucleotide pairs were purified from the gel using a Qiagen (Valencia, Calif.) gel extraction kit, according to the manufacturer's instructions.

The fragments purified from the gel are a mixture of Sau 3AI fragments (i.e., fragments having two Sau 3AI ends) and fragments having one Sau 3AI end and one Hpa II end. The latter category of fragments is enriched for accessible sequences containing unmethylated CpG islands. These fragments were preferentially cloned as follows. The pBluescript II KS+vector (Stratagene, La Jolla, Calif.) was digested to completion with Cla I and Bam HI and combined with the population of gel-purified fragments in 20 μl of Rapid DNA Ligation Buffer (Roche Molecular Biochemicals, Indianapolis, Ind.). Five units of T4 DNA ligase was added, and the mixture was incubated at room temperature for 30 min. Under these conditions, Hpa II ends were inserted into the Cla I site and Sau 3AI ends were inserted into the Bam HI site of the vector. The ligation mixture was transformed into competent E. coli DH5α (Gibco/BRL, Gaithersburg, Md.). Colonies harboring insert-containing plasmids were identified as white colonies using blue/white selection for insertion into the lacZ gene of the vector. Insert-containing plasmids were screened for insert length by amplification of plasmid DNA using M13 forward and reverse primers (Invitrogen, Carlsbad, Calif.). Sequences of the inserts were determined using a primer adjacent to the Cla I site of the vector, thereby providing sequences of accessible sites cleaved by Hpa II in chromatin. Depending on fragment size and/or GC-content of sequences adjacent to the Hpa II site, it is also possible to obtain sequence using a primer adjacent to the Bam HI site of the vector.

The following sequences were obtained:

```
                                          (SEQ ID NO:10)
CCGGCCTCGGTGTTTTCGGCTTTTTCCTGGCCCCCGGCCCGCCAGGCCGG

GCCCTCTGCTGCCCGCTGAATGGGAGGGGGGCGGGGTCACGTGGCGGGG

GGAGGGGAGGGCCGTCGCGATC (SEQ ID NO:11)
CCGGGCGCCAAGGGAAGCCGGGCGCTGCCCCCTGCTGGCCAGGTTCGGG

CGCGGCGCCGCGGAGGGGCCTCCCCTCTCTGGAGAGAATTGAAGGGGGT

CCGGTGTGGAGCCCCGGCTGGCTCCGGGCTGGGGCTGACCGGCTCTGTG

ACCTTGGGCAGGTCACTGCATCTCTCCAAGCCTCAGTTTGCACGTCTGT

CAAATAGAGGGGCATTCTCTCACTTTGCAGGGTCCCTGGAAATAAGTGA

GATC
```

These sequences were compared to the human genome sequence, using the BLAST algorithm. Altschul et al. (1990) J. Mol. Biol. 215:403–410. The sequence represented by SEQ ID NO: 10 was found to match (122 out of 122 nucleotides) a single region in the human genome, contained in contig NT 004415.2, that is associated with the replication-associated protein 2 (RPA2) gene on human chromosome 1. The sequence represented by SEQ ID NO: 11 was found to match (248 out of 249 nucleotides) a single region in the human genome, contained in contig NT 004359.2, approximately 23 kilobase pairs upstream of the serotonin receptor ID (HTR1D) gene on human chromosome 1. This sequence could represent a distal enhancer or a locus control region for the HTR1D gene.

A second, similar experiment was conducted and the following sequence was obtained:

```
                                          (SEQ ID NO:12)
GATCGGAGTTCGAGACCAGCCCGGCCAACTGGTGAAACCCTGTCTCTACT

AAAAAAATACAAAAGGAGTTCGAGACCAGCCCGGCCAACTGGTGAAACCC

TGTCTCTACTAAAAAAATACAAAAATTAGCTGGGTGTGGTGGTGCACGCC

TGTCATCCCAGCTACTTGGGAGGCTGAGATAGGAATTAGCTGGGTGTGGT

GGTGCACGCCTGTCATCCCAGCTACTTGGGAGGCTGAGATAGGAGAATCG

CTTGAACCCAGGAGGGGAGGCAGAGGTTGCAGTGAGCCGAGATGGCGCCA

CTGTGAATCGCTTGAACCCAGGAGGGGAGGCAGAGGTTGCAGTGAGCCGA

GATGGCGCCACTGTACTCCGGCCTGGGCAAGAGCAAGACTCCAACCAAAA

AAAAAAAAAAAAGAACTAGCAGTACTCCGGCCTGGGCAAGAGCAAGACT

CCAACCAAAAAAAAAAAAAAAAAGAACTAGCAGTGCCCAGGGCTGTACAC

CAGGTGCCAGTACTGGCAGCAATTCTTCCAGTTATTGTGATAGAGCCCAG

GGCTGTACACCAGGTGCCAGTACTGGCAGCAATTCTTCCAGTTATTGTGA

TAGATTCTCATGACGCTAAAATACCCACTTTGTTATTTAACCCTTGCTAA

TCCACAATGAGTTGTTCTCATGACGCTAAAATACCCACTTTGTTATTTAA

CCCTTGCTAATCCACAATGAGTTGCCAGGTACCAGAATCCTTTGTTACTA

ACCAGACCAGGCTGTTCATTCTTGAACAGCATTGCCAGGTACCAGAATCC

TTTGTTACTAACCAGACCAGGCTGTTCATTCTTGAACAGCATTGGGCATC

ACTTTGTTTTAATAATTCTTGTATGAGAAGAGCACTCTTTTCCTTCTGAT

AGCAGGCATCACTTTGTTTTAATAATTCTTGTATGAGAAGAGCACTCTTT

TCCTTCTGATAGCAATGTGGCTCCAACTACTGGCTGATGTGAGACGGTAC

CGGATGTGGCTCCAACTACTGGCTGATGTGAGACGGTACCGG
```

This sequence was compared to the human genome sequence, using the BLAST algorithm. Altschul et al., supra. Three human sequences matching the sequence identified as SEQ ID NO: 12 were found, all located on Chromosome 11. A perfect match (519 out of 519 nucleotide pairs) and a 518 out of 519 nucleotide pair match were found at locations 7 kilobases upstream and 25 kilobases downstream, respectively, of the human gene for squamous cell carcinoma antigen recognized by T cells (SART1). A 511 out of 515 nucleotide pair match, with 2 gaps, was found with a sequence lying approximately 4.5 kilobases upstream of the human Cathepsin W (CATW) gene.

It is notable that, although approximately 40% of CpG islands in the human genome are contained in repeated sequences (primarily Alu repeats, see, e.g., International Human Genome Sequencing Consortium (2001) Nature 409:860–921) the analysis described in this example did not detect a plurality of repeated sequences.

Example 16

Construction of Libraries Enriched in DNase I-Accessible Sequences

Cell culture and preparation of nuclei are performed as described in Example 15. Pelleted nuclei are resuspended, to a concentration of $2 \times 10^7$ nuclei per ml, in 10 mM HEPES, pH 7.5, 25 mM KCl, 5 mM $MgCl_2$, 5% glycerol, 0.15 mM spermine, 0.5 mM spermidine, 1 mM dithiothreitol, 0.5 mM phenylmethylsulfonylfluoride (PMSF) and warmed to 37° C. for 30 sec. DNase I (DPRF grade, Worthington Biochemicals, Freehold, N.J.) is added to a final concentration of 6 or 12 Units/ml and the mixture is incubated at 37° C. for 1 min. The reaction is stopped by addition of EDTA to 50 mM. Immobilization of DNase-treated nuclei in agarose, SDS/Proteinase K treatment, digestion with Sau 3AI, electrophoresis and purification of digestion products having an average size of 50–1,000 nucleotide pairs are conducted as described in Example 15.

The fragments purified from the gel are a mixture of Sau 3AI fragments (i.e., fragments having two Sau 3AI ends) and fragments having one Sau 3AI end and one DNase I-generated end. The latter category of fragments is enriched for sequences accessible to DNase I in chromatin. These fragments are preferentially cloned as follows. First, two single-stranded oligonucleotides are annealed to form an adapter oligonucleotide containing a Sau 3AI-compatible end. The sequence of the adapter is:

```
5'-P-GATCGAATTCAG-3'    (SEQ ID NO: 13)

3'-CTTAAGTC-5'    (SEQ ID NO: 14)
```

This adapter is ligated to the fragment population using T4 DNA ligase (New England Biolabs, Beverly, Mass.), according to the manufacturer's instructions, at 12° C. overnight using a 100-fold molar excess of adapter over DNA ends. Ligase is inactivated by heating to 65° C. for 20 min. This step results in the conversion of Sau 3AI ends to blunt ends. The population of adapter-ligated fragments is then treated with T4 DNA polymerase (New England Biolabs, Beverly, Mass.), according to the manufacturer's instructions using 100 µM each dNTP, to generate blunt ends at the DNase I-generated ends of the fragments. The fragment population is then digested with Sau 3AI to regenerate the original sticky end, while preserving the blunt nature of the DNase I-generated end.

The resulting population of DNA fragments is inserted into pBluescript II KS that has been digested with Bam HI and Eco RV, under conditions identical to those described in the previous example. Under these conditions, DNase I ends are inserted into the blunt-ended Eco RV site and the regenerated Sau 3AI ends are inserted into the Bam HI site. Transformation and analysis of insert sequences in positive colonies are conducted as described in the previous example. Sequences of the inserts are determined using a primer adjacent to the Eco RV site of the vector, thereby providing sequences of accessible sites cleaved by DNase I in chromatin. Depending on fragment size and/or GC-content of sequences adjacent to the DNase I site, it is also possible to obtain sequence using a primer adjacent to the Bam HI site of the vector.

Example 17

Enrichment of p16 Gene Sequences Associated with Acetylated Histone H3 in HCT15 Cells In this example, chromatin immunoprecipitation (ChIP) was used to enrich a population of DNA fragments comprising regulatory sequences for the p16 tumor suppressor gene, by virtue of their association with acetylated histone H3. A CpG island is located in the p16 gene (GenBank Accession No. AF022809), between about 30 nucleotide pairs upstream, and about 590 nucleotide pairs downstream of the transcriptional startsite identified by Hara et al. (1996) *Mol. Cell. Biol.* 16:859–867. One form of regulation of genes associated with CpG islands is through methylation of C residues within the CpG island. Methylation is generally correlated with repression of transcription, while demethylation of methylated sequences can lead to transcriptional activation. In HCT15 cells, the p16 CpG island is methylated and the p16 gene is inactive. Treatment of HCT15 cells with 5-azacytidine (an inhibitor of CpG methylation) results in activation of p16 transcription.

Untreated and 5-azacytidine-treated HCT15 cells were analyzed by chromatin immunoprecipitation to test for a specific association of acetylated H3 with unmethylated (i.e., active) CpG island sequences. Antibodies to acetylated histone H3 were obtained from Upstate Biotechnology (Lake Placid, N.Y.) and were used for chromatin immunoprecipitation according to the supplier's instructions. Briefly, cultures of HCT 15, a colon carcinoma cell line, were grown for 3 days at 37° C. in McCoy's 5A medium (Gibco BRL, Grand Island, N.Y./Rockville, Md.) supplemented with glutamine, penicillin, streptomycin and 10% fetal bovine serum. Certain cultures were treated with 2 µM 5-azacytidine during the three-day growth period and compared to untreated cultures. When the cells had reached 90% confluence, formaldehyde was added to the culture medium to a final concentration of 1% (v/v). After 15 min, the plate was washed with PBS to remove formaldehyde, cells were scraped from the plate, suspended in PBS and centrifuged at 2,000 rpm for 5 min. Pelleted cells were resuspended in 0.4 ml of 50 mM Tris-Cl, pH 8.1, 10 mM EDTA, 1% sodium dodecyl sulfate and sonicated (40 one-second pulses on a VirSonic sonicator set at a power output of 3.8, with 5-second pauses between pulses), to lyse the cells and shear chromatin to an average DNA length of 300–1,000 nucleotide pairs. The sonicated lysate was divided into two portions, denoted input and immunoprecipitate. Anti-acetylated H3 antibody was added to the immunoprecipitate portion, and immunoprecipitated material was collected. Then, in both portions, formaldehyde crosslinks were reversed, DNA was purified, and the purified DNA was analyzed by means of a real-time quantitative PCR assay, known colloquially as "Taqman®." The DNA was analyzed for the relative proportion of two sequences: (1) a region adjacent to the CpG island located in the 5'-untranslated region of the p16 gene (see above), and (2) a portion of the VEGF gene corresponding to the region from 2324 to 2246 nucleotide pairs upstream of the transcription initiation site. Primers and probes used in this assay are shown in Table 1.

TABLE 1

Primers and probes for ChIP analysis of p16 regulatory regions

|  | Sequence | SEQ. ID NO. |
|---|---|---|
| p16 forward primer | 5'-AATAGCACCTCCTCCGAGCA | 15 |
| p16 reverse primer | 5'-CCCTGTCCCTCAAATCCTCTG | 16 |
| p16 probe | 5'-ACAGCGTCCCCTTGCCTGGAAAG | 17 |

TABLE 1-continued

Primers and probes for ChIP analysis of p16 regulatory regions

| | Sequence | SEQ. ID NO. |
|---|---|---|
| Control forward primer | 5'-GCCCCAGAGGGAAACACAA | 18 |
| Control reverse primer | 5'-CCCCCACCCCCATAAGC | 19 |
| Control probe | 5'-CCTCCATGGTGGTACCCAGCAAGG | 20 |

The results, shown in FIG. 26, show an approximately 10-fold enrichment of p16 CpG island sequences associated with acetylated H3 in 5-azacytidine-treated cells (in which these sequences are unmethylated and the p16 gene is active), compared to untreated cells (in which these sequences are methylated and the p16 gene is inactive). The input controls show that p16 and VEGF sequences (are present in a 1:1 ratio (as expected) in total sheared DNA from either 5-azacytidine-treated or untreated cells. Thus, chromatin immunoprecipitation using antibodies to acetylated H3 can be used to isolate regulatory sequences.

Sequences isolated by this method can be cloned to generate a library, and the nucleotide sequences of members of a library can be determined to generate a database.

Example 18

Design of an Exogenous Regulatory Protein for Regulation of the Vascular Endothelial Growth Factor (VEGF) Gene A hypoxia response element (HRE) sequence is located within the DNase hypersensitive region identified around −1,000 in the human VEGF-A gene (see Example 13). Endothelial PAS domain protein 1 (EPAS-1) binds to the HRE to regulate transcription of VEGF. Tian et al. (1997) *Genes Devel.* 11:72–82. An activation domain has been characterized in the C-terminal region of the EPAS-1 protein, within the region bounded by amino acids 486–639. Maemura et al. (1999) *J. Biol. Chem.* 274:31,565–31,570. This activation domain was fused to 3-finger or 6-finger ZFP binding domains specific to several different sites in the human VEGF-A gene, as shown in Table 2.

TABLE 2

Specificity Of ZFP Binding Domains In The VEGF-A Gene

| ZFP binding domain | # fingers | location of target site(s) |
|---|---|---|
| Zen7a | 3 | −1273; −573 |
| Hum17a | 3 | −1,002, +472 |
| VEGF1 | 3 | −8 |
| VOP30A | 3 | +42, +530 |
| VOP32B | 3 | +434 |
| MX1E | 3 | +851 |
| BVO10A-9A | 6 | +622 |
| BVO12A-11B | 6 | +807 |
| BVO14B-13A | 6 | +852 |

Plasmids encoding fusions between a ZFP binding domain and the EPAS activation domain were constructed by substitution of sequences into the EPO2C construct. For descriptions of EPO2C, see co-owned PCT WO 00/41566 and Zhang et al. (2000) *J. Biol. Chem.* 275:33,850–33,860 (in which it is identified as EPOZFP-862c). This construct contains sequences encoding a fusion protein comprising a nuclear localization signal, a ZFP binding domain specific to the human erythropoietin (EPO) gene, a VP16 activation domain and a FLAG epitope, under the transcriptional control of a CMV promoter and a bovine growth hormone polyadenylation signal.

EPO2C was digested with Not I to release VP16-encoding sequences. A fragment of the human EPAS gene encoding amino acids 481–639 of the protein (which encompasses the activation domain, Maemura et al. (1999) supra.) was amplified using the following primers:

5'-GGATCCGGCCACCGCGGCCGCACGCCCAATAGCCCTGAAGACTATTAC-3' (SEQ ID NO: 21)

(5'-ATGAATTCGCGGCCGCCCCACTGGGTATTGGATCTGCCCCCCAT-3' (SEQ ID NO: 22).

The PCR product was cloned into the NotI site of EPO2C, replacing the VP16 activation domain, to generate pEPO-EPAS.

The pEPO-EPAS plasmid was double-digested with Kpn I and Bam HI, releasing sequences encoding the EPO-specific ZFP binding domain. Sequences encoding the various ZFP binding domains described in Table 2 were constructed as described in co-owned PCT WO 00/41566; PCT WO 00/42219; Zhang et al., supra and Liu et al. (2001) *J. Biol. Chem.* 276:11,323–11,334. Each binding domain sequence was inserted as a Kpn I/Bam HI fragment into Kpn I/Bam HI-digested pEPO-EPAS, to generate a collection of plasmids encoding different VEGF-specific ZFP binding domains fused to the EPAS activation domain.

Human embryonic kidney cells (HEK 293) were grown in DMEM (Dulbecco's modified Eagle medium) supplemented with 10% fetal bovine serum in a 5% $CO_2$ incubator at 37° C. Plasmids encoding ZFP-EPAS activation domain fusions, constructed as described above, were transfected into the cells using LipofectAMINE2000 reagent (Gibco Life Technologies, Gaithersburg, Md.) according to the manufacturer's recommendations. Medium was removed and replaced with fresh medium 16 hours after transfection. Cells were harvested 40 hours after transfection and assayed for VEGF expression using a human VEGF ELISA kit (R&D Systems, Minneapolis, Minn.) according to the manufacturer's instructions.

Results are shown in FIG. 27. The results indicate that the EPAS activation domain is capable of activating VEGF-A expression, when fused to a number of different ZFP DNA-binding domains targeted to various sites in the VEGF-A gene. Analysis of ZFP levels by Hi protein immunoblotting using anti-FLAG antibody (Sigma Chemical Co., St. Louis, Mo.) indicated that the different EPAS-ZFP fusion proteins were expressed in transfected cells at roughly comparable levels.

Example 19

Design of Exogenous Molecules for Regulation of the Human VCAM and Growth Hormone Genes The human VCAM gene has two binding sites for the transcription factor NF-kB in its promoter. The NF-kB transcription factor has two subunits (p65 and p50), one of which, the p65 subunit, comprises a transcriptional activation domain. Accordingly, exogenous molecules targeted to the VCAM gene by virtue of a zinc finger binding domain are particularly effective as transcriptional activators when they comprise a p65 activation domain (or functional fragment) fused to the zinc finger targeting domain.

The human growth hormone (hGH) gene is transcriptionally regulated by the thyroid hormone receptor (TR), being activated by ligand-bound TR and repressed by unliganded TR. Accordingly, exogenous molecules for regulation of hGH gene transcription comprise a fusion between TR (or a functional fragment) and a ZFP binding domain. Activation of gene expression is achieved in the presence, and repression in the absence, of ligand.

Example 20

Regulatory Sequences in the Human INK4A Locus for Identification of Therapeutic Targets and Exogenous Regulatory Molecules The human INK4A locus encodes two tumor suppressor proteins: p14ARF (p14) and p16INK4A (p16). Each protein is encoded by three exons: the promoter and first exon of the mRNA encoding each protein are unique, while the second and third exons are common, although translated in different reading frames. Production of mRNA encoding the two proteins is differentially regulated.

The structure of cellular chromatin in the vicinity of the transcription start site and first exon of the p14-encoding transcript was characterized by nuclease accessibility, as described in Examples 1, 2 and 5, supra. Chromatin structure was examined in a cell line which expresses low levels of p14 mRNA (HCT15) and in cell lines that express high p14 mRNA levels (293 and H596). The results, shown in FIG. 28, indicate the existence of two DNase I hypersensitive regions (HS3 and HS5) in highly-expressing cells, which are not present in cells expressing low levels of p14 mRNA. Moreover, a distinct DNase I hypersensitive region (HS4) is present in the low-level expressing cells, and this hypersensitive region is not found in 293 and H596 cells.

Analysis of the nucleotide sequence encompassed by HS5 indicated the presence of binding sites for the transcription factors SP-1, Trx2 and E2F. Accordingly, exogenous molecules, comprising a fusion of the activation domain of any of these transcription factors to a designed ZFP binding region, can be used for regulation of p14 expression.

Furthermore, members of signal transduction pathways which influence the expression and/or activity of SP-1, E2F and/or Trx2 are targets for anti-cancer therapeutics which modulate expression of the p14 tumor suppressor gene.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entireties for all purposes to the same extent as if each individual publication, patent or patent application were specifically and individually indicated to be so incorporated by reference.

What is claimed is:

1. A method for predicting the response of an individual to a drug, the method comprising:
   (a) determining the location and nature of accessible regions in cellular chromatin of the individual resulting from exposure of the individual to the drug; and
   (b) comparing the location and nature of accessible regions identified in step (a) to previously identified locations and natures of accessible regions associated with a known drug response;
   wherein, if the location and nature of accessible regions identified in step (a) is different from the previously identified locations and natures of accessible regions associated with the known drug response, the response of the individual to the drug is predicted to be different from the known response.

2. The method of claim 1, wherein one or more of the accessible regions is associated with a gene that encodes an enzyme involved in drug metabolism.

3. The method of claim 2, wherein the gene involved in drug metabolism is a cytochrome P450 gene.

4. The method of claim 1, wherein the disease or condition is cancer.

5. The method of claim 1, wherein the disease or condition is cardiovascular disease.

6. The method of claim 1, wherein the disease or condition is osteoporosis.

7. The method of claim 1, wherein the known response is a therapeutic response.

8. The method of claim 7, wherein the known response is a side effect.

9. The method of claim 2, wherein the enzyme involved in drug metabolism is selected from the group consisting of NAD(P)H quinone oxidoreductase, N-acetyltransferase and thiopurine methyltransferase.

10. The method of claim 1, wherein one or more of the accessible regions is associated with a gene that encodes a receptor protein.

11. The method of claim 10, wherein the receptor protein is selected from the group consisting of the beta-2 adrenergic receptor and the dopamine D3 receptor.

12. The method of claim 1, wherein one or more of the accessible regions is associated with a gene that encodes a transporter protein.

13. The method of claim 12, wherein the transporter protein is encoded by the MDR-1 gene.

14. The method of claim 12, wherein the transporter protein is a multiple drug resistance protein.

* * * * *